(12) United States Patent
Coppedge et al.

(10) Patent No.: US 11,484,339 B2
(45) Date of Patent: Nov. 1, 2022

(54) PASSIVE SAFETY INTRAOSSEOUS DEVICE

(71) Applicant: June Access IP, LLC, Germantown, TN (US)

(72) Inventors: Billie Coppedge, Germantown, TN (US); Ed Karpowicz, Sewell, NJ (US); Kevin Tesreau, Germantown, TN (US); William S. Parks, Cordova, TN (US); Joseph E. Holley, Jr., Eads, TN (US); Michael Neel, Memphis, TN (US)

(73) Assignee: June Access, IP LLC, Germantown, TN (US)

( * ) Notice: Subject to any disclaimer, the term of this patent is extended or adjusted under 35 U.S.C. 154(b) by 880 days.

(21) Appl. No.: 16/376,821

(22) Filed: Apr. 5, 2019

(65) Prior Publication Data

US 2020/0214741 A1     Jul. 9, 2020

Related U.S. Application Data

(63) Continuation-in-part of application No. 16/125,767, filed on Sep. 10, 2018, now abandoned.
(Continued)

(51) Int. Cl.
*A61B 17/34* (2006.01)
*A61B 17/16* (2006.01)
(Continued)

(52) U.S. Cl.
CPC ........ *A61B 17/3472* (2013.01); *A61B 17/164* (2013.01); *A61B 17/1615* (2013.01);
(Continued)

(58) Field of Classification Search
CPC ............ A61B 17/3472; A61B 17/1615; A61B 17/1622; A61B 17/1626; A61B 17/164;
(Continued)

(56) References Cited

U.S. PATENT DOCUMENTS

| 2,317,648 A | 4/1943 | Siqveland |
| 2,526,662 A | 10/1950 | Hipps et al. |

(Continued)

FOREIGN PATENT DOCUMENTS

| CA | 2237919 | 9/2007 |
| CA | 2593681 | 6/2009 |

(Continued)

OTHER PUBLICATIONS

Promethus Medical Ltd. "Prometheus Pin," retrieved from Internet Aug. 16, 2020, pp. 1-2. <URL: https://www.prometheusmedical.co.uk/sites/default/files/equipment-pdfs/PIN%20Leaflet%202018.pdf>.
(Continued)

*Primary Examiner* — Nathan R Price
*Assistant Examiner* — Mark A Igel
(74) *Attorney, Agent, or Firm* — MacMillan, Sobanski & Todd, LLC

(57) ABSTRACT

A portable and passive safety intraosseous device to allow for direct introduction of medications, etc., within the intermedullary space of a subject patient's bone or, if needed, the removal of certain substances from such a subject patient's bone. Such a device permits direct drilling and placement of a cannula within the subject bone with access external to the subject patient's skin, permitting, as well, connection of a tube for such introduction/removal purposes. The ability to provide a passive safety unit allows for facilitated utilization in, for instance, emergency situations with the entire device provided for utilization thereof. The device includes a drilling component with a permanently attached stylet and a removable cannula, a power supply for a single drilling operation, a mechanism to draw the stylet back into the drill component after use and disengagement from the cannula, and an automatic closure that activates with the separation of the cannula.

20 Claims, 37 Drawing Sheets

Related U.S. Application Data

(60) Provisional application No. 62/566,498, filed on Oct. 1, 2017, provisional application No. 62/556,337, filed on Sep. 9, 2017.

(51) Int. Cl.
    *A61B 17/00*     (2006.01)
    *A61B 17/88*     (2006.01)
    *A61B 90/00*     (2016.01)
    *A61M 39/10*     (2006.01)

(52) U.S. Cl.
    CPC ...... *A61B 17/1622* (2013.01); *A61B 17/1626* (2013.01); *A61B 17/3415* (2013.01); *A61B 17/3421* (2013.01); *A61B 17/3423* (2013.01); *A61B 17/8805* (2013.01); *A61B 17/1637* (2013.01); *A61B 17/3401* (2013.01); *A61B 17/8819* (2013.01); *A61B 17/8847* (2013.01); *A61B 2017/0046* (2013.01); *A61B 2017/00477* (2013.01); *A61B 2090/064* (2016.02); *A61B 2090/0801* (2016.02); *A61M 39/10* (2013.01); *A61M 2210/02* (2013.01)

(58) Field of Classification Search
    CPC ............ A61B 17/3415; A61B 17/3421; A61B 17/3423; A61B 17/8805; A61B 17/1637; A61B 17/3401; A61B 17/8819; A61B 17/8847; A61B 2090/064; A61B 2090/0801; A61B 2017/0046; A61B 2017/00477; A61M 39/10; A61M 2210/02; A61M 2005/3247; A61M 5/326
See application file for complete search history.

(56) References Cited

U.S. PATENT DOCUMENTS

| | | | |
|---|---|---|---|
| 3,452,741 A * | 7/1969 | Schaffer | A61B 17/32 600/568 |
| 3,709,630 A * | 1/1973 | Pohl | A61B 17/1628 415/199.5 |
| 3,919,541 A | 11/1975 | Chao | |
| 4,269,192 A | 5/1981 | Matsuo | |
| 5,012,605 A * | 5/1991 | Nishioka | F41A 17/54 42/70.07 |
| 5,176,656 A * | 1/1993 | Bayless | A61M 5/326 128/919 |
| 5,201,720 A * | 4/1993 | Borgia | A61M 5/326 604/232 |
| 5,300,045 A * | 4/1994 | Plassche, Jr. | A61M 25/0618 604/161 |
| 5,312,364 A | 5/1994 | Jacobs | |
| 5,350,355 A | 9/1994 | Sklar | |
| 5,611,352 A * | 3/1997 | Kobren | A61B 10/0275 600/564 |
| 5,626,595 A | 5/1997 | Sklar et al. | |
| 5,628,751 A * | 5/1997 | Sander | A61B 17/1633 606/86 R |
| 5,632,758 A | 5/1997 | Sklar | |
| 5,672,160 A * | 9/1997 | Osterlind | A61M 25/0631 604/263 |
| 5,762,639 A | 6/1998 | Gibbs | |
| 5,800,362 A | 9/1998 | Kobren et al. | |
| 6,017,354 A * | 1/2000 | Culp | A61B 17/1626 604/22 |
| 6,135,769 A | 10/2000 | Kwan | |
| 6,217,561 B1 | 4/2001 | Gibbs | |
| 6,247,928 B1 | 6/2001 | Meller et al. | |
| 6,287,114 B1 | 9/2001 | Meller et al. | |
| 6,322,540 B1 * | 11/2001 | Grabis | A61M 5/3257 604/110 |
| 6,468,248 B1 | 10/2002 | Gibbs | |
| 6,540,694 B1 * | 4/2003 | Van Bladel | A61B 10/0266 600/564 |
| 6,547,561 B2 | 4/2003 | Meller et al. | |
| 6,613,022 B1 * | 9/2003 | Doyle | A61M 5/326 604/192 |
| 6,616,446 B1 * | 9/2003 | Schmid | B23Q 17/0957 433/224 |
| 6,692,200 B2 | 2/2004 | Peterson | |
| 6,761,726 B1 | 7/2004 | Findlay et al. | |
| 6,905,486 B2 | 6/2005 | Gibbs | |
| 7,347,840 B2 | 3/2008 | Findlay et al. | |
| 7,393,114 B2 | 7/2008 | Devlin | |
| 7,598,526 B2 | 3/2009 | Lohr et al. | |
| 7,591,790 B2 | 9/2009 | Pflueger | |
| 7,621,934 B2 | 11/2009 | Bodduluri et al. | |
| 7,670,328 B2 | 3/2010 | Miller | |
| 7,699,850 B2 | 4/2010 | Miller | |
| 7,811,260 B2 | 10/2010 | Miller et al. | |
| 7,815,642 B2 | 10/2010 | Miller | |
| 7,850,620 B2 | 12/2010 | Miller et al. | |
| D633,199 S | 2/2011 | MacKay et al. | |
| 7,951,089 B2 * | 5/2011 | Miller | A61B 10/025 600/568 |
| 8,038,664 B2 | 10/2011 | Miller et al. | |
| 8,043,316 B2 | 10/2011 | Hardin | |
| 8,133,247 B2 | 3/2012 | Bodduluri et al. | |
| 8,162,852 B2 | 4/2012 | Norris | |
| 8,220,367 B2 | 7/2012 | Hsu | |
| 8,246,584 B2 | 8/2012 | Aravena et al. | |
| 8,286,723 B2 * | 10/2012 | Puzio | B25B 23/14 173/183 |
| 8,292,891 B2 | 10/2012 | Browne et al. | |
| 8,308,693 B2 | 11/2012 | Miller et al. | |
| 8,323,250 B2 * | 12/2012 | Chong | A61L 15/58 604/890.1 |
| 8,333,769 B2 | 12/2012 | Browne et al. | |
| 8,388,623 B2 | 3/2013 | Browne et al. | |
| 8,403,072 B2 | 3/2013 | Eshleman et al. | |
| 8,418,778 B2 | 4/2013 | Eshleman et al. | |
| 8,419,683 B2 * | 4/2013 | Miller | A61B 10/025 604/117 |
| 8,465,491 B2 | 6/2013 | Yedlicka et al. | |
| 8,480,632 B2 | 7/2013 | Miller et al. | |
| 8,480,672 B2 | 7/2013 | Browne et al. | |
| 8,486,027 B2 | 7/2013 | Findlay et al. | |
| 8,506,568 B2 | 8/2013 | Miller | |
| 8,562,615 B2 | 10/2013 | Browne et al. | |
| 8,608,764 B2 * | 12/2013 | Ambardekar | A61B 17/32002 606/170 |
| 8,617,085 B2 | 12/2013 | Moran, Jr. | |
| 8,641,715 B2 * | 2/2014 | Miller | A61B 17/34 606/80 |
| 8,656,929 B2 | 2/2014 | Miller et al. | |
| 8,663,231 B2 | 3/2014 | Browne et al. | |
| 8,668,698 B2 | 3/2014 | Miller et al. | |
| 8,684,978 B2 | 4/2014 | Miller et al. | |
| 8,690,791 B2 | 4/2014 | Miller | |
| 8,715,287 B2 | 5/2014 | Miller | |
| 8,800,679 B2 | 8/2014 | Eshleman et al. | |
| 8,800,680 B2 | 8/2014 | Eshleman et al. | |
| 8,870,872 B2 | 10/2014 | Miller | |
| 8,876,826 B2 | 11/2014 | Miller | |
| 8,894,654 B2 | 11/2014 | Anderson | |
| 8,944,069 B2 | 2/2015 | Miller et al. | |
| 8,974,410 B2 * | 3/2015 | Miller | A61M 39/02 604/116 |
| 8,992,535 B2 | 3/2015 | Miller | |
| 8,998,848 B2 | 4/2015 | Miller et al. | |
| 9,072,543 B2 | 7/2015 | Miller et al. | |
| 9,078,637 B2 | 7/2015 | Miller | |
| 9,199,362 B2 | 12/2015 | Eshleman et al. | |
| 9,211,636 B2 | 12/2015 | Eshleman et al. | |
| 9,266,178 B2 | 2/2016 | Eshleman et al. | |
| 9,295,487 B2 | 3/2016 | Miller et al. | |
| 9,314,228 B2 | 4/2016 | Miller | |
| 9,314,270 B2 | 4/2016 | Miller | |
| 9,321,155 B2 | 4/2016 | Eshleman et al. | |
| 9,321,156 B2 | 4/2016 | Eshleman et al. | |

(56) References Cited

U.S. PATENT DOCUMENTS

| | | | |
|---|---|---|---|
| 9,393,031 | B2 | 7/2016 | Miller |
| 9,414,815 | B2 | 8/2016 | Miller et al. |
| 9,414,816 | B2 | 8/2016 | Rhad et al. |
| 9,433,400 | B2 | 9/2016 | Miller |
| 9,439,667 | B2 | 9/2016 | Miller |
| 9,451,968 | B2 | 9/2016 | Miller et al. |
| 9,457,180 | B2 | 10/2016 | Eshleman et al. |
| 9,480,483 | B2 | 11/2016 | Browne et al. |
| 9,504,477 | B2 | 11/2016 | Miller et al. |
| 9,510,910 | B2 | 12/2016 | Miller et al. |
| 9,545,243 | B2 | 1/2017 | Miller et al. |
| 9,615,816 | B2 | 4/2017 | Woodard |
| 9,675,757 | B2 * | 6/2017 | Harrison ............ A61M 5/2033 |
| 9,717,564 | B2 | 8/2017 | Miller et al. |
| 9,717,847 | B2 | 8/2017 | Miller et al. |
| 9,724,106 | B2 | 8/2017 | Browne et al. |
| 9,851,060 | B2 | 12/2017 | Pathy |
| 9,872,703 | B2 | 1/2018 | Miller et al. |
| 9,883,853 | B2 | 2/2018 | Woodard et al. |
| 9,949,755 | B2 | 4/2018 | Hanson et al. |
| 9,968,373 | B1 | 5/2018 | Greenhalgh et al. |
| 10,016,217 | B2 | 7/2018 | Miller |
| 10,052,111 | B2 | 8/2018 | Miller et al. |
| 10,064,630 | B2 | 9/2018 | Forman et al. |
| 10,092,320 | B2 | 10/2018 | Morgan et al. |
| 10,130,343 | B2 | 11/2018 | Miller et al. |
| 10,166,332 | B2 | 1/2019 | Miller et al. |
| 10,238,420 | B2 * | 3/2019 | Karve ................ A61B 10/025 |
| 10,245,010 | B2 | 4/2019 | Miller et al. |
| 10,258,316 | B2 | 4/2019 | Rhad et al. |
| 10,307,038 | B2 | 6/2019 | Sniffin et al. |
| 10,335,194 | B2 | 7/2019 | Greenhalgh et al. |
| 10,413,282 | B2 | 9/2019 | Miller |
| 10,456,169 | B2 | 10/2019 | Miller |
| 10,492,830 | B2 | 12/2019 | Miller |
| 10,512,474 | B2 | 12/2019 | Miller et al. |
| 2003/0050607 | A1 * | 3/2003 | Gagnieux ............ A61M 5/326 128/919 |
| 2003/0212370 | A1 * | 11/2003 | Barrelle ............ A61M 5/326 604/198 |
| 2003/0225344 | A1 | 12/2003 | Miller |
| 2003/0225411 | A1 | 12/2003 | Miller |
| 2004/0158172 | A1 * | 8/2004 | Hancock ............ A61B 10/0275 600/564 |
| 2005/0148939 | A1 | 7/2005 | Gibbs |
| 2005/0165403 | A1 * | 7/2005 | Miller ................ A61B 10/025 600/567 |
| 2005/0261693 | A1 * | 11/2005 | Miller ................ A61B 17/3472 606/80 |
| 2006/0167378 | A1 * | 7/2006 | Miller ................ A61M 5/158 600/568 |
| 2006/0167379 | A1 | 7/2006 | Miller |
| 2007/0066987 | A1 * | 3/2007 | Scanlan ............ A61B 17/3472 600/564 |
| 2007/0100287 | A1 | 5/2007 | Gibbs |
| 2007/0276352 | A1 * | 11/2007 | Crocker ............ A61B 10/025 604/35 |
| 2008/0015467 | A1 | 1/2008 | Miller |
| 2008/0015468 | A1 | 1/2008 | Miller |
| 2008/0045965 | A1 * | 2/2008 | Miller ................ A61B 46/00 606/80 |
| 2008/0161845 | A1 | 7/2008 | Murakami et al. |
| 2008/0215056 | A1 * | 9/2008 | Miller ................ A61B 17/1628 606/80 |
| 2008/0221580 | A1 * | 9/2008 | Miller ................ F41A 17/54 606/80 |
| 2009/0247900 | A1 * | 10/2009 | Zimmer ............ A61B 10/0275 600/564 |
| 2009/0247901 | A1 | 10/2009 | Zimmer |
| 2010/0057005 | A1 | 3/2010 | Aravena et al. |
| 2010/0106015 | A1 | 4/2010 | Norris |
| 2010/0137740 | A1 | 6/2010 | Miller |
| 2010/0159422 | A1 | 6/2010 | Gibbs |
| 2011/0184312 | A1 | 7/2011 | Moran, Jr. |
| 2011/0245833 | A1 * | 10/2011 | Anderson ............ B23B 49/02 606/80 |
| 2013/0072938 | A1 * | 3/2013 | Browne ............ A61B 17/3494 606/84 |
| 2013/0102924 | A1 | 4/2013 | Findlay et al. |
| 2013/0261650 | A1 | 10/2013 | Hanson et al. |
| 2014/0262880 | A1 | 9/2014 | Yoon |
| 2014/0288499 | A1 | 9/2014 | Miller |
| 2015/0196294 | A1 * | 7/2015 | Murillo ................ A61B 17/062 606/145 |
| 2015/0223786 | A1 | 8/2015 | Morgan et al. |
| 2015/0272596 | A1 * | 10/2015 | Vij ......................... A61B 5/055 600/417 |
| 2016/0022282 | A1 | 1/2016 | Miller et al. |
| 2016/0183974 | A1 | 6/2016 | Miller |
| 2017/0202562 | A1 | 7/2017 | Woodard |
| 2017/0303962 | A1 | 10/2017 | Browne et al. |
| 2017/0311981 | A1 * | 11/2017 | Real ................... A61B 17/3421 |
| 2017/0340401 | A1 | 11/2017 | Miller et al. |
| 2018/0116642 | A1 * | 5/2018 | Woodard ............ B23B 31/103 |
| 2018/0116693 | A1 * | 5/2018 | Blanchard ............ A61M 39/10 |
| 2018/0125465 | A1 | 5/2018 | Muse et al. |
| 2018/0132894 | A1 | 5/2018 | Miller et al. |
| 2018/0221570 | A1 | 8/2018 | Morgan, III et al. |
| 2018/0228509 | A1 * | 8/2018 | Fojtik ................ A61B 10/0233 |
| 2018/0256201 | A1 | 9/2018 | Greenhalgh et al. |
| 2018/0256209 | A1 * | 9/2018 | Muse ................... A61M 5/329 |
| 2018/0317963 | A1 | 11/2018 | Miller |
| 2018/0353191 | A1 | 12/2018 | Miller et al. |
| 2018/0360468 | A1 | 12/2018 | Forman et al. |
| 2019/0015133 | A1 | 1/2019 | Morgan et al. |
| 2019/0083070 | A1 | 3/2019 | Miller et al. |
| 2019/0105122 | A1 | 4/2019 | Miller et al. |
| 2019/0134301 | A1 | 5/2019 | Miller et al. |
| 2019/0216444 | A1 | 7/2019 | Miller et al. |
| 2019/0307468 | A1 | 10/2019 | Fumex et al. |
| 2020/0054350 | A1 | 2/2020 | Miller |

FOREIGN PATENT DOCUMENTS

| | | | |
|---|---|---|---|
| CA | ID128235 | 12/2009 | |
| CA | ID128236 | 1/2011 | |
| CA | 2634696 | 10/2012 | |
| CA | 2706528 | 4/2016 | |
| CN | 109963519 | 7/2019 | |
| CN | 110087568 | 8/2019 | |
| CN | 110430820 | 11/2019 | |
| EP | 0984809 | 8/2005 | |
| EP | 2231041 | 8/2015 | |
| GB | 2551257 A * | 12/2017 | ............ A61B 17/164 |
| JP | 2019531832 | 11/2019 | |
| JP | 2019535457 | 12/2019 | |
| WO | WO2018075694 | 4/2018 | |
| WO | WO2018081632 | 5/2018 | |
| WO | WO2018165334 | 9/2018 | |
| WO | 2019051343 A1 | 3/2019 | |
| WO | WO-2019051343 A1 * | 3/2019 | ......... A61B 17/1615 |

OTHER PUBLICATIONS

International Bureau of WIPO. International Preliminary Report on Patentability for PCT application No. PCT/US2018/050134, dated Mar. 10, 2020, pp. 1-5.

The extended European search report, Application No. 18853356.6, dated Apr. 19, 2021.

Pyng Medical. "Fast1 Sternal IO," pp. 1-9, retreived from Internet Jan. 29, 2020: <URL: http://www.pyng.com/fast1/>.

International Searching Authority. International Search Report and Written Opinion for international application No. PCT/US18/50134, dated Dec. 31, 2018, pp. 1-12.

PCT International Search Report and Written Opinion, Application No. PCT/US2020/023813, dated Jun. 25, 2020.

* cited by examiner

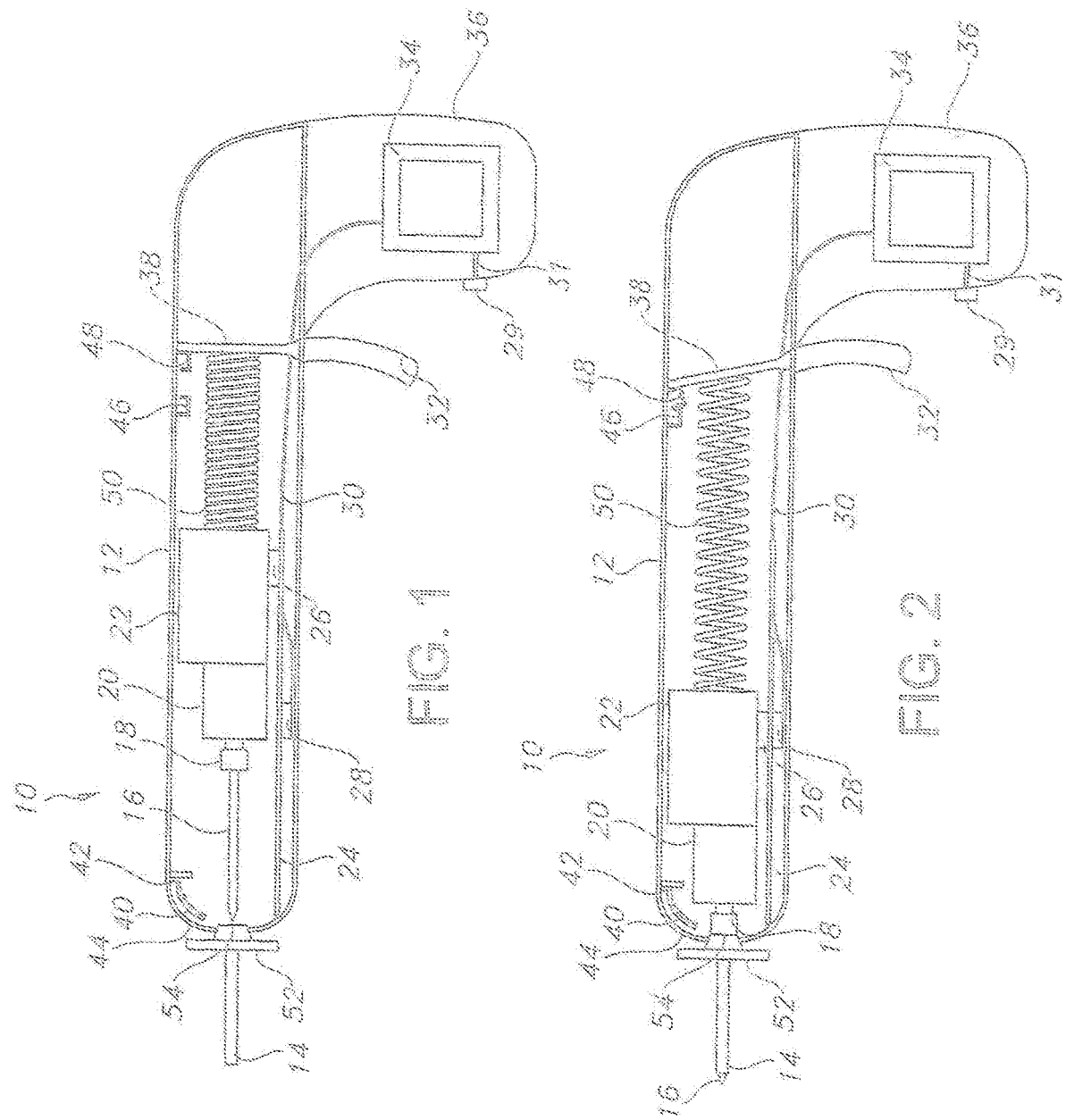

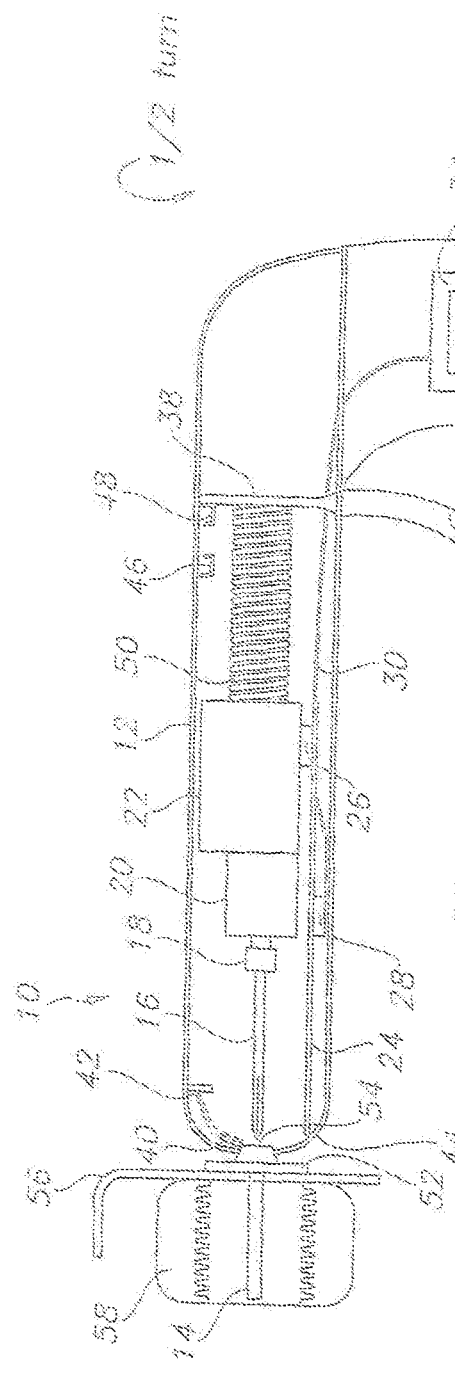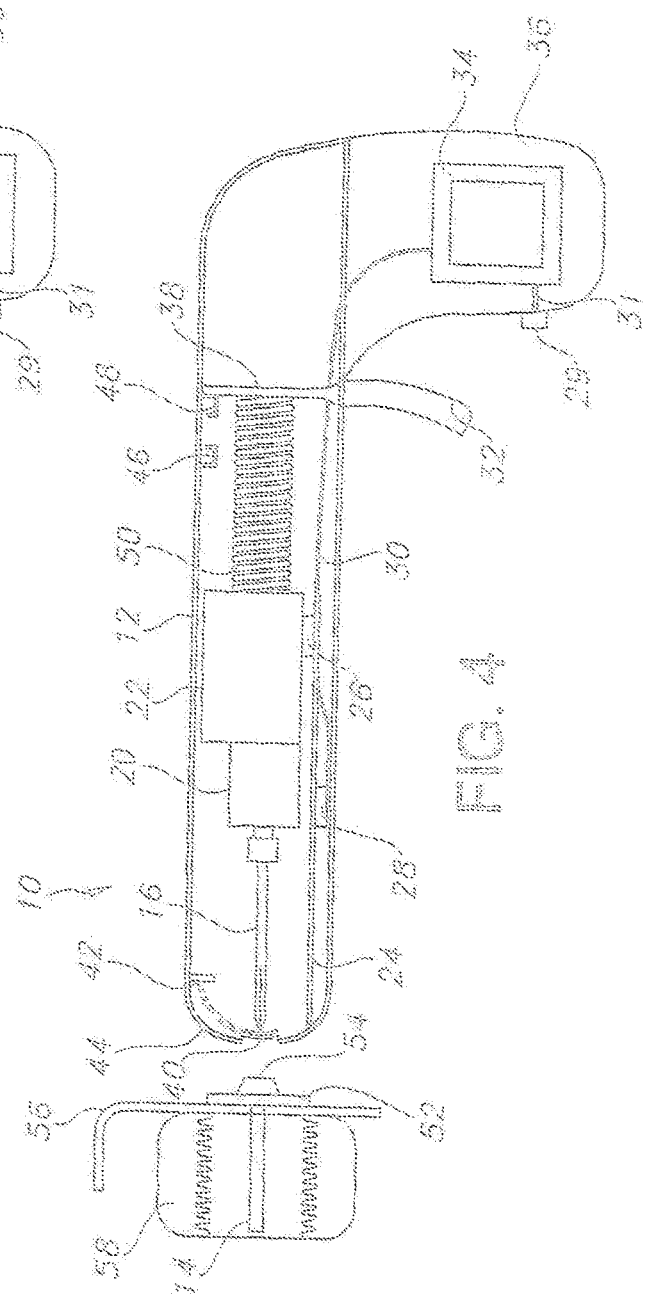

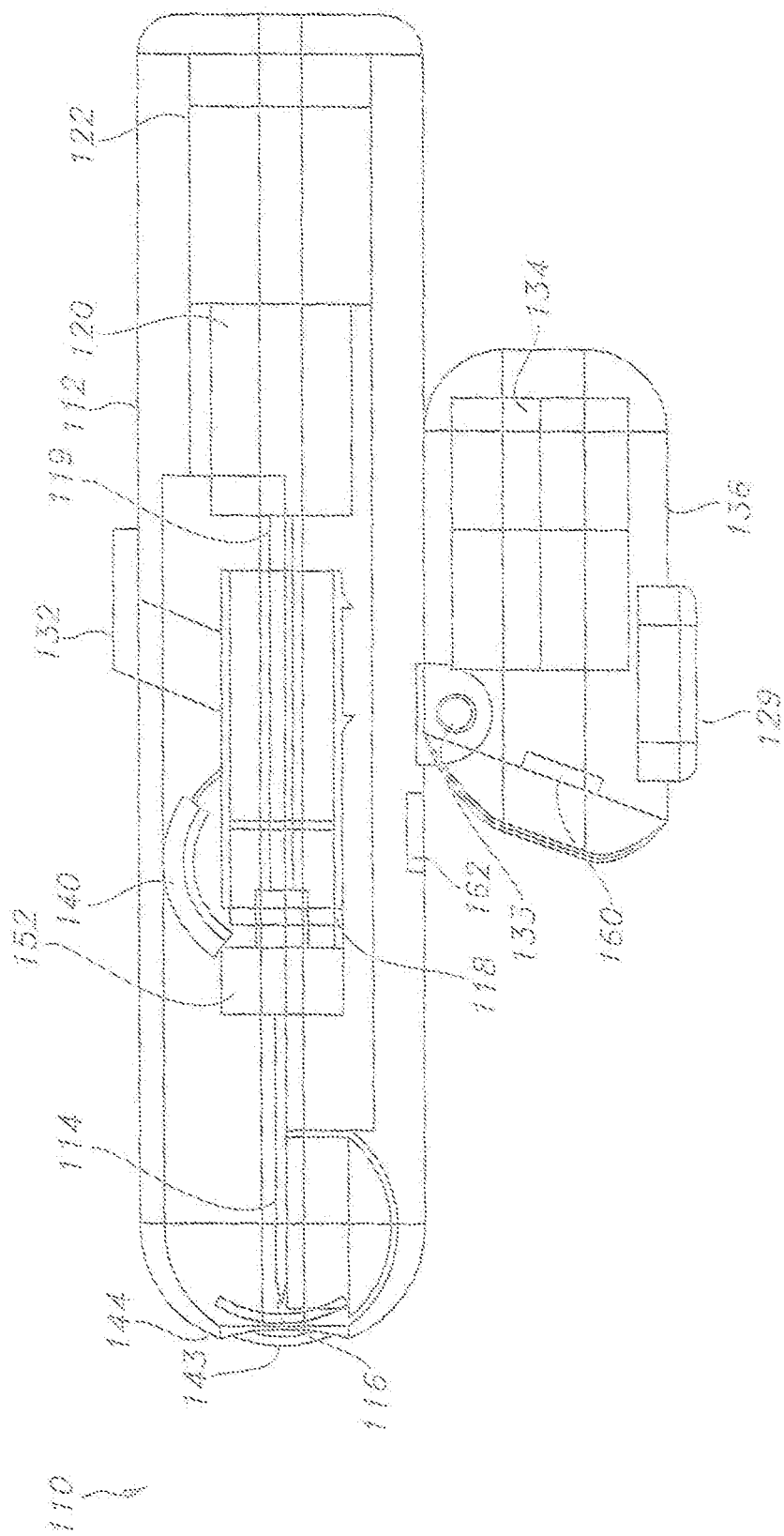

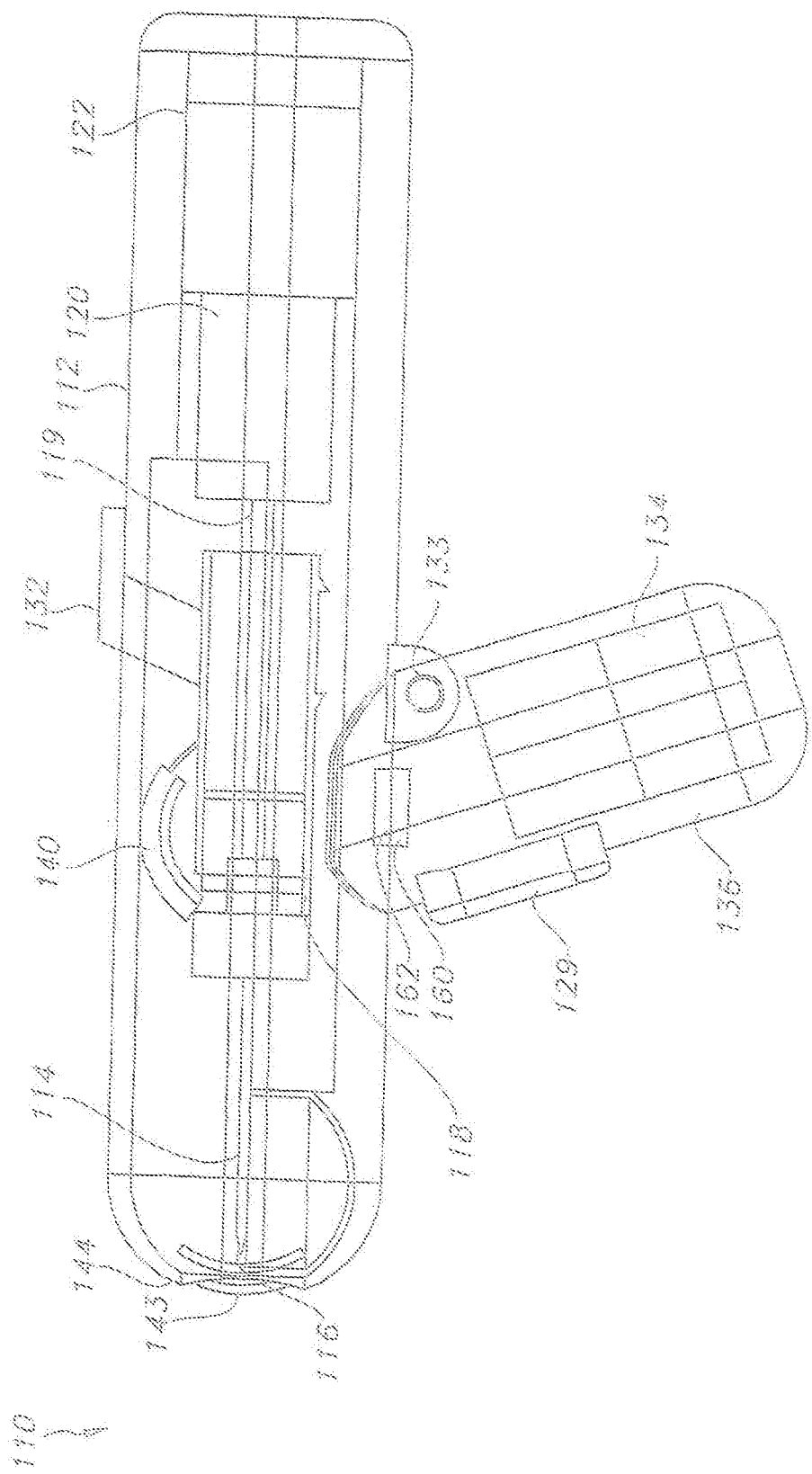

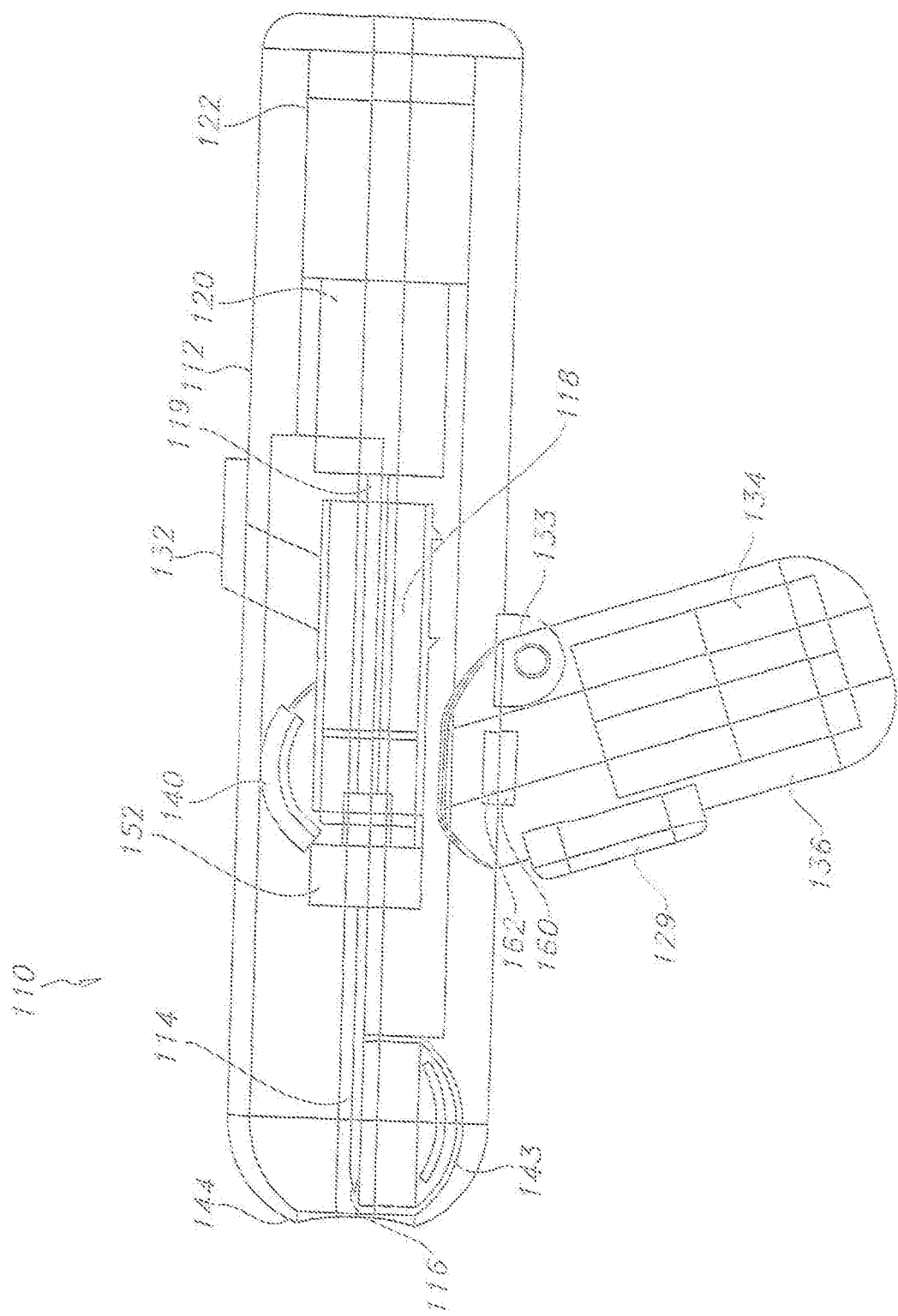

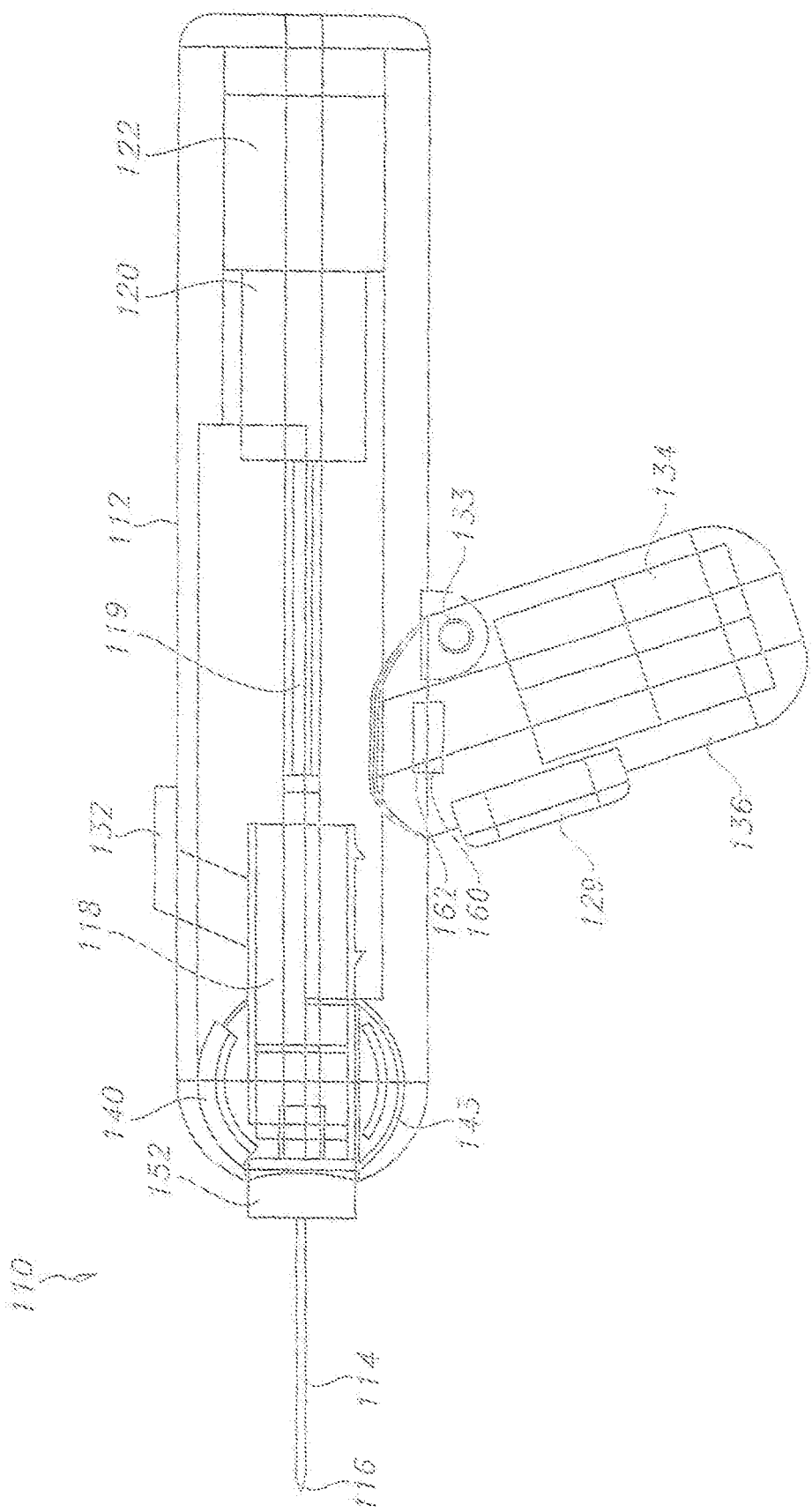

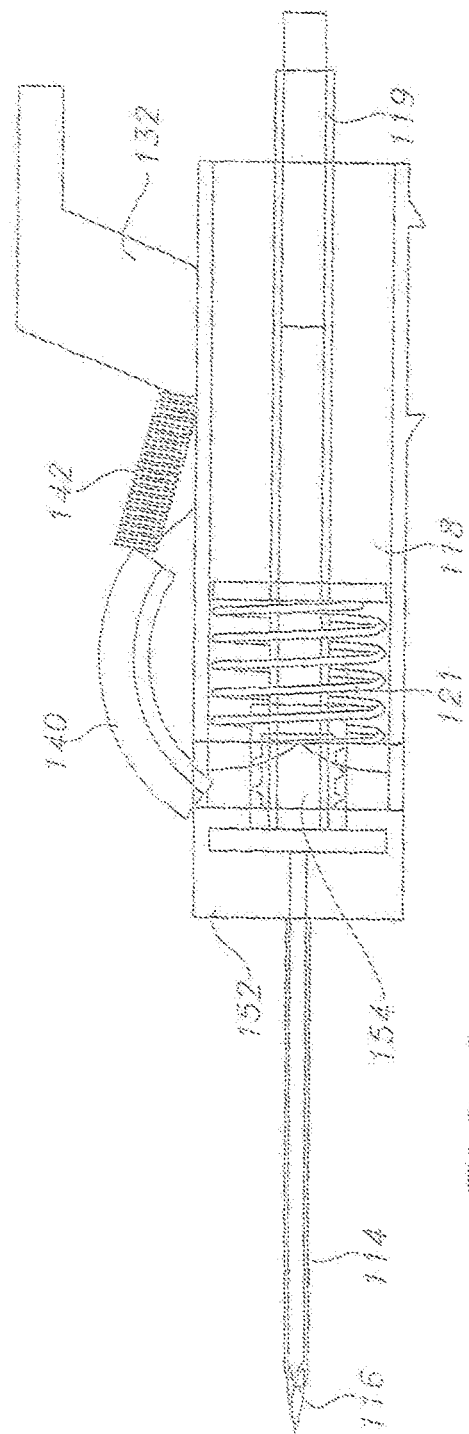
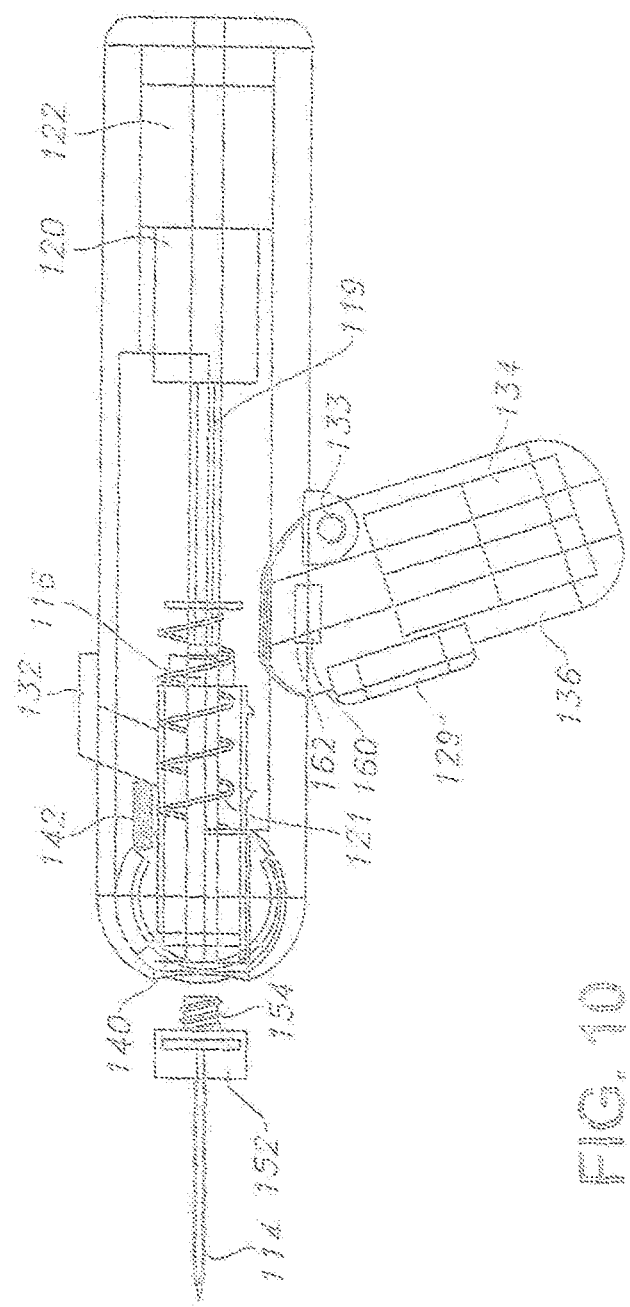

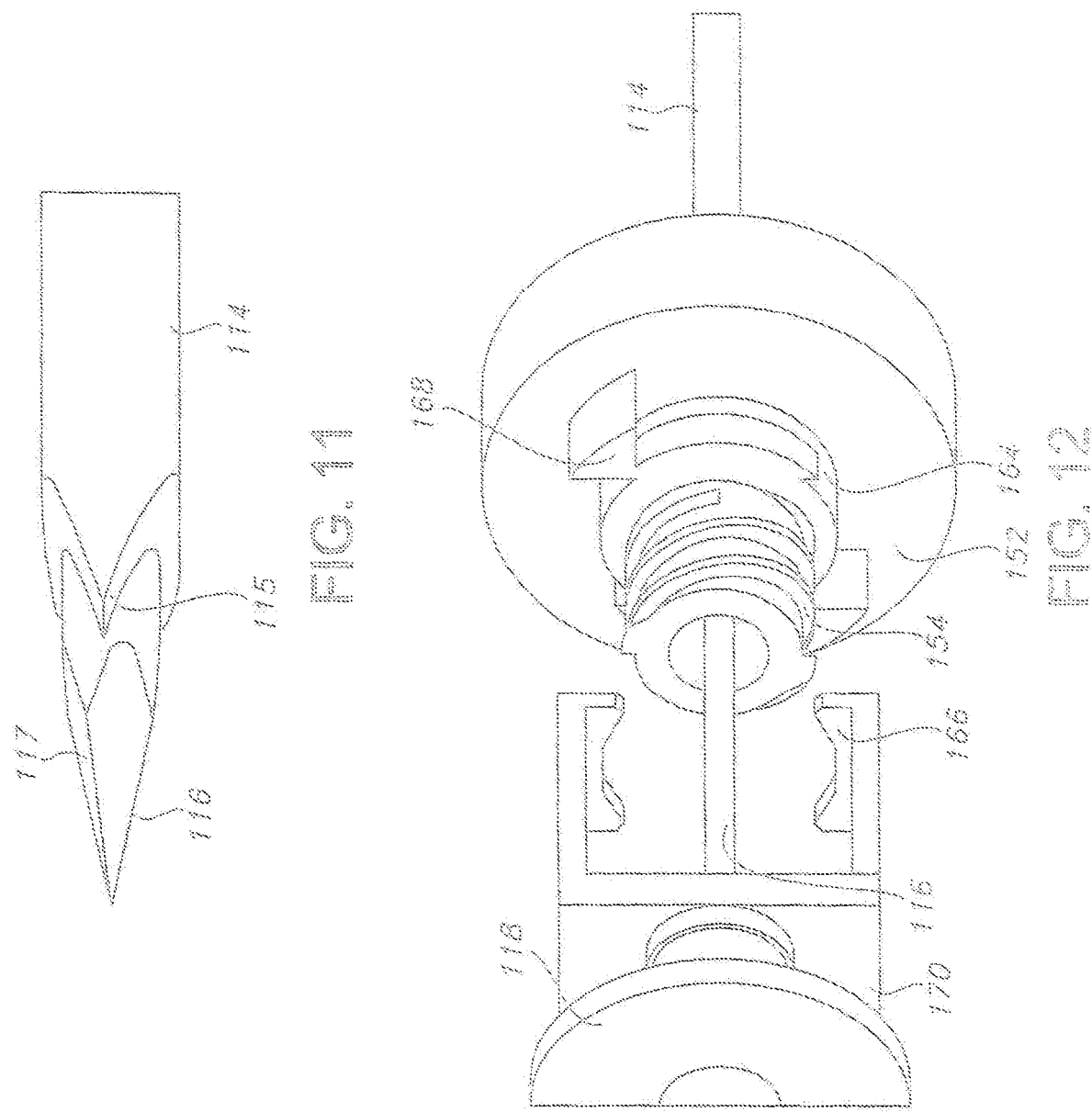

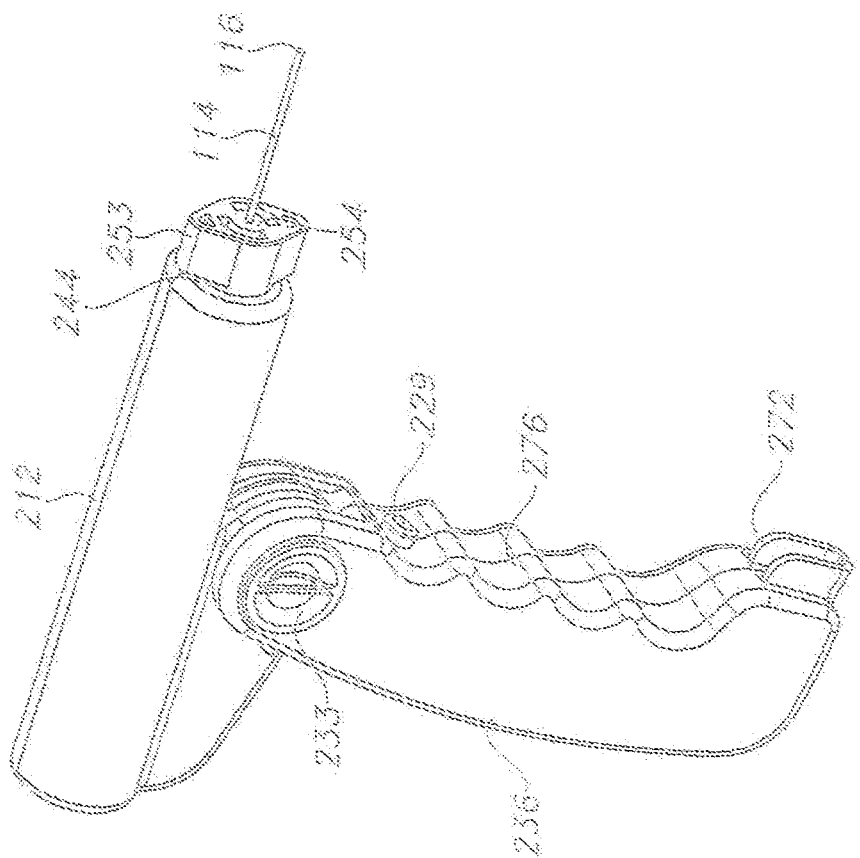
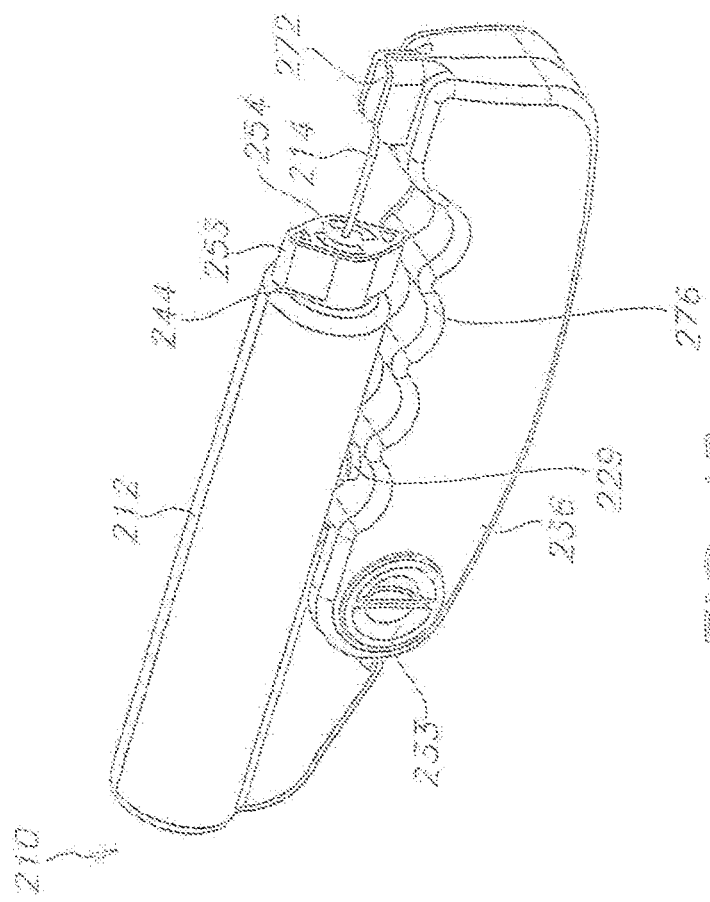

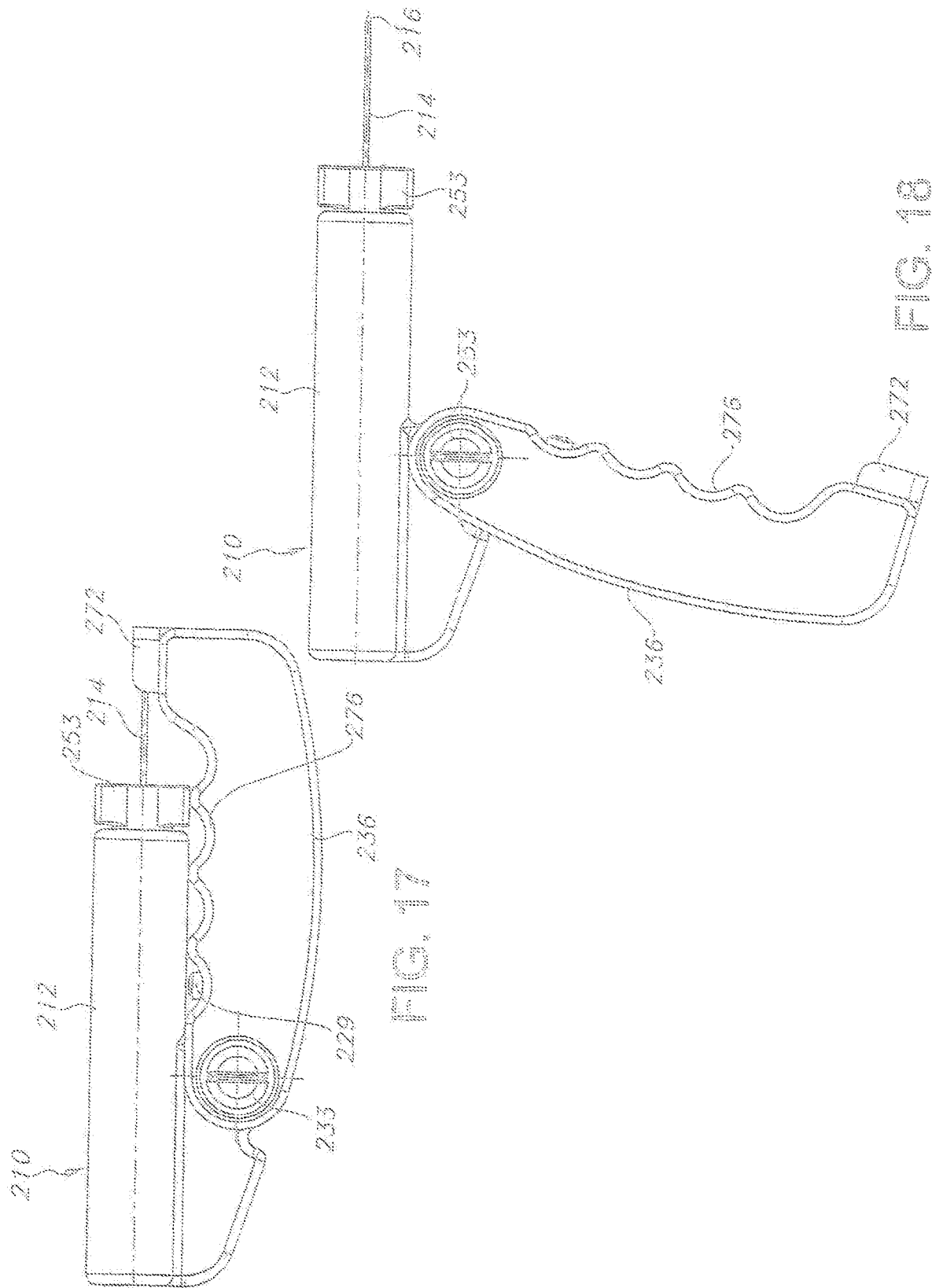

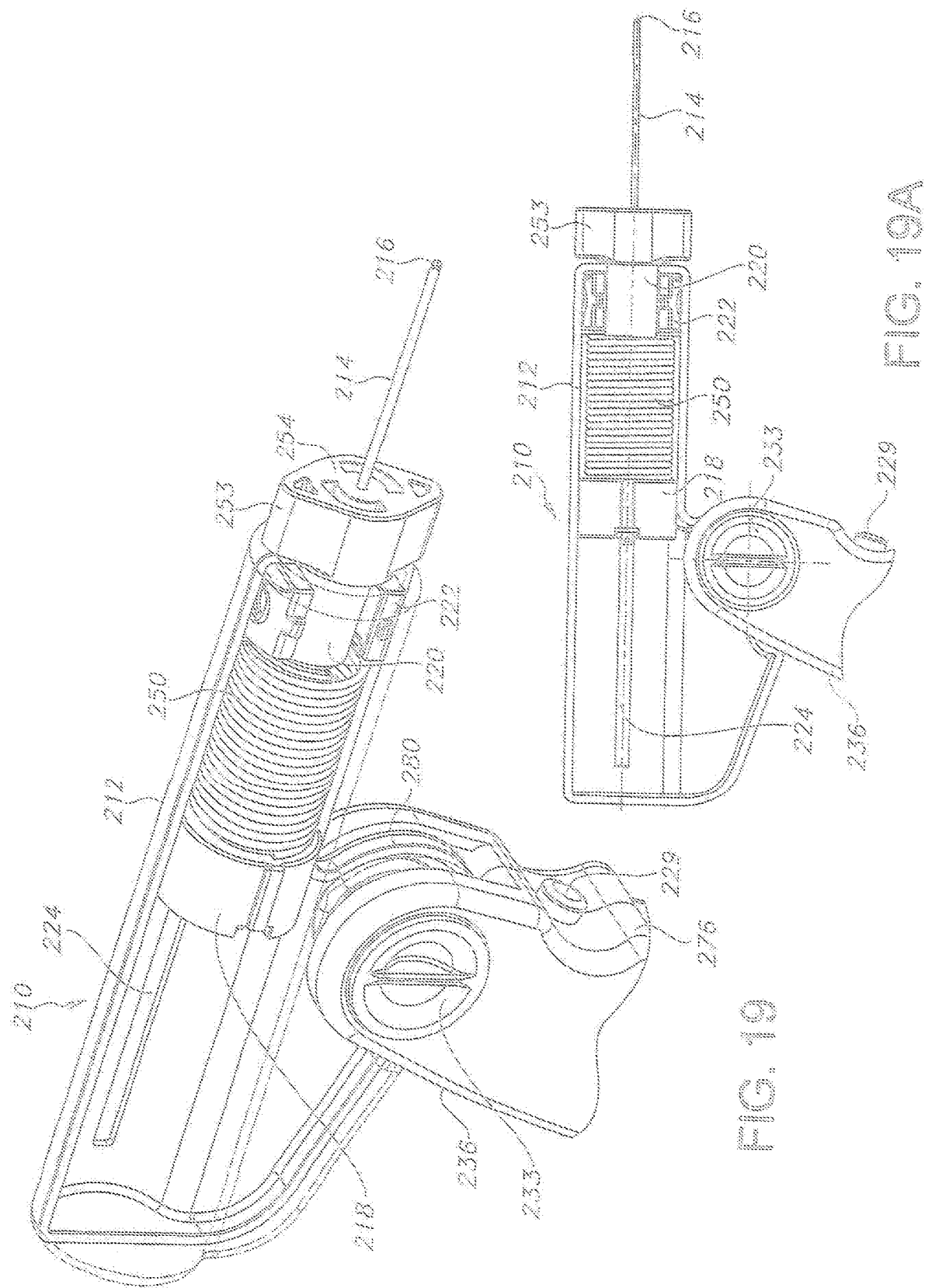

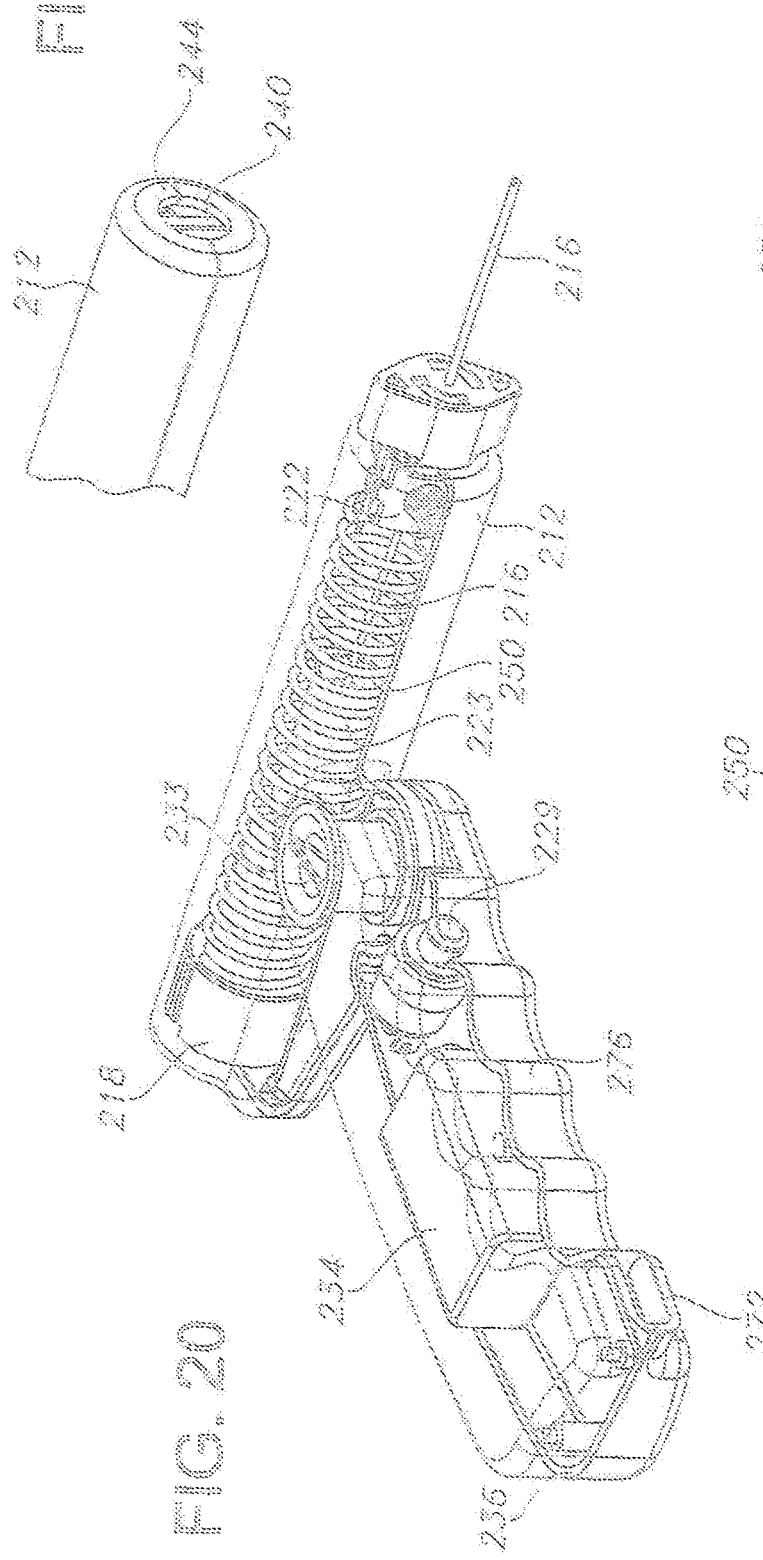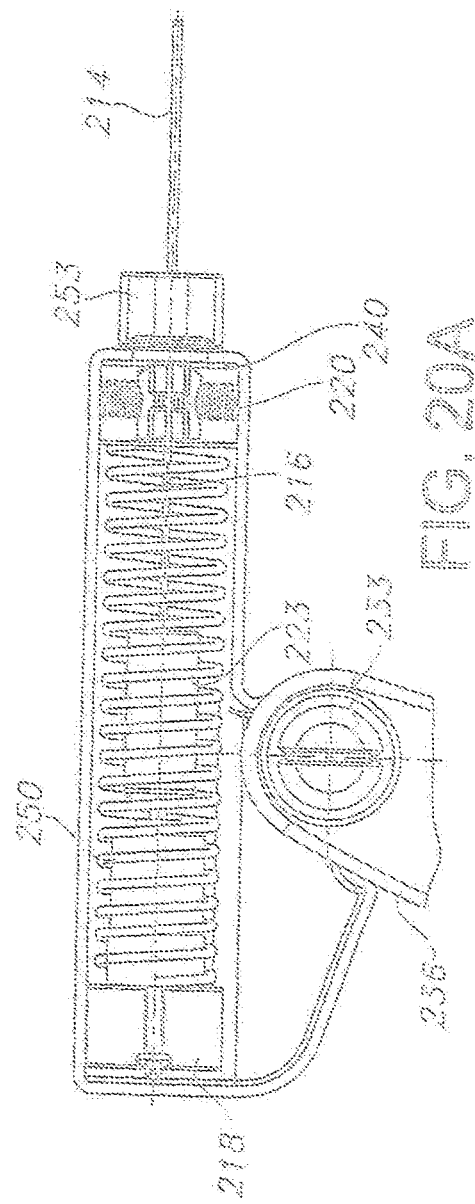

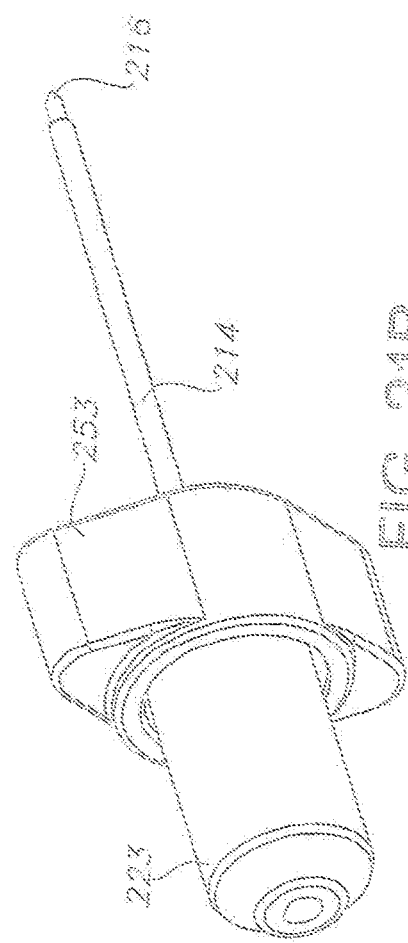
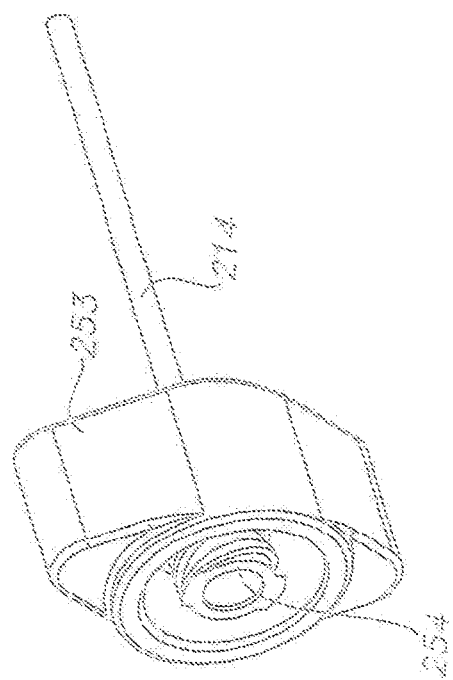
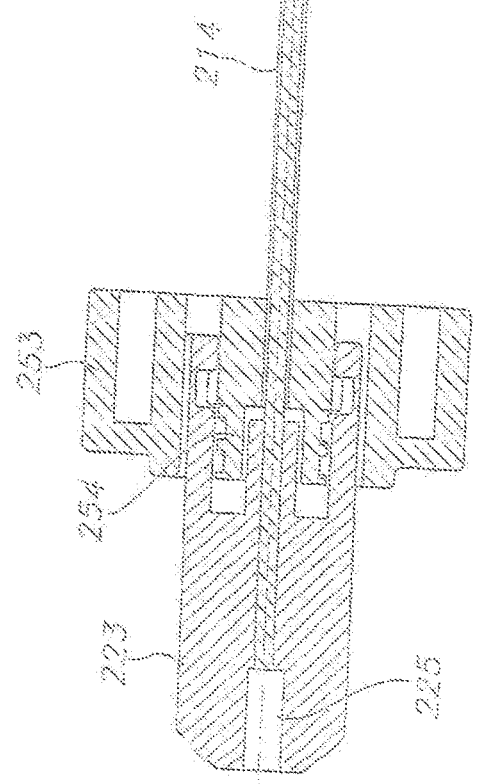

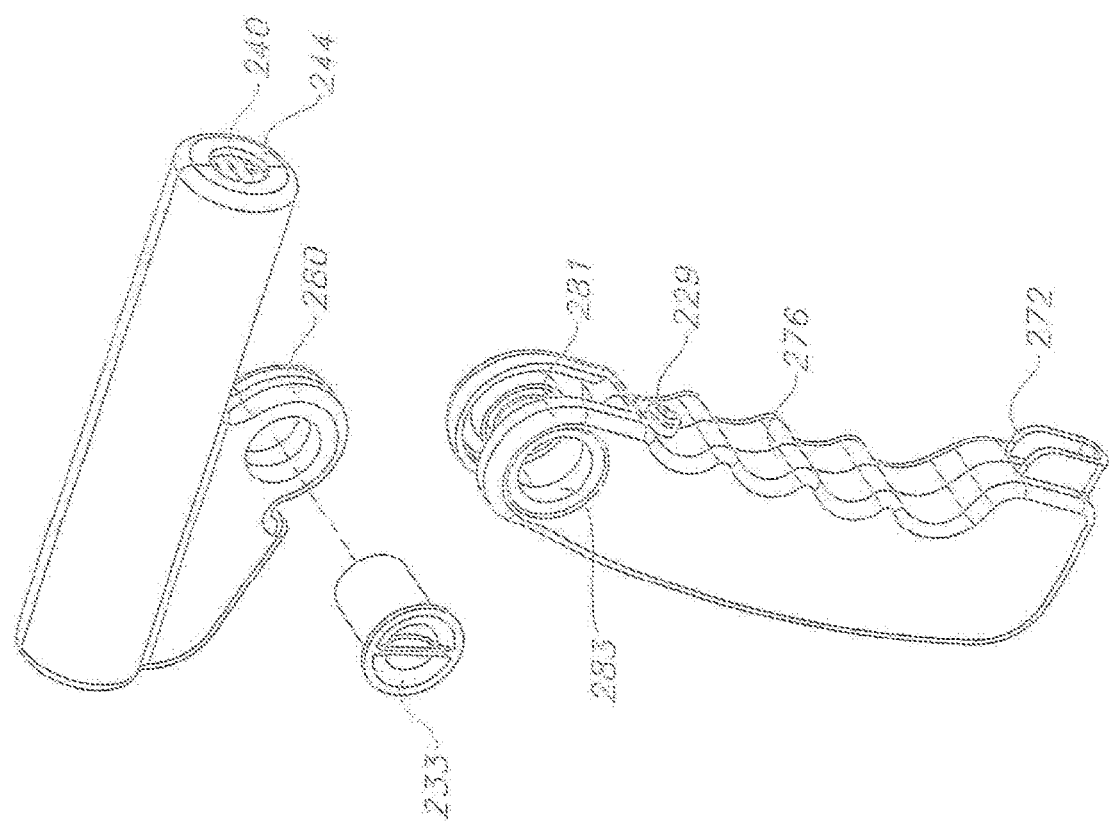

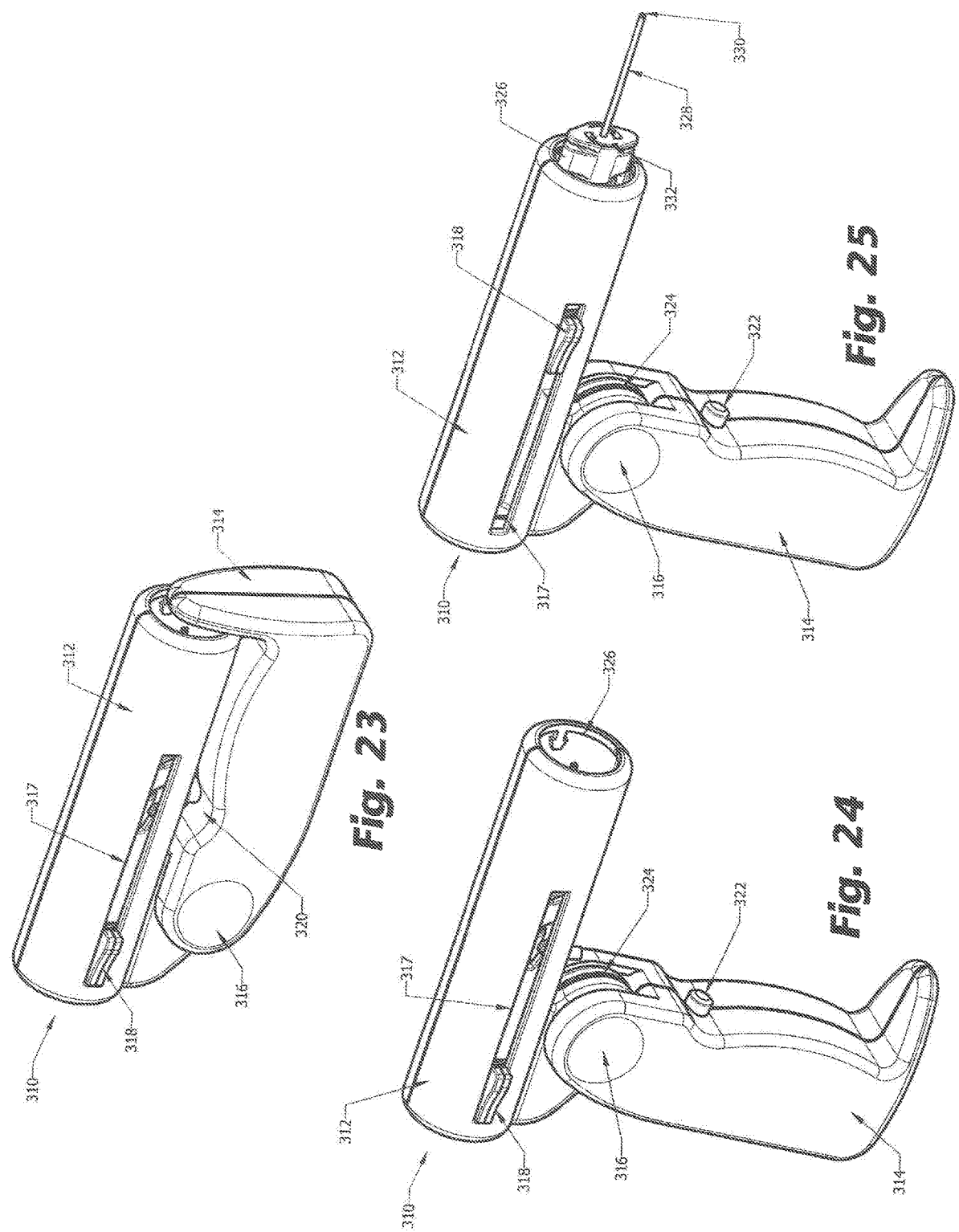

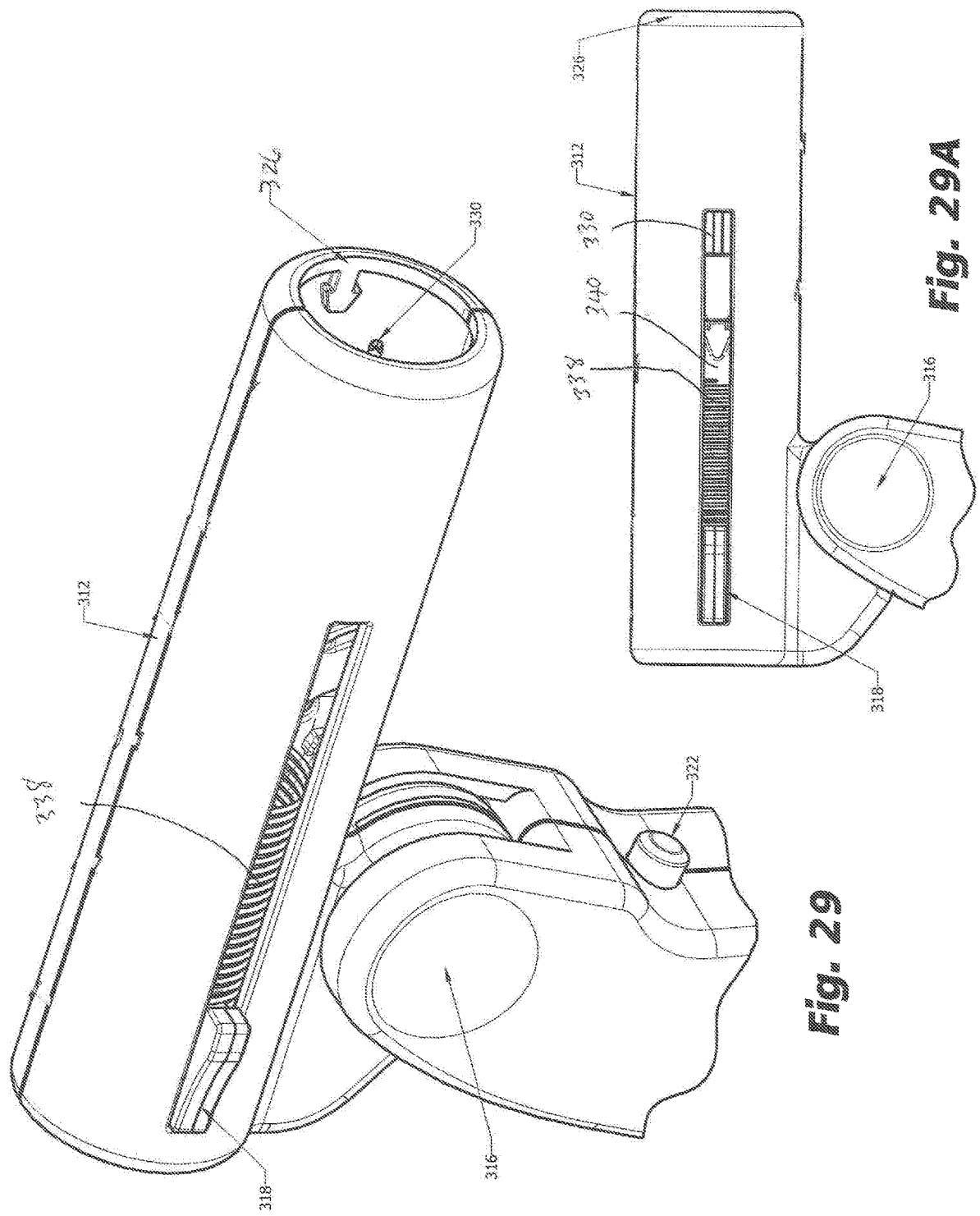

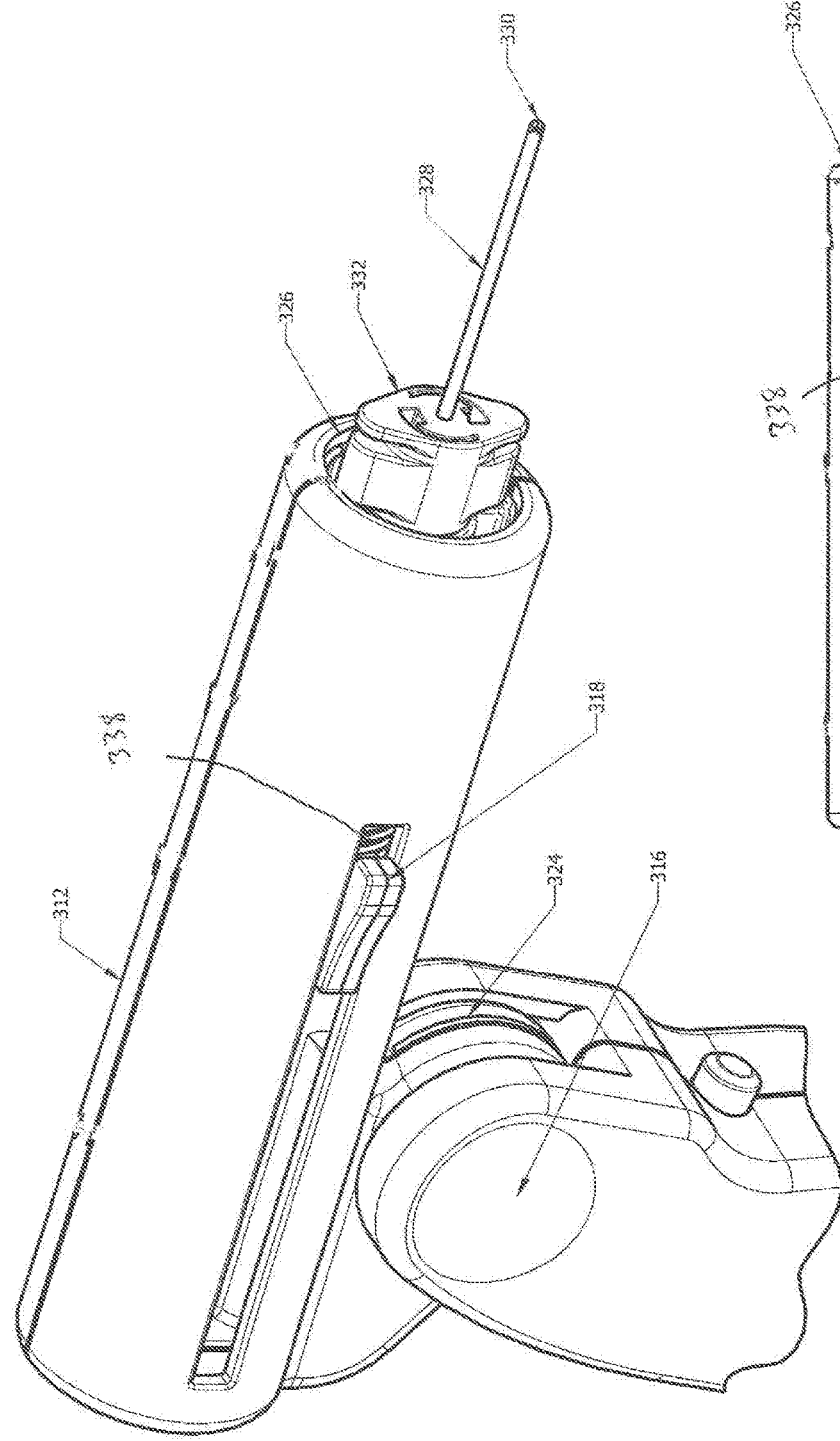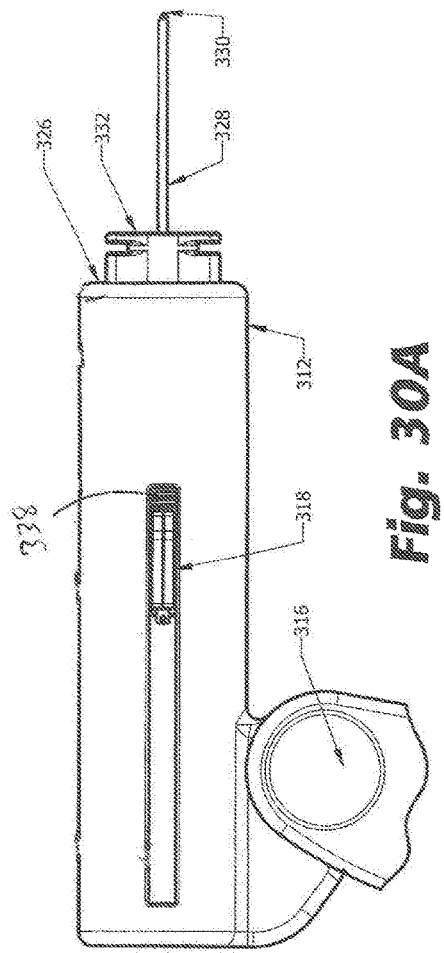

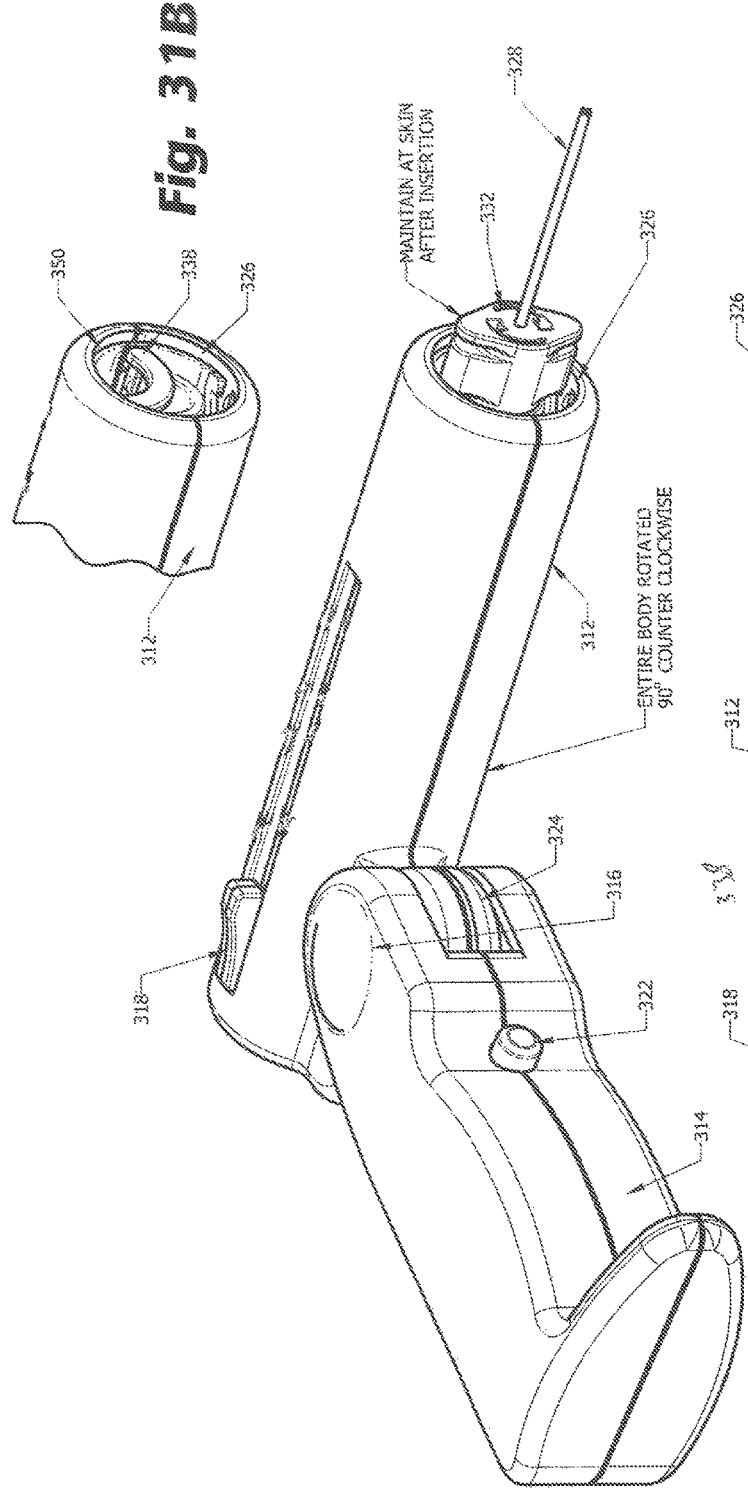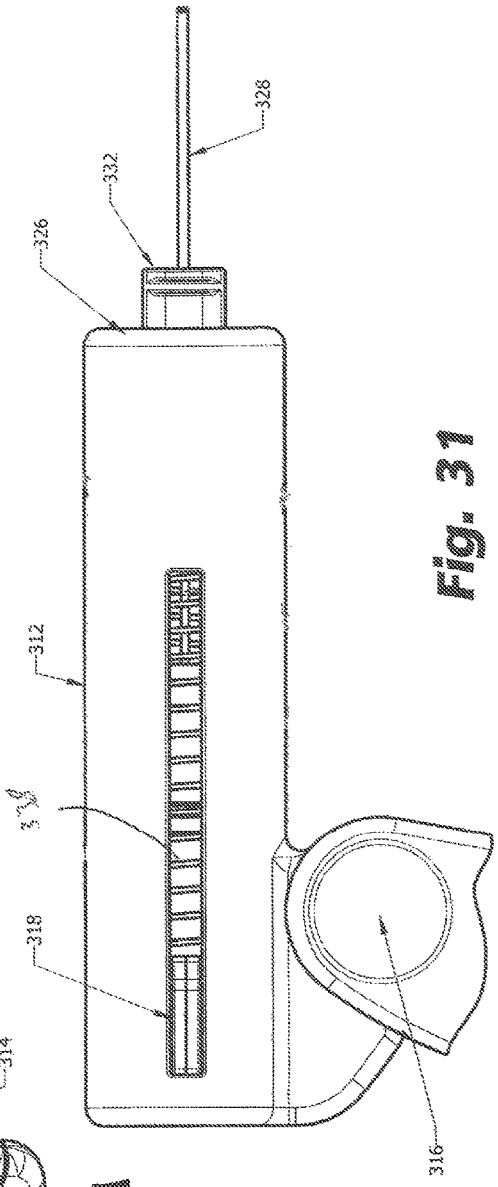

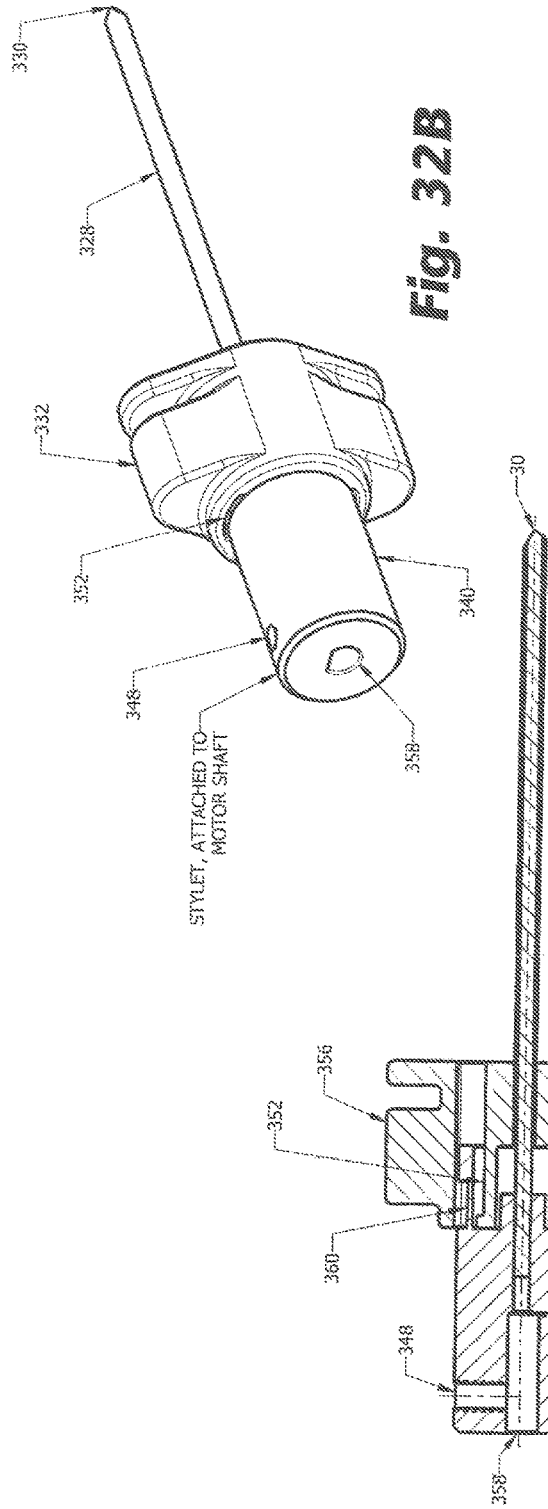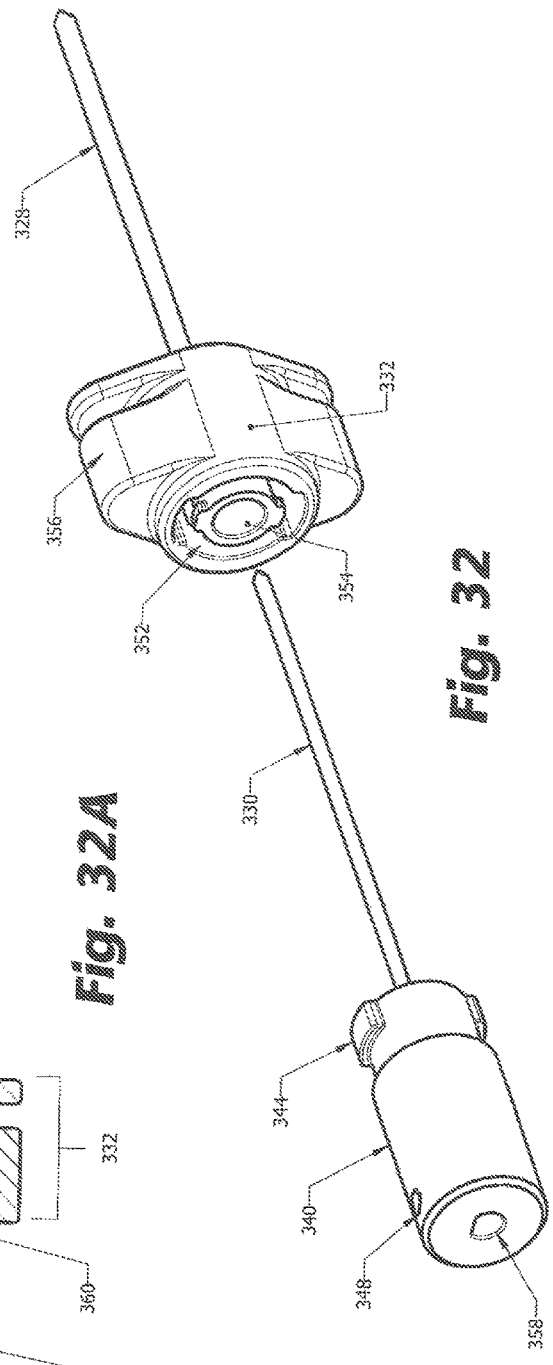

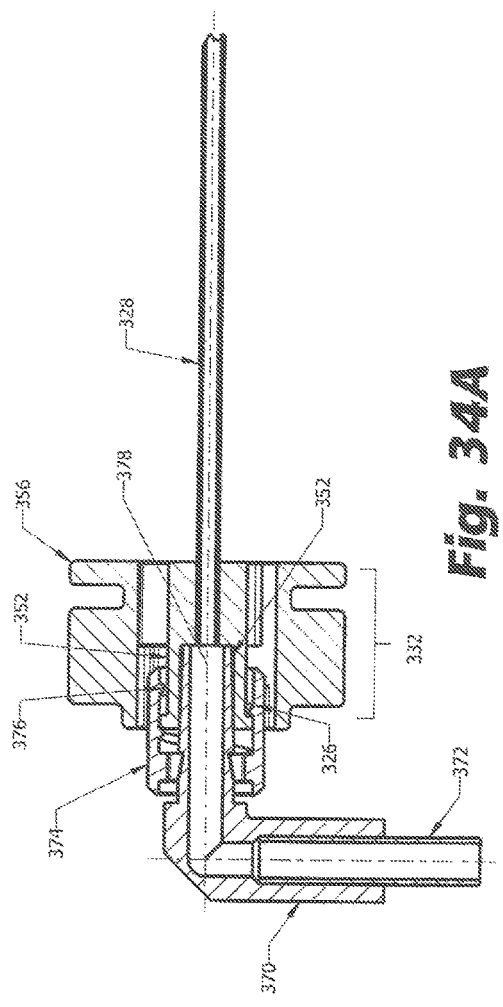
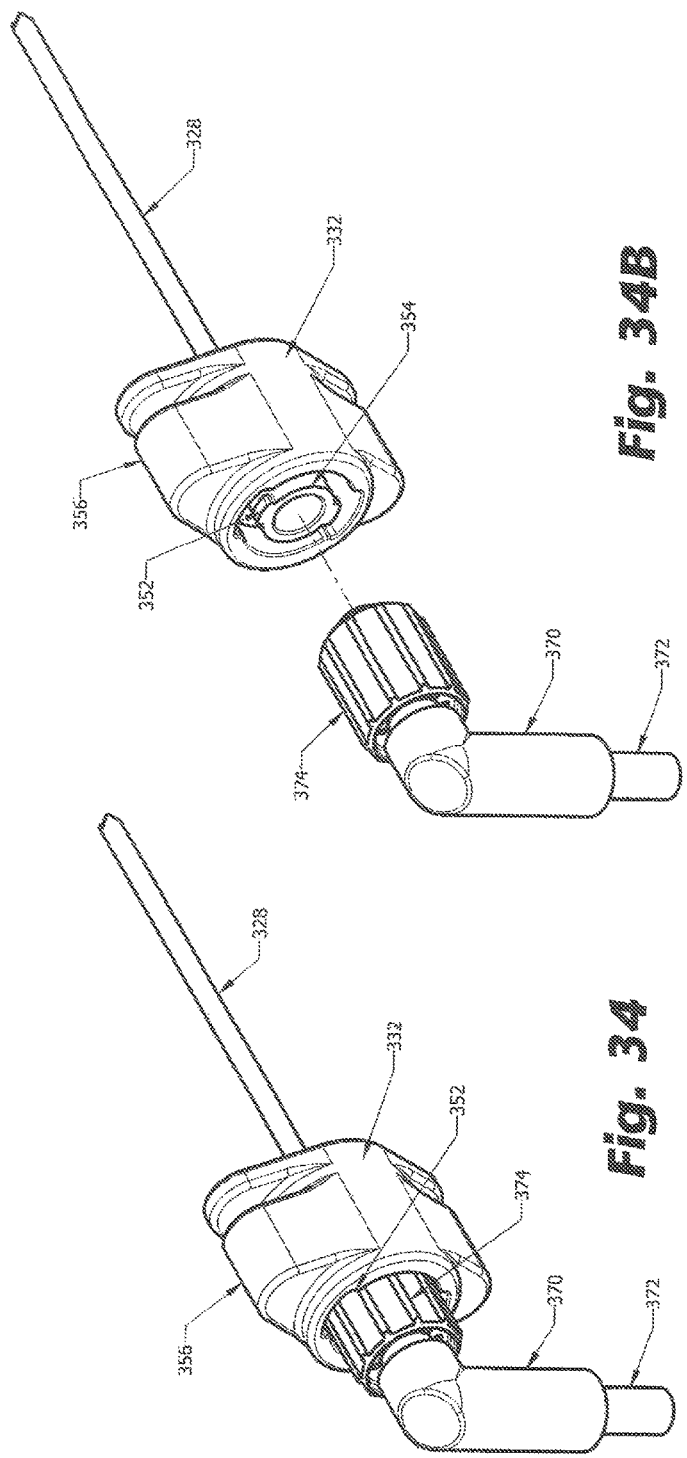
Fig. 34A
Fig. 34B
Fig. 34

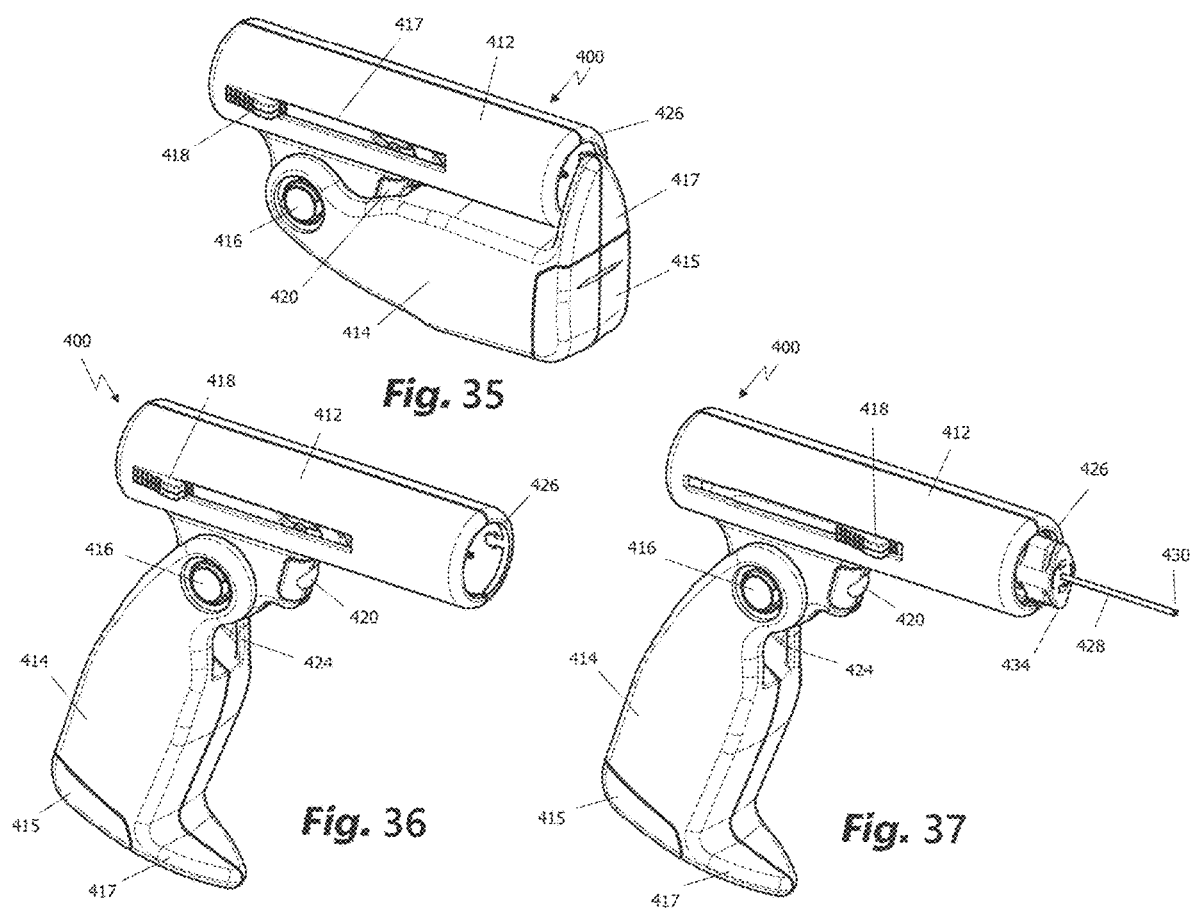

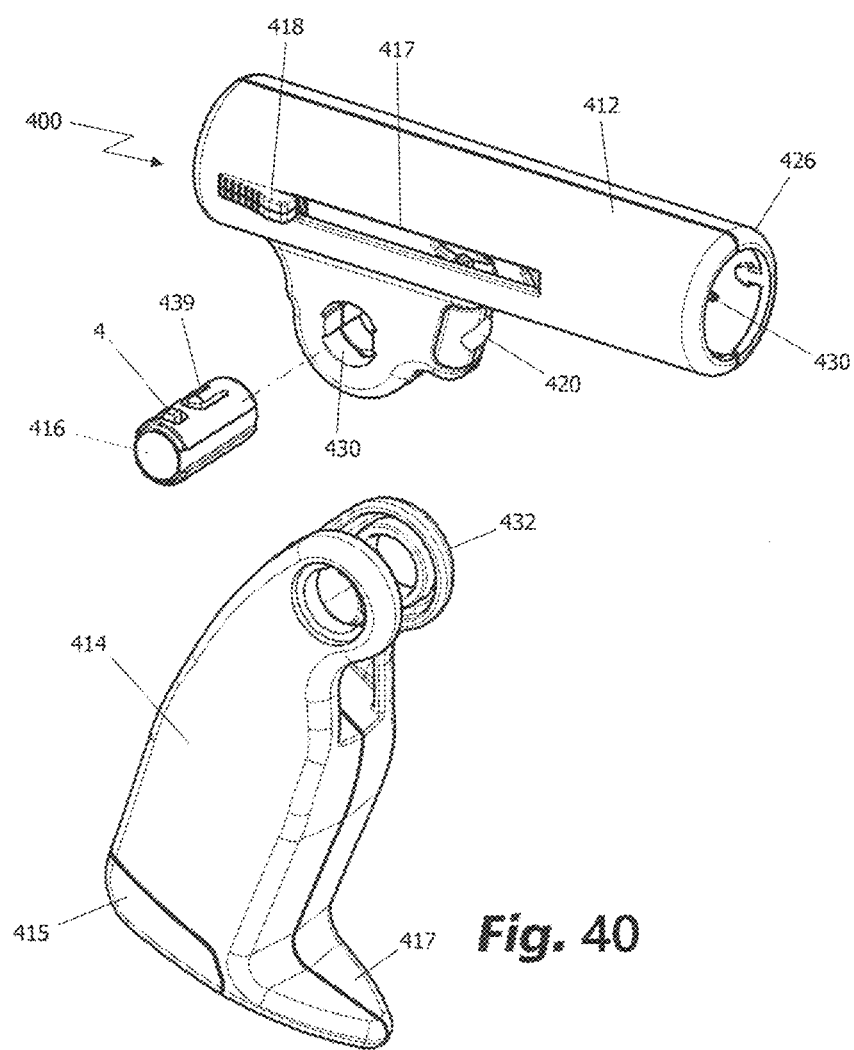

HANDLE CLOSED

HANDLE OPEN

SECTION A-A

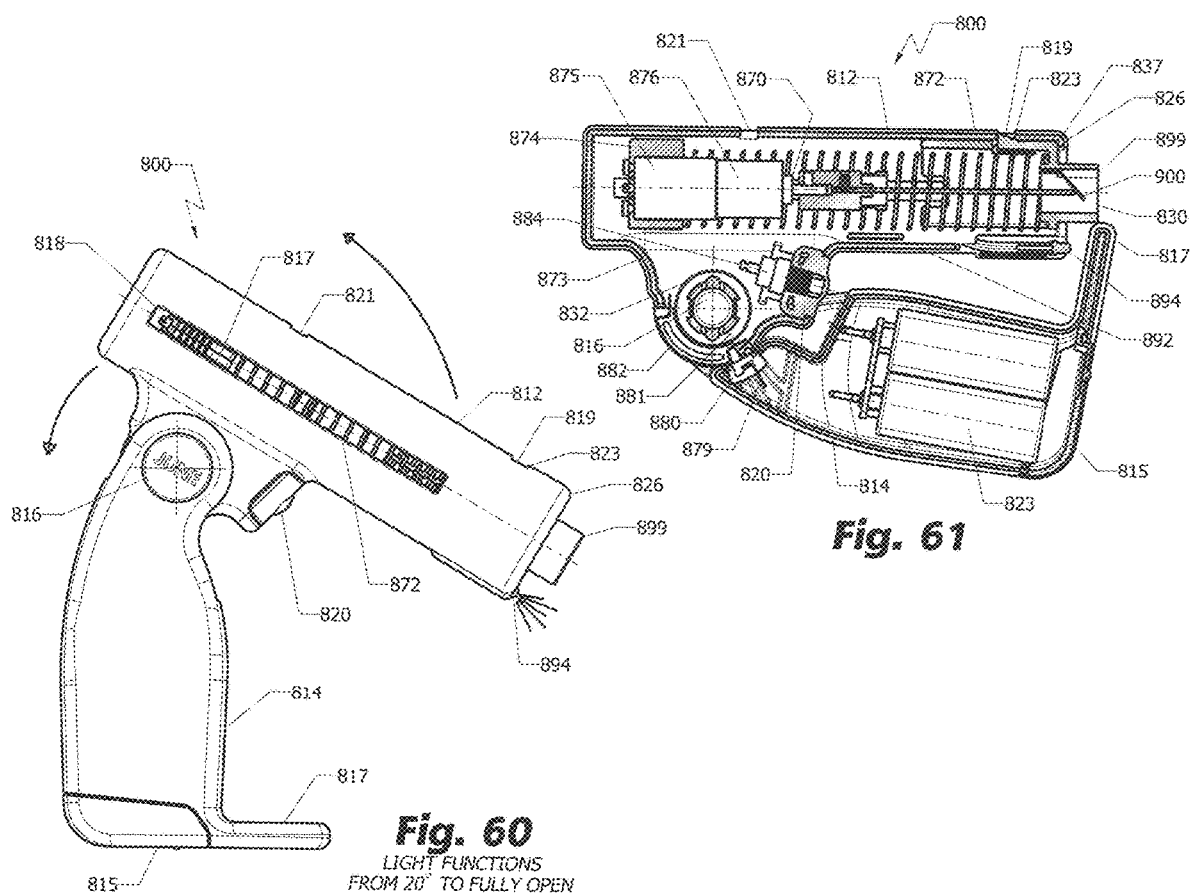

PASSIVE SAFETY INTRAOSSEOUS DEVICE

CROSS-REFERENCE TO RELATED APPLICATIONS

This application is a continuation-in-part of U.S. patent application Ser. No. 16/125,767, filed on Sep. 10, 2018, which claims the benefit of U.S. Provisional Patent Application Nos. 62/556,337, filed on Sep. 9, 2017, and 62/566,498, filed on Oct. 1, 2017. The entirety of the parent application and both provisional applications are herein incorporated by reference.

FIELD OF THE INVENTION

The disclosure relates to a portable and passive safety intraosseous device to allow for direct introduction of medications, etc., within the intermedullary space of a subject patient's bone or, if needed, the removal of certain substances from such a subject patient's bone. Such a device permits direct drilling and placement of a cannula within the subject bone with access external to the subject patient's skin, permitting, as well, connection of a tube for such introduction/removal purposes. The ability to provide a passive safety unit allows for facilitated utilization in, for instance, emergency situations with the entire device provided for utilization thereof. The device includes a drilling component with a permanently attached stylet and a removable cannula, a power supply for a single drilling operation, a mechanism to draw the stylet back into the drill component after use and disengagement from the cannula, and an automatic closure that activates with the separation of the cannula.

BACKGROUND OF THE INVENTION

The ability to internally deliver fluids and/or medicaments to a patient for quick and effective resolution of certain medical problems has, of course, been the desire of the medical industry since its inception. Although intravenous delivery is a standard for certain situations, there are emergency instances that require a much more robust and safer procedure than first having access to an individual's arm or neck and then, in a potentially difficult position, undertaking venipuncture to provide such an IV line. One particularly effective alternative to such IV-based methods is intraosseous delivery, or the access to the intramedullary space of certain properly sized and located bones within a subject patient's body. For example, again, considering emergency situations in particular, there may occur the need to access a proper introductory space for a patient at an automobile accident site. Such a patient may be suffering from cardiac arrest or other type of malady at that moment requiring quick action to introduce necessary fluids/medicaments for treatment. With an IV-based procedure, again, if the patient is situated in a difficult position for such IV access, or at least in terms of access at a proper and suitable vein for such a purpose, the ability to provide such a necessary action may be compromised. Finding the vein, for instance, may be difficult and require multiple attempts by the emergency medical technician, incurring time that is of enormous necessity. Thus, there is an alternative that may provide more access points for such fluid/medicament delivery. Such intraosseous processes allow the paramedic, clinician, EMS personnel, etc. the ability to locate a suitable bone (whether in the arm, leg, knee, or even sternum) and then introduce a cannula therein for delivery of needed fluid/medicament within the intermedullary space thereof. Such a procedure has proven to be an effective alternative to IV methods on occasion, but in terms of emergency access situations, and the ability, at least, to introduce fluid/medicament within a bone that is close to, for instance, a patient's heart, is particularly effective and desired. Additionally, such an intraosseous method may also permit removal of, for example, blood plasma, bone marrow, and the like, in less stressful situations than emergencies. In any event, the versatility of such a device is particularly important and aids immeasurably within the medical industry as a result.

To date, there have been utilized certain intraosseous devices to different levels of effectiveness and versatility. Initially, the "standard" method employed was basically the manual screwing in of a cannula and stylet. Such a method is, clearly, dependent upon the abilities of the user to first determine the proper location for such an introduction and, more importantly, the need to properly gauge the depth of such a drilling/screwing stylet component to enter the subject patient's bone. Guides may be provided at the skin surface for some degree of control and depth determinations, but the ability to properly operate and apply such a manual device has not proven effective and/or desirous in developed nations. Certainly, though, the ability to provide some type of manual intraosseous device in other countries that lack access to battery, etc., powered devices leaves the usefulness of such a device to the capabilities of the actual user and whether s/he can control and direct such a screw-type implement correctly. Relative speed of introduction is likewise then a potential drawback of this type of device.

Other devices, such as spring-loaded ballistic types have also been employed within the industry. Such gun-like delivery devices are, frankly, limited in their benefits to the industry simply because the user must properly hold and aim such a device while it basically shoots a cannula device through a subject patient's skin and into his or her bone. The user must align everything properly, hope that the cocked device does not prematurely shoot the sharp cannula component, and then keep the device in place while shooting a sharp dart-like implement into the desired bone. Such a method has proven highly suspect at the emergency use level, primarily because of the difficulties in keeping the alignment, etc., in place correctly and, more importantly, the lack of control of the depth of introduction within the subject bone. If employed with certain target bones, such a "shot" dart may crack certain bones, potentially causing potential problems such as leakage of intramedullary fluids or, more importantly, introduction within the bone of undesirable substances (not to mention significant pain for the subject patient, too). Additionally, such a device may misfire, hitting undesired locations, may dislodge from a patient's bone readily particularly when the stylet is removed, or even fail to penetrate the target bone. As such, the drawbacks of this type of intraosseous device are prevalent.

Another device utilized currently includes a separate drill component that magnetically attaches to a stylet (trochar)/cannula implement. Whether utilizing this magnetic drill option or the projecting type, the stylet/cannula combination has proven to be highly effective due to the ability of the stylet to generate the primary bone entry results (drilling or shooting) with a proper tapered end while being removable from the cannula thereafter. This configuration allows for the stylet to drill, shoot, penetrate, etc., while preventing bone, skin, and fluid from clogging the cannula upon removal therefrom. It thus also allows the cannula to be of a suitable bore to provide optimum injection (drip) into or removal from the subject bone intermedullary space. In other words, the combination of stylet and cannula has proven to be important and highly desirable for intraosseous utilization.

Thus, with the magnetically attached stylet/cannula device, such is then placed at a location external of a subject patient and aligned with a location for a suitable bone and then the drill is activated to introduce the stylet therein. After drilling, the stylet is detached from the drill (which is then used for future drilling procedures) and then unscrewed from the cannula, leaving an access port for fluid, etc., introduction therein through the recessed cannula, fluid, etc., and/or removal from the same port. To accommodate different bone sizes and/or different size subject patients (adults as compared with young children and/or infants, for instance), this system includes two differently sized stylet/cannula implements (color coded as well), one at 45 millimeters and the other at 25 millimeters in length (with 15 millimeters for pediatric usage). The cannula includes an external circular lip to prevent further introduction within the subject patient's skin and bone and a further separator may be placed prior to drilling to further limit the depth of introduction, as well (one may be placed after drilling, too, to best ensure the cannyula remains in place). Such a system has proven effective in certain situations, particularly with hospital-based, non-emergency instances due to the control aspects involved and the ability to capture and easily dispose of the stylet post-drilling. There are, however, significant drawbacks with such devices and procedures, namely the requirement for effective control prior to skin introduction; instances have occurred where the user attempts to set the stylet properly at the skin surface only to lose control and impale or at least scar the subject patient, even in non-emergency situations. Also, the necessity of handling the extremely sharp stylet has proven difficult and hazardous, particularly after detachment from the cannula and most particularly in emergency situations. As such an implement must be disposed of immediately, for obvious reasons, the potential for the user to harm the patient of her- or him-self is exacerbated with a free stylet in such an instance. Likewise, then, the dependence upon the drill component itself to be fully charged for use, if not also provided and/or found easily for such a purpose, is of significance as well. The separate provision of a drill in this type of situation, coupled with the determination of proper length stylet/cannula, locating such proper length stylet/cannula, attaching same to the drill, and then drilling with all in place without harming the subject patient, is of consequence within this particular area of the medical industry.

Of further importance, if not the highest importance, however, is that whether in terms of the projectile or magnetically attached drill type (or any other types within the prior art, including spring-loaded drills, sternum-applied drilling stylet/cannula implements, etc.) there is always an issue related to the potential for contamination of the stylet and high potential for contact with a user, patient, or other bystander during utilization. In other words, and as examples, with the standard projectile and magnetically attached stylet/cannula drill devices, there is a requirement of the user to physically detach the used stylet from the cannula and remove the same with the drilling/shooting tip exposed thereafter without proper coverage. The only possible means to prevent contamination appears to be the potential provision of a cushion-like implement to insert the stylet tapered end into after such use. However, in any situation typically provided as of today, the lack of automatic coverage and requirement of active removal with such exposure, no matter how prolonged it may be, leaves too much of a chance for transfer of contamination. As such, there remains a need for a truly passive safety protocol that is nonexistent within the intraosseous device market today.

Furthermore, with the reusable drill implement of the magnetically attached stylet/cannula method and device, such a drill is potentially contaminated after each use. Additionally, in emergency situations, such a magnetically attached device requires the actual locating of, unpacking of, and applying (attaching) of such a stylet/cannula implement to a potentially previously contaminated and potentially questionable power level for sufficient operation, such that clear difficulties in utilization thereof exist. There thus exists a significant need to provide an intraosseous device and system that overcomes all of these clear deficiencies. To date, however, the separate drill with detachable stylet/cannula has been the standard, leaving much to be desired, particularly as an emergency medical tool and specifically in terms of a passive safety protocol.

ADVANTAGES AND BRIEF SUMMARY OF THE INVENTION

A distinct advantage of the versatile apparatus now disclosed is the provision of a drill with stylet/cannula implement that exhibits total passive safety to avoid any potential exposure to contaminated components subsequent to application of the cannula within a target patient's bone. Another advantage includes the ability to provide a potentially disposable drill/stylet combination that accords the ability to have the entirety of the device provided as a single portable structure, thus eliminating the need to locate separate component parts prior to utilization and simplified disposal of the same. Another advantage is the ability to provide a drill component that has a proper shape that allows for facilitated manual operation for stylet/cannula introduction if needed. Yet another advantage is the ability of the stylet to be retracted back within the drill subsequent to drilling completion and detachment from the cannula. Still another advantage of the overall device and system is the potential for a sensor to determine the exact moment of entry within the intermedullary space of a subject bone, thus eliminating the possibility of such a device from entering such a space too far or not far enough, maximizing the amount of space such a device permits fluid introduction and/or removal from the subject bone. Another advantage is the ability to store the device without any electrical contacts and thus the ability to conserve battery power until utilized, with the potential, as well, to remove any such batteries easily after use for disposal thereof and placement of the remaining device portions within a proper disposal container associated with bodily fluid, and the like, contacted articles. Yet another advantage is the ability to manually activate the device for electrical connection and subsequent movement of an internally stored permanently attached stylet and combined removable needle. Still another advantage is the provision of a recessed hub on the needle with an recessed lock between the drill-attached stylet and needle. Yet another advantage is the facilitation of utilization from transport to disposal, including easily transporting such a device in a pocket or bag, removing it in total, unwrapping from a sealed package, flipping open the device with one hand, manually moving the motor/stylet/cannula sled for external access, operating the drill component to introduce the style/cannula within a subject patient's bone, upon completion, turning the device a quarter (or other degree) turn dislodging and retracting the motor/stylet back into the device with an automatic cover over the stylet point, subsequently dismantling the device for placement in a sharps container and otherwise disposal of the remainder. Still another advantage of a potential embodiment is the ability to provide a light within the device for visibity purposes as well as a possible indicator of proper electrical connections upon engagement between the handle and barrel. Still another advantage is a potential embodiment wherein the handle portion of the device is configured to stand upright on its own and with the barrel attached and manipulated to any angle of rotation around the handle/barrel connector, and the ability of the light (or lights) to remain in operation as the device stands on its own and with the barrel rotated to different angles. Yet another advantage is the potential embodiment of the provision of a protective cap within the barrel over the motor/stylet/cannula that also functions as a extension externally to allow for sufficient space for a user to effectively grasp the cannula hub as it has penetrated a subject patient's skin and bone, and that remains extended subsequent to motor/stylet retraction as a manner of preventing full closure of the device handle back to its original stored position. Still another advantage is a potential embodiment including a protective cap with an extending tab that correlates with openings within the barrel of the device to both serve as an indicator of location of the cap (prior to and after device utilization) as well as a detent to prevent retraction of the cap upon activation of the retraction operation for the motor/stylet.

Accordingly, the inventive intraosseous device comprises a disposable drill/stylet combination, wherein said drill includes a stylet retraction port therein, a retracting mechanism attached to said stylet and disposed within said drill, and a cannula connected in detachable relation to said stylet, wherein said stylet is permanently attached to said drill, wherein said retracting mechanism operates subsequent to utilization of said drill to introduce said stylet and cannula within the intermedullary space of a subject bone, said retracting mechanism moving said stylet from an external location to said stylet retraction port within said drill subsequent to a drilling operation, and wherein said cannula is attached to said drill with a Luer lock component with a lip portion present external to said drill and an automatic closure internally within said drill that activates upon disengagement of said cannula from said drill. The external lip of the cannula also provides, if needed, a surface for a user to grab while maneuvering the drill. Also encompassed herein is the inclusion of a sensor on said stylet, wherein said sensor measures pressure subsequent to bone entry such that once passed through to said intermedullary space the pressure difference deactivates the drill and activates the retraction mechanism and detaching from said cannula. The method of utilization of such a device (with or without the sensor as described) is also encompassed herein wherein the cannula as retained within the bone and skin and accessing said intermedullary space of the subject bone allows for introduction or removal of fluid, etc., therein.

Alternatively, the overall device may be provided with an internal movable combination of a stylet and cannula that are not directly connected, but are co-connected through a rotatable base. In such a configuration, the stylet may, for instance, be integrated within such a base in that it may be permanently affixed thereto and aligned with the opening shaft of the cannula so as to egress out of the top with the tapered end available for drill purposes. The cannula may then be attached to such a base through an two or more outer arm extensions from the base that include flanges that insert and turn within complementary structures on the base of the cannula in order to allow simultaneously for temporary attachment (and detachment through turning of the internal drill device base a specific distance after drilling has been completed) and rotation of the cannula in concert with the stylet. The movable nature allows for a stationed motor and gear box within the housing of the drill device with the extendible stylet/cannula combination arranged to retain gear association with the motor and gear box (to permit such rotation for drilling results) while allowing as well for retraction of the stylet once drilling has been effectuated. In addition, an internal seal (or door) may be provided initially to ensure the internal stylet and cannula are protected from contamination prior to use; if so, such a door may be configured to move and thus open to provide an egress point through the distal end of the drill device for the stylet/cannula combination to exit for drilling to commence. At the same time, an opposing door/seal component may be primed upon such extension in order to automatically close upon retraction of the stylet after use and/or upon detachment of the cannula from the internal extendible base (and thus from the drill device itself). In this manner, the passive safety necessity is provided in an alternative manner but still as effective, if not more effective, than the prior disclosure above. The user merely activates the internal base extension to open the drill egress point for the stylet/cannula to exit, activate the motor to effectuate the gear box and extended gear shaft to rotate the stylet and cannula simultaneously for drilling within a target patient's skin and bone until entering the target intermedullary space thereof, stopping such a drilling action, rotating the drill a slight turn to disengage the cannula from the base, at which point the stylet and internal base return automatically within the drill device and the primed door/seal closes automatically as well, leaving only the cannula with its Luer lock end available for attachment with an IV line or like implement as needed for fluid, etc., introduction or material, etc., removal from the target intermedullary bone space. If further desired, the user may include the application of a disinfectant on the Luer lock tip to further ensure contamination is not an issue.

The disclosed device may alternatively include a cannula with a hub for IV or other connection/insertion (again, for medicament, drug, fluid, etc., delivery within a subject patient's bone) that itself utilizes a novel recessed attachment point, rather than an extended Luer lock tip. Such a recessed configuration would allow for stylet temporary engagement during operation of the intraosseous mechanical automated drill motor, would facilitate disengagement through device (and thus retained stylet) rotation subsequent to insertion/penetration within such a patient's target bone, and further would allow for the IV, etc., placement and connection. Such a recessed configuration would ostensibly prevent undesirable contact, accidentally or otherwise, externally that could harm the patient and/or cause dislodgement or damage to the IV, etc., connection itself. In other words, standard Luer lock configurations extend outwardly from a standard cannula hub, requiring the IV, etc., connection at a point a measured distance external from the hub itself. Such a distance has been known to be rather susceptible to contact with surfaces and objects through patient movement, at least. As a result, there has been a rather important, yet unmet, need within the industry to supply a suitable structure to accommodate such needed modifications. The typical IV, etc., lines are actually configured themselves with a bend at the Luer lock tip to allow for the connection with the extended attachment point (for reliable connection), thus providing a transfer line that may exhibit problematic pressure differentials, even possible clogging, at the bend itself. In any event, although a recessed hub configuration as disclosed herein may still utilize a bent IV, etc., line for such a purpose, it has been realized that a direct line may be employed as the connection at the recessed portion allows for any type of connection to be in place in reliable fashion. As it is, the ability to provide greater versatility and protection from unwanted external contacts allowed with such a recessed cannula hub are at least a few unexpected results of such an improved structural aspect of the overall disclosure. Additionally, however, such a recessed cannula hub allows for, again, a reliable stylet interface for effective high-speed rotation while engaged for proper bone drilling from the stylet-integrated motor.

Furthermore, as it concerns the recessed cannula hub, such a component of the overall intraosseous device disclosed herein accords the user a suitable structure to grasp prior to, during, and/or subsequent to drilling of a target bone to allow for effective directional placement and ultimate retraction rotation of the drilling device in relation to the cannula component. Basically, a user may need to ensure proper placement prior to drilling and the cannula hub allows for such manual manipulation at the cannula location. During drilling, the ability to assure the direction of the drill is retained, and subsequent thereto, to allow for the device to rotate in the opposite direction, such as a quarter turn, as one non-limiting example, and thus ensuring the cannula does not also rotate with the device, all require the accessibility of the hub to the user to keep the hub and thus cannula substantially still. The hub also may be provided with other accessories attached thereto to aid, in one non-limiting example, with adhering the cannula in place on a target patient's skin while inserted within such a person's bone. To that end, the recessed cannula hub, which may, preferably, at least, itself be drilled to be flush with the target patient's skin, include opposing wing flaps with, again, as merely one non-limiting example, a living (or like) hinge at or near the external edge of the cannula hub, thereby allowing the same to fold downward and extend from the hub to the patient's skin. These wings may be of any geometric shape as long as they allow for such skin placement. Preferably such wings (or flaps) are roughly rectangular in shape and as unfolded on the patient's skin surface on either side of the surface-located cannula hub, provide structures that may be taped down to the target skin in order to further engage and secure the cannula (needle) within the target patient's bone. In other words, such juxtaposed wings (flaps) allow for an integrated structure within the recessed cannula hub to facilitate retention of the needle component within the target patient to percent unwanted movement from the set bone-insertion position, at least. The recessed cannula hub itself may be of any geometric shape itself, including circular, oval, square, rectangular, star-shaped, triangular, pentagonal, hexagonal, etc. Additionally, the dimensions are the recessed cannula hub may be of any permissible width (e.g., diameter) such as from 2-5 centimeters, preferably about 2 cm, and any permissible height (measured from a bottom edge to a top edge, with the bottom edge intended to be substantially flush with the target patient's skin) such as from 1.5-3.5 centimeters, preferably about 2 cm. The recessed cannula hub may also be provided in different colors to indicate the length of the needle (cannula) inserted within a target patient. This communication capability helps indicate to, for instance, hospital personnel the type of cannula (needle) in place as inserted by, again, for instance, an emergency medical technician at an accident site. In other words, the indication of the color of the recessed hub subsequent to insertion within a target patient's bone communicates such information directly to a nurse, doctor, etc., within a hospital setting, thus allowing for immediate recognition and understanding as to the length and possibly bore of the cannula needle in place at that moment. Such colors may refer to lengths such as, for instance, yellow pigment to indicate 45 mm needles, blue pigment for 25 mm needles, and fuchsia (or dark pink) pigment for 15 mm needles (and generally for infant patients). As it is, then, such a recessed cannula hub allows for unexpectedly effective benefits, as noted above, heretofore unexplored within the industry, let alone the intraosseous device industry.

A further possible embodiment of the disclosed system is the provision of a small profile device in folded disposition prior to utilization with the stylet/cannula component extended outside the drill body and covered in such a configuration. Upon need for use, the device may then be, if desired, easily disengaged from the folded configuration to allow for access of the stylet/cannula component for drilling within a subject patient bone with the unfolded other component being a handle with a grip, a switch (to activate and deactivate the drill assembly associated with the stylet/cannula), and a further configuration to properly direct and apply force for the stylet/cannula to be drilled within he subject patient bone. Such a configuration may be provided with the ability to accomplish such a result while using a single hand, as well, thus allowing for freedom of use of the caregiver's other hand for other needed actions and/or activities, particularly in an emergency situation. The caregiver may thus complete such an intraosseous drilling action and then either press a release button or rotate the device in relation to the now-implanted cannula to disengage from the cannula itself and force, through a retractable assembly, such as, in one possible embodiment, a spring device to return the stylet within the drill body. Additionally, the device may then, as above, cause, upon movement of the stylet component into and within the drill body, the closure of a door component to seal the drill body from the exterior environment. In such a manner, as above, the entire procedure is passive in terms of the safety aspects thereof. The caregiver/user simply opens the folded device, directs and drills the extended stylet/cannula component within the subject patient bone, releases the cannula from the drill body thereby causing the stylet component to retract into and within the drill body itself, and the automated sealing door closes at the exact moment the stylet moves from within the confines of the cannula (implanted within the subject patient bone) and within the confines of the drill body. Thus, again, as discussed above, such a possible embodiment provides total protection post-contact and insertion within a subject patient's body (and thus after contact with and potential infection by, bodily fluids and other possible substances associated with internal contact, at least; such also prevents any possible issues with contact with the subject patient's skin, as well, if necessary) through a guarantee that any contact with the stylet is prevented since each possible occurrence would only happen while within the confines of the cannula or the drill body. Upon disengagement from the cannula as it has been implanted, the stylet automatically retracts within the drill body; the automatic door closing sealing the drill body at the exact moment of stylet entry therein creates a barrier to contact with the used stylet, as well. In any event, such a further embodiment allows for further protections and even simpler handling and utilization thereof if desired. Furthermore, the ability to then capture the used stylet within the sealed drill body provides, as above, a means to dispose of the entire device without any contact with an infected portion.

As well, such a separate possible embodiment also allows for the handle component to house the power generator of the overall drill motor. With a proper revolving handle around a hinge, such a structure may allow for a simple manner of disengaging the handle after utilization thereby permitting the caregiver/user the ability to dispose of the sealed drill body separately from the powering handle component, thus allowing for facilitated disposal overall. Also, with the sealed drill body, such may be provided without any means to reopen such a component without damaging the entirety thereof, thus preventing any subsequent utilization thereof, or even attempts at utilization, thereby guaranteeing mistaken activities with such a used stylet in the future. Likewise, the handle may also be configured to disengage automatically upon cannula disengagement from the drill body, as well, again preventing any further attempts at utilizing a "spent" and possibly infected device.

To facilitate disposability of the overall device, as alluded to above, a separable handle and barrel are provided in one potential embodiment. In this way, the barrel would include the motor/stylet component with at least a partial cover to prevent any stylet point contact external the barrel after retraction. The barrel thus retains the "sharps" portion of the drill device and thus requires proper disposal in such a situation. Full "sharps' disposal of the entire device may be undertaken, thus allowing for barrel and handle disposed in such a manner together; however, such a possibility may be problematic as the weight of the device, as well as the volume thereof, may be too great for efficient "sharps" container placement for such a purpose. Thus, again, as noted above, the handle may be disengaged from the barrel to permit barrel "sharps" container placement and the handle disposed of in a different manner. A connecting hub component may be introduced within aligned circular openings of both the barrel and the handle to permit not only the rotational capability (for efficient storage and transport, as well as easy unfolding for full access as needed for intraosseous drilling), but also a connection peg that can be removed to allow for the disengagement of all three components simultaneously, while still providing a stable and resilient means for rotational movement of the barrel in relation to the handle (or vice-versa). With such a potential embodiment of a connecting hub in place, then, the handle and barrel may be easily disengaged for disposal purposes (as well as the connecting hub itself). The handle (and the connecting hub) may then be disposed of as needed, whether within a standard refuse container or bag (or other type of implement) or within a biohazard container, particularly if blood or other bodily fluid contacts such a handle during or after utilization. In any event, the ability to provide such a versatile disposal capability, particularly as it concerns the need for separate disposal activities for the barrel and handle themselves (with the further understanding that the connecting hub may be disposed of in the same manner as the handle component, of course, as a separable piece. As another potential embodiment, however, the connecting hub may also include a resilient connection to the handle or barrel, if desired, so as to remain attached to either component subsequent to separation. This alternative would reduce the number of pieces of disposable components for the user. The connecting hub may further simply be reintroduced within the circular opening of either barrel or handle during disposal thereof by the user, as well. The device may thus be presented with proper indicators for the user to as a reminder as to the need for such disposable of component parts. For instance, without any definitive limitation intended herein, the barrel may be provided with a red coloration as a "sharps" component, either in terms of an complete coloration or with stripes, wording such as "SHARPS" presented on the barrel itself. Likewise, the handle may be colored an appropriate design to remind the user of the need for such a disposal (whether a different red, yellow, green, etc., with complete colorations wording directed to "refuse" or "biohazard", with stripes, dots, etc., basically any type of design that distinguishes from the barrel and communicates the disposable nature of the handle to the user.). The connecting hub may also include such an indication along the same lines for reminder purposes, as well.

The utilization and presence of a power generating component, such as, in one potential embodiment, a battery or plurality of batteries, further necessitates a consideration of disposability separately from the handle and barrel (and connection hub) under certain regulatory requirements. For instance, such batteries (whether lithium, alkaline, nickel-cadmium, lithium ion, and the like, preferably, potentially, at least, lithium in format for performance, cost, and disposability purposes) are typically required under regulations to be recycled or otherwise disposed in specific ways once they are utilized as desired. In this instance, the utilization of batteries coupled with disposable components of such an intraosseous device requires removal of such batteries therefrom prior to disposal on the handle. To that end, the handle may include any number of different access portals for initial placement (securely) of such a battery or batteries within the handle to connect with contacts and thus wires (or other type of electrical conduits) to deliver the needed electrical charges for operation of the intraosseous automated drill on demand (as well as a light or lights if desired, as well). The access portal may be closed subsequent to contact and stowage of the battery or batteries, thus allowing for operation of the electrical drill upon unfolding and extension of the motor/stylet/cannula component as noted above. The battery or batteries can then be removed upon retraction of the motor/stylet subsequent to cannula/needle insertion within a target patient's bone through such access portal doors. Such a door may be disconnectable completely from the handle to permit such battery access and reconnectable thereafter such battery removal for a single handle component disposal action thereafter. The battery access portal door may also be configured with a living hings within the body of the handle to provide an integrated structure that remains as a piece of the handle for single-structure disposal above (like the connection hub alternative noted above). The living hinge may be provided within the rear portion of the handle, whether at the top, middle, or lower portion thereof, to allow for opening thereof on demand for battery removal purposes. Of potential preference in this situation is the utilization of two 9-volt lithium batteries provided within the handle (as a housing therefor) with, again, as alluded to above, proper snap connectors therein to permit suitable and proper electrical transfer from the battery to the device itself through wires. Such wires may be configured with a certain amount of room within the handle housing such that the opening of a lower portal door results in the batteries themselves to drop downward within the handle to permit access for such removal without any need of a separate implement. Alternatively, such a battery set may have a fabric or plastic ribbon draped over an downward around them to allow for removal, if needed, through grasp and pull of such a ribbon implement. In any event, the availability of certain living hinge battery removal doors allows for such disposability purposes and further retention of such a removal portal door for handle disposal thereafter as a single component.

The electrical connections within the handle include, again, the power generator (battery or batteries) with sufficient electrical strength to accord the necessary torque and speed for the motor/stylet/cannula combination to drill into and within a target patient's bone. Such a power generator may be, again, any type of battery (to allow for portability and utilization remotely) that provides such a benefit. Thus, for a particular potentially preferred embodiment, lithium batteries, particularly two 9-volts, may be utilized to generate the necessary power levels for the drill (and possible light or lights). Other battery types, including alkaline 9-volt, C, D, and possibly AA sizes (with a large number present for such higher power levels) may be employed in some circumstances, and may be utilized in consideration of the disposable nature of the overall device in line with the lithium batteries noted as preferred above (such lithium and alkaline batteries are lower cost than other rechargeable types, in other words, and simpler to recycle and/or dispose on demand; lithium batteries provide stronger performance levels for the needed torque and rpms for the drill, generally, and thus are, again, preferred). Thus, as alluded to previously, at least two 9-volt lithium batteries are potentially preferred due to shape, size, power generating capability for a short burst of energy with necessary torque and speed results, as well as ease in disposal. In any event, with such a battery source in position and properly connected through snap-on electrical connectors (as commonly utilized with 9-volt battery types), the electrical system within the handle thus leads through wires to a rotatable switch within the connection hub area of the aligned circular openings of the barrel and handle components. As in folded, pre-use state, the device is configured such that the battery leads proceed to a connector lead at the top portion of the handle within the circular configuration of the connection opening. The lead ends in a conductive metal structure (such as copper) that is alignable with a curved lead stationed within the body of the circular opening, as well. Again, however, in folded state the curved lead remains at a distance from the end lead from the batteries, thereby lacking any contact to provide charge therethrough. At the opposing end of the circular lead is present a barrel-stationed lead of a conductive metal structure (which may be substantially the same in structure and size to that of the handle end lead). Such a barrel-stationed lead further connects through conductive and insulated wires to the motor/stylet combination (at least) and to a further finger-manipulated switch with, as one non-limiting example, a rubber or like covering for external contact with the user for activation thereof on demand. The external switch thus includes a movable portion to further manipulate electrical leads within the barrel to contact with wires and/or leads to complete the necessary circuit to send power to the motor/stylet for drilling purposes (once they are properly extended in relation to the cannula for bone drilling purposes, of course). Thus, upon unfolding of the handle and barrel through rotation around the connection hub, the curved lead rotates to initially contact the handle lead at a certain arc placement (which may be measured as a curve angle along the arc path of the circular lead) with further rotation thereof allowing for continued contact and thus transfer of electrical charge from the batteries to the end lead stationed within the barrel. Upon operation of the barrel switch by the user, then, and with full rotation and thus extension around the connection hub of the barrel and handle to a maximum curvature angle (for instance, from 90 to 120 degrees from folded state, more preferably roughly from 95 to 115 degrees, more preferably roughly from 100 to 110 degrees), the user may then operate the drill assembly as needed to deliver the stylet/cannula within the target patient's bone, provide, for instance, again, as a non-limiting possibility, a quarter turn in the direction opposite the drilling activity of the drill device including the motor/stylet combination, whereupon the motor/stylet combination retracts back within the barrel and a cover automatically covers the stylet point to prevent any contact therewith. The handle may be manipulated from folded to unfolded state with a single one-handed motion by the user, if desired, through a throwing or like motion applied to the folded device while retaining sufficient hold on the handle itself. Such a movement thus accords the desired rotation of the barrel around the connection hub to provide the desired and necessary electrical connection from handle to barrel, and lock into place with a properly configured connection hub article that prevents unwanted movement from such a fully unfolded, extended state to permit full, unfettered use of the drill with grasp of the handle and activation of the barrel switch. The locked connection hub can subsequently be manipulated, at least in one potentially preferred embodiment, to allow for barrel rotation back to a nearly folded state, if desired. Such a connection hub may be pressed inwardly to disengage a detent, for example, within the aligned circular openings of the barrel and handle, thereby allowing for such return rotation to occur. The circular lead being configured along such an arc path remains as a proper and effective conduit of energy from the handle lead to the barrel end lead along a significant length of such a curved lead path up to, for instance a 20 degree angle between handle in folded state and unfolded state. In other words, the barrel may be rotated around the connection hub from its fully extended unfolded state to a 20 degree angle from its original folded state (as one non-limiting example) without losing electrical connection from batteries to barrel end lead. Likewise, the connection hub and circular openings of both handle and barrel may be properly aligned to effectuate a certain amount of friction to ensure the barrel does not simply fold downward after connection hub manipulation and disengagement of handle and barrel from fully unfolded state. In this manner, actually, the barrel may be rotated to any curvature angle around the connection hub from unfolded state to nearly fully folded state and allowed to remain at any selected curvature angle on demand. This is a benefit associated with the potentially preferred embodiment of a bottom edge of the handle being of a flat nature and of sufficient width to actually stand erect on a flat surface without toppling over.

Such a bottom edge structural configuration of the handle permits a couple of beneficial characteristics, then, without such an embodiment of the overall device. For example, the bottom edge of the handle may itself include an extension that protrudes forward of the handle base as it is unfolded and that simultaneously provides an initial cover for the barrel aperture prior to use and in folded state. Thus, the protective nature of such an extended bottom handle edge of the barrel opening, let alone the motor/stylet/cannula combination prior to extension out of the barrel aperture provides, as well, a sturdy base for placement of the unfolded device prior to, during, and after utilization for bone drilling, as well as a base for the device with the barrel rotated as noted above to an angle that permits directional pointing, for instance, of the barrel from fully extended unfolded state to near folded state, while standing on its own on a substantially flat surface. Such a rotational capability may help the user in keeping track of such a device during an emergency situation, as well as allow for a further embodiment of the overall device that has heretofore been nonexistent within the intraosseous device industry.

The utilization of a proper light or an array of lights, as merely examples, in conjunction with an intraosseous device has been lacking, particularly in terms of providing a sufficient amount of candle power for utilization of any such light integrated within the device itself to aid a user in viewing a specific drilling location without having to utilize a different light source (such as a flash light) with another hand. The ability to utilize a single-hand approach and allow for the other hand freedom for other emergency activities for a target patient is significant in this situation, particularly as the device may be needed within an emergency situation that is dark or poorly lit and thus requires appropriate visibility for such an undertaking, particularly drilling within a target patient's bone. The inclusion, thus, of a light or light array within and/or around a barrel aperture of the disclosed intraosseous device is of great value and heretofore unexplored within this specific industry. Any type of light, such as, without limitation, a LED, optical fiber, and the like, that does not require a significant amount of power for functioning yet supplies a sufficient candle power (at least 10 candelas, for instance) to act as a light source for directional aid in relation to the motor/stylet/cannula placement and operation on a target patient (and thus to allow for full visibility in a dark or poorly lit environment, for instance, of the target bone drilling site). A single LED, or like, light source may be provided at the lowest point of the barrel, as one non-limiting example, that shine forward in the same direction as the stylet/cannula during a drilling operation. Alternatively, an array of lights (from 2-8, for instance, more may be present as well, of course) may be provided to increase the degree of visibility for the user, as well and situated, for example, around the barrel opening periphery. At least one wire may thus be attached from the barrel end lead, or even the curved rotating lead, to the light source directly. In this manner, then, the light source may activate the moment the rotation of the curved lead reaches the proper angle for the power source from the batteries to conduct through the handle lead to the barrel portion (whether the curved lead or barrel end lead). Thus, the light or lights may automatically activate upon such unfolding of the handle and barrel with the light(s) serving as a suitable indicator that electrical charge is present from the battery to the barrel end lead for drill motor operation as well. Such an initial indication is thus a further benefit of the lighted alternative. Furthermore, however, is the ability subsequent to drilling operation, and thus retraction of the motor/stylet within he barrel and implementation of the cannula needle within the target patient's bone to then utilize the drill device itself as a flashlight on demand if desired. The further ability of the device to stand alone, as noted above, and the barrel to rotate on demand around the connection hub and remain in place at any angle further allows the user to then place the device on a suitable surface and have the light source direct as desired at a direction from the full unfolded state angle to as low as about 20 degrees from folded state while still retaining the necessary electrical conductivity between batteries and light source to provide a versatle, self-standing flashlight in addition to a drill device. Again, such a beneficial device has never been provided within the intraosseous device industry.

As another possible embodiment encompassed herein, there is an intraosseous device comprising a disposable drill/stylet combination, wherein said drill includes a stylet retraction port therein, a retracting mechanism attached to said stylet and disposed within said drill, and a cannula connected in detachable relation to said stylet, wherein said stylet is permanently attached to said drill, wherein said retracting mechanism operates subsequent to utilization of said drill to introduce said stylet and cannula within the intermedullary space of a subject bone, said retracting mechanism moving said stylet from an external location to said stylet retraction port within said drill subsequent to a drilling operation, and wherein said cannula is attached to said drill with a Luer lock component with a lip portion present external to said drill and an automatic closure internally within said drill that activates upon disengagement of said cannula from said drill. The external lip of the cannula also provides, if needed, a surface for a user to grab while maneuvering the drill. Also encompassed herein is the inclusion of a sensor on said stylet, wherein said sensor measures pressure subsequent to bone entry such that once passed through to said intermedullary space the pressure difference deactivates the drill and activates the retraction mechanism and detaching from said cannula. The method of utilization of such a device (with or without the sensor as described) is also encompassed herein wherein the cannula as retained within the bone and skin and accessing said intermedullary space of the subject bone allows for introduction or removal of fluid, etc., therein.

As it potentially concerns the utilization of the retracting stylet, the ability to provide a passive safety regimen may be accomplished in a number of ways. As noted herein, an automated door, whether internal or external to a barrel portion of the overall device may be utilized, closing through any number of possible means subsequent to stylet retraction. Such means may be pressure-based, such as remaining open as a stylet component is extended for drilling purposes (and associated with a cannula, as noted above) through a spring, or other like component, and shutting as the stylet (on sled, associated with a drill motor, or both, as examples) retracts back into the barrel itself once disengaged from the cannula. Such a door would provide a potentially complete cover, but, more importantly, prevents the ability of a user to access the sharp end utilized to drill/penetrate a patient's body (and subject bone). In such a way, then, the automatic retraction of the stylet causes the immediate closure of such a door for such protective purposes. Alternatively, however, and potentially preferred, is the ability to provide a cover guide, rather than an entire door, that provides a distinct needle access obstacle in much the same way as noted for a door above. In other words, if needed for sharp stylet end coverage effectiveness, and/or for proper internal configuration purposes of a retracted stylet puncture end cover, particularly if the barrel shape may not be particularly conducive to an automated internal door structure itself, a rotating arm mechanism may be utilized instead. Such an arm may, again, be forced away from the barrel opening and kept to the side while drilling is undertaken and then rotate to its desired position covering substantially the middle of the barrel just above the actual stylet sharp end (and, again, potentially infected needle end) in order to prevent a user from accidentally (or purposely, for that matter) contacting such a sharp needle end upon operation of such automated arm movement. In either way, whether a door or an arm (and, of course, such an arm may be considered a partial cover of any size and shape that properly resides and moves as needed within the confines of the device barrel, particularly at the egress point, of course, and thus could be a small disk, a square shape, a curved arm, basically any geometric shape structure provided in such a manner), the automated movement thereof in relation to the retracted needle/stylet provides the passive safety protection heretofore not available within the industry. Additionally, then, if an arm, or other type of partial, though effective, cover protects the user from puncture/infection after utilization and stylet retraction, there may be a need to provide further protections to ensure any fluids on the used stylet needle do not exit through the barrel and in contact with the user (or anyone else). The door possibility provides a reliable means for such a purpose, of course, particularly if it closes (and possibly seals) in such an automatic fashion. The rotating arm may have a certain amount of room that is not covered, though, leaving, potentially, the possibility of bodily fluids, etc., exiting the stylet and thus the partially closed barrel. To possibly combat such a occurrence, the movable sled component may include a stowed protective film that covers the top portion underneath the arm that unfolds and creates a fluid barrier upon such sled retraction.

In another possible embodiment of the disclosed intraosseous device, as alluded to above, the drilling motor and stylet are integrated together as a permanent component of the overall system. In this potential embodiment, however, the motor may be provided as a direct drive type (without the need of a gear box, for instance) that generates a desired drilling effect (spinning) that transfers such energy to an extended and integrated drill bit, herein a stylet. In this manner, the ability to manipulate the motor and stylet together, both to extend from the device barrel for drilling purposes and to retract within the barrel subsequent to utilization, effectively creates a single component that temporarily connects with a cannula (needle) in order to introduce both stylet and cannula within a target bone, but the motor and stylet retract together leaving the cannula therein. Such a retractable component, again, as noted above, allows for the user never to handle or contact the stylet (whether the shaft or the pointed end) at any time subsequent to drilling, thus avoiding any potential unsafe touching with a stylet having bodily fluids, etc., thereon. The direct drive motor is of sufficiently small profile to fit within the confines of the barrel housing and generate sufficient power for proper drilling by the stylet/cannula within a target patient's bone (and through skin, etc., as well), all within a time frame of at most roughly 5 seconds, preferably 3, most preferably at most 2. The torque applied for such a purpose may be measured in any manner as long as the time frame is met and the introduction within the target bone is accomplished. Such a measure is from about 0.9 to 1.1 Nm, more preferably about 0.95-1.05 Nm, and most preferably about 0.98 Nm. As such, a rotational rate of anywhere from 500-1750 rpm (more preferably from 1000-1500 rpm, most preferably about 1500 rpm) may be undertaken. In other words, the motor itself produces enough torque to meet the base requirements as noted above in terms of time and bone introduction. The battery power provided for such a purpose may be met through the utilization of any type of standard cell, with, as noted above, lithium 9-volt types (two for example) as providing sufficient levels for such drilling activities, as well as allowing for lower costs and facilitating disposal thereof as needed subsequent to utilization. The required voltage for the motor functionality is roughly 10-15, more preferably around 12. The stall current for the motor is provided in amps, roughly from about 2.5 to 5, more preferably from about 3 to 4, with about 3.2 most preferable. Furthermore, as noted previously, to provide a suitable low length barrel, and to allow for retraction of a used stylet subsequent to drilling, the motor/stylet/cannula are present on a movable internal sled component. Such a sled may be manually maneuvered to allow for extension of the stylet/cannula from the barrel opening for access thereof to a patient. Such maneuvering may be provided through, in one possible embodiment, juxtaposed grips external and on the sides of the barrel housing that protrude therefrom for the user to push both simultaneously. An internal spring surrounding the motor/stylet component compresses as the external grips are forced toward the barrel opening in this manner, thus sliding the sled (with such a "sled" potentially being the motor/stylet component on its own without the need for an undercarriage for such a purpose in this embodiment) a certain distance to allow for stylet/cannula extension outwardly while the motor portion is retained, at least in part, within the barrel itself. The spring thus compresses and the sled locks into place with the stylet/cannula extended in this manner and awaits further action in the way of the stylet and cannula disengagement subsequent to drilling completion. Such disengagement may be accorded in any manner, but preferably utilizes a simple quarter (or similar degree) turn of the device (and thus motor/stylet component) in the direction opposite the drilling rotation. The stylet (as integrated within the motor, of course) includes at a base location thereon extended arms that interface with the recessed hub (in one potentially preferred embodiment) openings of the cannula and as the drilling rotation proceeds such arms move the cannula in tandem to allow for the complete insertion of stylet/cannula within the target patient's bone. The quarter (or like) turn in the opposite direction thus allows for the stylet arms to move to parts of the cannula hub recesses that simultaneously lose contact, thus allowing the stylet (and thus motor) to disengage therefrom and, with the compresses spring in place seeking to extend back to its original uncompressed state, the release between stylet and cannula effectuates the automatic retraction of the sled back within the barrel housing, leaving the cannula within the target patient's bone. The spring thus may actually "lock" into place upon compression as the cannula portion extends outside the barrel opening with the device release rotation causing such disengagement and spring release as needed at the opening as well as at the stylet/cannula interface. Also, if desired, the internal spring may be outfitted with a protective film or like material that manipulates easily as it is compressed and extended in order to protect the internal components within the barrel housing from moisture and other elements, at least. Since the external grips (which may also be provided on top and bottom opposing sites of the barrel housing, or even at 90 or so degree angles from one another on different sides of the housing, as well; furthermore, even a single maneuvering grip may be provided alone for such a purpose, if desired) must be external the barrel housing in order to maneuver an external sled (or, again, the motor/stylet/cannula without an actual base present), there may be ingress points for moisture, etc. Thus, a film may cover such an opening or at least the spring itself, if desired. In any event, the ability to generate such retraction is paramount to providing the necessary passive safety benefits disclosed herein for the overall device. Additionally, then, and again as discussed above, the barrel housing may include an automatic closure or at least cover over the stylet point upon retraction thereof to further add to the safety aspects provided passively thereby.

Additionally, if desired, and as another potentially preferred embodiment of the disclosed intraosseous device is the inclusion of an internal cap structure to surround the motor/stylet as well as a portion, at least, of the internal spring during storage and initial extension prior to utilization thereof. Such an internal cap may accord some protections, as well, along the openings associated with the maneuver grips (handles) to extend the motor/stylet/cannula prior to use, as well. The internal cap also preferably exhibits an extension end that includes an opening that is narrower than the barrel opening, but sufficient wide to allow for the cannula hub to extend therefrom prior to and during use, at least. Such an extender cap thus provides a suitable location for the user to actually place his or her fingers for directional purposes when the drill is contacting and drilling into a target patient as well as to grip the cannula hub subsequent to drilling in order to best ensure the device can be turned in the opposite direction to retract the motor/stylet within the barrel housing, as noted above (and thus for the spring to extend, as well). In such a manner, then, it may be preferable for the internal cap to retain its position extended partially from the barrel housing. Such movement and retained extended position of such an internal cap would be permitted through the inclusion of a tab at the top (or another location, if desired) and rear portion of the internal cap itself, ostensibly acting as a buttress to retraction when moved forward with the motor/stylet. Two spaced complementarily shaped openings on the top of the barrel housing would thus provide egress points at the non-extended location and then the extended location for the internal cap with the latter creating a catch to prevent retraction of the internal cap itself after release of the motor/stylet from the cannula hub. The tab in the internal cap thus extends outwardly from the cap with an angled structure that has a slope that allows for movement forward along the internal part of the barrel housing, but with a flat end that catches, again, within the opening near the barrel housing opening. Such barrel top openings may actually be provided as indicators themselves as to the status of the usability of the overall device as the rear top opening may be outlined, for example, in green (to indicate a ready-to-use status) while the opening nearer the barrel housing opening may be outlined in red (to indicate it no longer can be used), thus allowing for further benefits as to status communications to the user. Such a catch for the internal cap also provides another benefit in that the extended cap protrusion (that aided in allowing for the user to grasp the same during and after drilling) extends a sufficient distance that the user cannot then completely fold the handle back to its original position over the barrel opening. In this way, there would be no way the user would mistakenly think the disposable device may be used again as a drill (although, as noted above, in at least one embodiment, it may still be utilized as a flash light, potentially). Thus, further communication as to device status is supplied in this manner.

In any event, the disclosure herein is directed to the complete passive safety capability of an intraosseous device and the method of such a result utilizing such a device. The stylet component, again needed to best ensure proper drilling through such a bone and prevention of deposition of bone fragments and other body materials within the cannula (for effective utilization thereof to introduce and/or remove materials therethrough to and/or from the target bone). Thus, although retraction thereof would be potentially preferred, particularly for the most reliable and effective passive safety regimen with such an intraosseous device, such a stylet component may actually be provided as a removable component from the internal structures of the drilling device itself. Thus, if desired, the stylet may be detachable, and thus not permanently attached, to the drilling components and still be considered within the scope of this disclosure. Thus, as a non-limiting example, the stylet may be screwed or otherwise connected within an internal rotatable base structure and not permanently integrated or attached thereto, and still be within the scope of this invention. In other words, mere provision of a detachable stylet would not accord any distinction from the disclosed structures and inventive features of this passive safety intraosseous device.

Additionally, the ability to provide a stationed, as opposed to sled-based, motor and gearbox combination within the drill device itself, would also allow for a configuration wherein the drill handle may actually be provided within the middle of the underside of the drill housing, rather than at the near end. In this manner, the user would have greater control of the drill itself with the trigger control (which may include two structures or one in series, related to initially extending the internal base with the stylet/cannula combination and opening the first door/seal for such egress, as well as priming the second closing door/seal as well as activate the drill operations thereafter such extension) in place within such a mid-placed handle. Such a handle may also be provided as a swiveling or other like implement that stows in such a manner to provide a smaller and thinner size when not in use. Such a configuration may allow for more efficient packaging and shipping, with the added benefit of housing, as an example, a power supply situated therein (such as one or more lithium batteries, preferably). In this manner, the swiveling (or other design) handle component may be provided with a power connection within its top portion that contacts, upon placement in full extension, with a complementary connection within the drill housing. Thus, when stowed, the power supply will not have any way to initiate any power usage until activated physically by the user, thus providing a more reliable result upon utilization.

Furthermore, with such a device, and due to the common actions and expectancies of users that undertake detachment activities of rotating implements, the actual rotation alignment of the stylet/cannula combination may be provided in counter-clockwise fashion, rather than clockwise, if desired. In this way, the user may employ the drill as needed, and in a direction as above, and then the rotation to detach the cannula, at least, may be clockwise, rather than counter-clockwise, to make it potentially easier for the user. Of course, the typical clockwise drilling and counter-clockwise detachment may also be utilized.

The disclosure thus provides a novel intraosseous device that exhibits complete passive safety in order to prevent any possible contact with the used stylet by a user (and such a result is achieved without any action by the user to actively maneuver any parts that would be external to the drill and cannula during such an activity). Such accords the user with, as well, the potential for a completely disposable drill/stylet combination for a single use purpose of both. In such a manner, the drill is provided not only with a power supply that is focused on such a single use directive, but also provided, if desired, with a shape that allows the user the ability to manually screw the drill component (such as if the power supply somehow proves ineffective at the moment of actual use). The permanent connection with the stylet, with the automatic closure to prevent stylet exposure upon disengagement with the cannula, allows for complete passive safety and, if desired, disposal as a single unit of the drill/stylet combination, thus according the user, particularly in an emergency instance, the ability to completely and safely handle the overall device post-drilling and cannula retention. The ability to avoid any need to handle the loose stylet after drilling, and the prevention, automatically, upon such drill disengagement with the cannula of any exposure to such a contaminated stylet, provides such a basis and benefit. As well, the single drill/stylet combination in disposable form allows for the user to know in each instance that s/he will have the entire device at hand at that moment when it is needed. There is no need to keep a separate drill with a box of differently sized stylet/cannula implements; to the contrary, with this inventive device, the user has, as one possible example, an entire hermetically sealed drill/stylet and cannula device ready for utilization, and thus need only to then operate the drill with the stylet and cannula in place, introduce the stylet and cannula within a subject patient's bone and into the subject bone's intermedullary space, discontinue the drilling, decouple the retraction mechanism automatically to detach the stylet from the cannula and deliver the stylet into the drill and within the retracted stylet port. Thus, with this inventive device, the user has an all-in-one device that leaves a bone-retained cannula for utilization as a port therein for fluid delivery and/or removal and a separate, integrated drill/stylet combination that, with the sharp stylet retracted within the drill body and automatically and completely enclosed from any external exposure as well, can then be placed as a single implement within a sharps (and the like) disposal bag (or like container) without any fear of puncture from the now-contaminated stylet. Such a device and system has not been employed let alone disclosed within the medical industry.

Additionally, then the inventive device may include a sensor at the stylet tip (or at least adjacent thereto), or as described above, the motor itself, that activates upon pressure application at the skin and/or bone of the subject patient. Once such is introduced in this manner, the sensor increases in pressure detection once the stylet contacts the bone itself. Thus, once the stylet enters the subject bone intermedullary space, the pressure drastically reduces, indicating the presence of the stylet within such a space. Once this pressure difference is measured, the sensor indicates the same to the drill motor and stops the power from running at that instant. Such a pressure sensor thus accords the user the ability to control the depth of the stylet/cannula entry, effectively preventing the stylet from entering the bone too far and, for the most part, allowing for maximal access to the intermedullary space of the subject bone for introduction/extraction of fluids, etc., through the retained cannula. Furthermore, then, the sensor deactivation of the drill may further lead to activation of the retraction mechanism of the stylet to decouple from the cannula (thus leaving the cannula, again, retained within the patient's skin and bone for further utilization) and then retract up into the drill within a recessed port therein for safe handling thereafter. Certainly, the sharp end of such a stylet is to be avoided both prior to and after actual utilization as an intraosseous implement. The ability, particularly when in an emergency situation, to merely handle a device with an exposed stylet prior to drilling, and not afterwards (when contact with the subject patient's fluids, etc., heightens the potential problem with piercing/puncturing one's self as a paramedic, clinician, EMS personnel, etc.) is of enormous importance, certainly. Such a retraction mechanism thus may be employed as the drill stopping and then turning the other direction until the stylet is delivered to the retraction port. The drill, as noted above, also includes an enclosure that automatically closes upon disengagement from the cannula or upon retraction of the stylet. If desired, however, the drill may also or alternatively include an enclosure that automatically maneuvers in place over the stylet egress opening upon movement of the stylet implement into the retraction port (such as a spring-loaded sliding mechanism that activates once the entirety of the stylet passes through such an opening). In this manner, also, the coupling of the stylet to the cannula may be provided with an abutment as the drill activates in the "forward" (towards the bone) direction, thereby causing the cannula to move with the stylet. In the opposite direction however, the abutment may release as the stylet rotates in the opposite direction allowing for the decoupling of the two components as needed. Certainly, any other type of coupling and decoupling mechanism may be employed for such a purpose and the retracting mechanism may be of any other type as well. For instance, a spring-loaded component may work with the drill to push the stylet "forward" when the drill is activated and then, upon disengagement of the drill, the spring releases as well forcing the stylet up into the drill chamber of placement within the retraction port. In such a possible alternative, then, the coupling with the cannula may be the same type of abutment configuration but with the discontinuation of the drill according the spring-loaded implement therein to not only move the stylet upward into the drill chamber, but also when the alignment allows for decoupling with the cannula, the full movement is further permitted and operated.

Alternatively, then, the potential presence of a sensor may be employed on the motor and/or gearbox as well or instead. In this manner, the initial torque of the drill, prior to skin and bone contact, will be monitored and upon penetration through the target bone, such a reading will again be attained thus indicating and allowing for immediate deactivation of the motor and/or gearbox (and effectively stopping the drill). Thus, because the torque measurements (and pressure, for that matter) will increase as the rotating stylet/cannula combination past through the target bone, once such is completed and the intermedullary space has been reached, the pressure measurements will change significantly enough to provide such deactivation indications and/or controls automatically. In other words, the specific gear required to effectuate such a drilling operation will initiate at a starting level, move to another higher gear thereafter to increase the torque applied, and, upon penetrating through a target bone, the gear may then change back to a lower one. At that point, such a sensor may then activate to turn off the drill motor.

Another potential embodiment of the overall intraosseous device utilizes an internal spring-loaded component housing the stylet, a gearbox, and a motor (such as on a sled-type implement). Such a spring-loaded component thus rests in non-compressed (fully protracted) state with the stylet present within the body of the drill housing itself (as well as the gearbox and motor which are connected thereto). Upon decision to utilize the device, the user would compress the spring through an external handle (with a separate handle utilized as a post for such a compression force to take effect), thereby pushing the overall sled-type component outward to an egress opening within the drill. At such an opening would be the cannula with a Luer lock attachment with a screw-type portion connected to the drill at such an egress opening and a lip portion external thereto. The cannula includes a lumen that is permanently attached to the Luer lock implement, as well, and aligned such that the spring-loaded component forces the permanently attached stylet therethrough the bore of the hollow cannula and extending to provide the stylet tapered end through the end thereof. At such a point, the spring allows for the sled-type implement to move linearly to such a stop and then latches a catch point within the drill that prevents any further movement to decompression state. Once this latch is in place, the motor is then aligned with a power source, or alternatively, a switch is properly closed to allow for the motor to then be activated. With activation, the stylet then drills as a drill bit-like implement with the user then pushing forward on the drill device itself to force the style and cannula through the target patient's skin and target bone until reaching a desired depth (whether alerted by sensor or not). Once this action is over, the user can then, as one example, turn the drill a quarter, half, third, etc., any degree rotation to unlatch the sled-type implement from the cannula allowing it to then retract in to the non-compressed spring status. Of course, any manner of unlatching may be undertaken as long as the retraction occurs while the cannula is still attached to the drill. Such effectively moves the gearbox, motor, and most importantly, used stylet back within the confines of the drill housing. Thereafter, the user then detaches the cannula from the drill end; such may be accomplished with a turning action, as noted above, subsequent to and to a larger degree than for the retraction operation. Once this occurs, and the screw-type portion of the cannula Luer lock is free from the drill, a pressure-based closure (in contact with the cannula when in place), then automatically and immediately covers the egress opening of the drill. Such a pressure-based closure may be provided on one side of the Luer lock and thus close instantaneously in that one direction once the Luer lock (or portion thereof) and the pressure-based closure are no longer in contact with one another. Alternatively, there may be two opposing pressure-based closures that meet half way across the drill housing egress opening upon disengagement of the Luer lock. As another possible alternative, the drill may include a pressure-based or other type of automated closure that is further within the drill housing as to cover an enclosure tube housing the stylet prior to extension and after retraction back into the drill. In other words, such a tube may provide a directional cover or at least a simple enclosure for the extendible and retractable stylet. External to such a tube, which itself would include an egress opening to permit such extension of the stylet into and through the cannula when in use, but within the confines of the drill housing, may thus be a pressure-based closure, much like that discussed for the Luer lock cannula egress opening. However, in this situation, the pressure-based cover would not be primed for spring (or the like) decompression until the stylet retracts back into such a tube and/or the movable platform including the stylet, gearbox, and motor, at least, moves back into its original decompressed state. In this manner, either the stylet tube cover pressure-based closure may be provided, in one possible embodiment, in such a primed position separate from the location of the platform, or it may be actually aligned and attuned to the platform movement. Thus, it is not aligned (and thus separate) from the platform movement and/or location, the closure may be activated by a mechanical device that releases the spring thereof only upon retraction of the stylet and/or entire platform. If aligned with the platform and/or stylet, then such a pressure-based closure may be maneuvered itself into place over the tube egress opening when the stylet is extended into and through the cannula core and then activate at its own static location to close upon such stylet and/or platform retraction. In either case, this alternative provides, again, a definitive passive safety implement and procedure for intraosseous activity due to the automatic retraction of the stylet and then automatic enclosure thereof upon such movement. If desired, as well, the retraction mechanism may be related directly to the motor activation which may be programmed or at least controlled by the attainment of a proper depth of stylet and thus cannula insertion within a target bone. In such a manner, then, the motor may be associated with a sensor or simply by the completion of the necessary drilling action (drill no longer moves forward, for example, while drilling), or the power supply ends after the necessary amount has provided the drilling result desired. In either case, the combination of such automatic turn off and automatic retraction thereafter (will the potential for automatic closure of the stylet housing tube) provides a total automated passive safety result heretofore unexplored within this medical area. Such a result, whether utilizing the Luer lock "controlled" closure device or the stylet retraction "controlled" closure device, the ability to provide total protection from used stylet contamination, particularly in terms of the automatic closure of the only access opening (or openings) to such a retracted used stylet provides such a passive safety benefit and method wherein the stylet has no possible external contamination itself outside the cannula and/or drill housing subsequent to drilling.

With such in mind, then, the ability to retract the stylet automatically, seal it off automatically, and provide any further automatic protections simply through the disengagement of the drill from the cannula (thus providing the necessary access for drug delivery, matter removal, or other end use, including, without limitation, stem cell collection) is of great importance to provide the necessary passive safety results. As such, although it may be preferable to have a fully integrated stylet (as it is connected with the gearbox, motor, and/or any other component within the drill), such may actually be avoided to provide, for example, and without limitation, the ability to provide a recyclable drill, albeit with, for example, a module including the retracted stylet, with or without any other inner component, that is completely disposable, is also a possible embodiment of this disclosure. In other words, the ability to retract the stylet automatically is the important consideration; the fully integration thereof within the drill is a possible embodiment, but not required in every instance due to the potential to jettison the retracted (and safely enclosed) stylet after use. Of course, being held in such an enclosed state within the confines of the drill housing allows for full disposability of the entire device, if desired, as well.

In terms of disposability, then, the device may be configured and supplied to allow for a single use thereof, again, if desired. In fact, the device may be provided within a single hermetically sealed (and pre-decontaminated or like treated state in total, ostensibly for safety for the target patient, of course) package (such as a polyolefin, like polyethylene, polypropylene, polybutylene, or other polyolefin, or blend thereof, a polyester, a nylon, a polyacrylate, a polylactic acid, etc., and combinations thereof) that may easily be opened by a user, kept by his or her side during utilization, and then used as a final disposable (or returnable) package to hold the used drill device. In such a manner, then, the user may utilize the separable connection means (such as a perforated line, a tearable zip-lock, and the like) to access the drill device in total, use it until the cannula remains in the bone for active delivery or material removal therefrom, as needed, and then take the safe, stylet retracted and sealed device and place it back within the packaging with a different sealing implement provided to prevent any other possible contamination thereof. Such could then be totally destroyed, if desired, or the mechanical portions thereof may be reclaimed and recycled for inclusion within another new drill device with full decontamination of any components thereof as originally used. Such a stylet, however, will never be utilized again and the tube within such an implement is thereafter kept after retraction may be a modular component that allows for utilization of the other structures and components that did not involve direct contact with the target patient's skin, fluids, and bone.

To provide a compact structure, initially, as stored and transported before utilization, such a device may include, as alluded to above, a foldable handle portion. In such a manner, the handle of the drill device may actually stow to avoid a bulky end portion thereof. This folding handle may also include a power source (batteries, for instance) that remain unaligned with the electrical parts of the drill until moved to the desired position. Such a handle may thus also be provided as detachable from the drill, to allow for facilitation of possible recycling thereof. Decontamination and disinfection (as needed) may thus be undertaken with the detached power supply/handle component to allow for acceptable further utilization in a different and later activity. The foldable handle may thus fold either forward on the bottom rear portion of the drill or backward thereon.

The overall drill may, in this type of embodiment, include two or more sled-type implements if desired in order to more efficiently (and possibly reduce size overall of the device) accomplish such a passive safety result. Additionally, the drill may have a handle that folds for more improved storage purposes and may include a battery (or multiple batteries) therein as well. The cannula may be provided with screw-type channels at the insertion end, as well, to potentially improve retention with a target bone as well as facilitate drilling therein. Additionally, the drill may solely rotate the stylet component for such an action or, alternatively, may engage with the cannula to rotate simultaneously with the stylet.

These and other aspects of the disclosed subject matter, as well as additional novel features, will be apparent from the description provided herein. The intent of this summary is not to be a comprehensive description of the subject matter, but rather to provide a short overview of some of the subject matter's functionality. Other systems, methods, features and advantages here provided will become apparent to one with skill in the art upon examination of the accompanying FIGURES and detailed description. It is intended that all such additional systems, methods, features and advantages that are included within this description, be within the scope of any claims filed now and/or later.

BRIEF DESCRIPTION OF THE DRAWINGS

The novel features believed characteristic of the disclosed subject matter will be set forth in any claims that are filed now and/or later. The disclosed subject matter itself, however, as well as a preferred mode of use, further objectives, and advantages thereof, will best be understood by reference to the following detailed description of an illustrative embodiment when read in conjunction with the accompanying drawings, wherein:

FIG. 1 depicts a cross-sectional view of one possible embodiment of a drill device described herein prior to utilization in an intraosseous procedure.

FIG. 2 depicts the same device as in FIG. 1 with the stylet inserted through the cannula for drilling operations.

FIG. 3 depicts the same device as in FIG. 2 subsequent to drilling with the stylet retracted.

FIG. 4 depicts the same device as in FIG. 3 subsequent to cannula detachment.

FIG. 5 shows a cross-sectional view of a drill device having an extendible internal base alternative embodiment in pre-extended form and with a mid-portion handle in stowed position as packaged.

FIG. 6 shows the device in FIG. 5 with an unstowed handle.

FIG. 7 shows the device in FIG. 6 with opened initial door at the drill device distal end.

FIG. 8 shows the device in FIG. 7 with the internal base assembly extended and the stylet/cannula combination provided with portions external the egress point of the distal end.

FIG. 9 shows the internal assembly of FIGS. 5, 6, 7, and 8 in greater detail.

FIG. 10 shows the device in FIG. 8 with the cannula in place within a patient's target bone and skin, the internal assembly with the stylet retracted within the device, and the drill device second door closed to protect from the retracted stylet automatically.

FIG. 11 shows a side view of the close-up of the stylet/cannula combination of FIGS. 5, 6, 7, and 8.

FIGS. 12, 13, and 14 show different close-up views of the interface between the internal assembly rotatable arms and the cannula base with the capability of temporarily connecting therebetween and the ability of detaching through a slight turn and pull away of the internal assembly.

FIG. 15 shows a side perspective view of another potentially preferred embodiment of a stowed and folded hand-held passive safety intraosseous device of the disclosure.

FIG. 16 shows the deployed and ready to use device of FIG. 15.

FIG. 17 shows a side view of the same device of FIG. 15.

FIG. 18 shows a side view of the same device of FIG. 16.

FIGS. 19 and 19A show a cross-sectional view (19 side perspective and 19A side view) of the device of FIG. 15.

FIG. 20 shows a side, bottom cross-sectional view of the device of FIG. 16 after the stylet has been retracted within the drill body.

FIG. 20A shows a side perspective cross-sectional view as in FIG. 20.

FIG. 20B shows a close-up side perspective view of the sealed drill body after cannula disengagement.

FIG. 21 shows a side cross-sectional view of the stylet and cannula with stylet motor shaft permanent connection.

FIG. 21A shows the disengaged stylet and cannula of FIG. 21.

FIG. 21B shows a rear side perspective view of the stylet and cannula connection as in FIG. 21.

FIG. 22 is a side perspective view of the device of FIG. 15 post-use and upon separation of sealed drill body and handle.

FIG. 23 is a side perspective view of another potential embodiment of the disclosed device in closed, pre-used position.

FIG. 24 is a side perspective view of the device of FIG. 23 in unfolded, pre-used position.

FIG. 25 is a side perspective view of the device of FIG. 24 in primed, extended position ready for intraosseous drilling utilization.

FIG. 29 is a cross-sectional side perspective view of the FIG. 24 device in unfolded, pre-used position.

FIG. 29A is a cross-sectional side view of the FIG. 27 device in unfolded, pre-used position.

FIG. 30 is a cross-sectional side perspective view of the FIG. 25 device in primed, extended position ready for intraosseous drilling utilization.

FIG. 30A is a cross-sectional side view of the FIG. 27 device in primed, extended position ready for intraosseous drilling utilization.

FIG. 31 is a cross-sectional side view of a potential embodiment of the disclosed device subsequent to stylet retraction after drilling utilization.

FIG. 31A is a top side cross-sectional perspective view of a potential embodiment of the disclosed device subsequent to stylet retraction after drilling utilization.

FIG. 31B is a close-up top side perspective view of the drill opening of the device of FIG. 31A subsequent to stylet retraction and needle disengagement.

FIG. 32 is a side perspective exploded view of a potential embodiment of a stylet/needle combination for utilization with the disclosed device.

FIG. 32A is a cross-sectional side view of the stylet/needle combination as connected for utilization within the disclosed device.

FIG. 32B is a side perspective view of the stylet/needle combination as connected for utilization within the disclosed device.

FIG. 34 is a side perspective view of an IV line/needle combination for intraosseous delivery of medicaments subsequent to utilization of the disclosed device.

FIG. 34A is an exploded side perspective view of the IV line/needle combination of FIG. 34.

FIG. 34B is a cross-sectional side view of the IV line/needle combination of FIG. 34.

FIG. 35 is a side perspective view of another possible embodiment of the overall device in folded pre-used state.

FIG. 36 is a side perspective view of the device of FIG. 35 in unfolded pre-use state.

FIG. 37 is a side perspective view of the device of FIG. 36 in unfolded ready-to-use state.

FIG. 40 is a front side perspective exploded view of another possible embodiment of the overall intraosseous drill device.

FIG. 43A is a side perspective view of the device of FIG. 43 in unfolded (open) state with the automatic light activation prior to use.

FIG. 43B is a side perspective view of the device of FIG. 43A in unfolded ready-to-use state.

FIG. 44A is a side perspective view of the device of FIG. 44 in unfolded (open) state with the automatic light activation prior to use.

FIG. 44B is a side perspective view of the device of FIG. 44A in unfolded ready-to-use state.

FIG. 60 is a side view of the device of FIG. 55 subsequent to use standing on its own with the light activated and rotated at an angle.

FIG. 61 is a side cross-sectional view of an after-use device in re-folded state as far as it can be manipulated with protective cap extender blocking complete closure.

DETAILED DESCRIPTION OF ILLUSTRATIVE EMBODIMENTS

Figure 14:
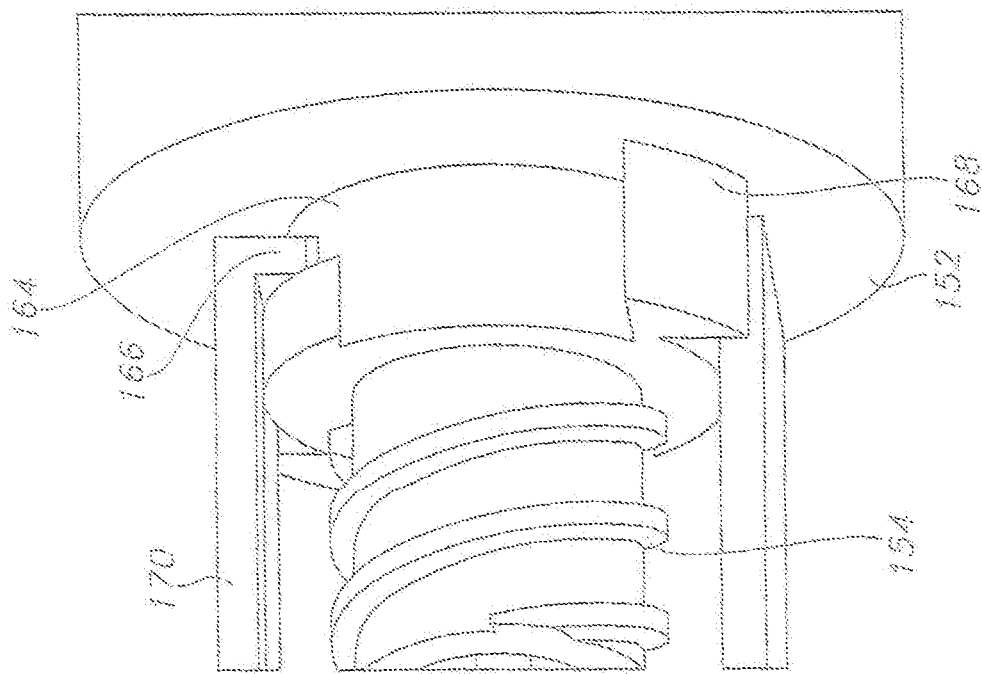

Reference now should be made to the drawings, presented as non-limiting possible embodiments in accordance with the descriptions provided above. The ordinarily skilled artisan would fully understand the breadth and scope intended herein in relation to the following potentially preferred types.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

FIG. 1 depicts the drill 10 with a housing 12, completely enclosing a rotatable stylet 16, connected permanently to an implement 18 rotated by a gearbox 20, which is powered by a motor 22. A power source 34 is provided in the handle 36 thereof, as well. A platform 38 for placement of the gearbox 20 and motor 22 is provided that forces the gearbox 20 and motor 22, and thus stylet 16, to slide along a track 24 and is related with a spring 50. In non-compressed form, the platform 24 rests as shown, with the stylet 16 tapered end at the tip of a Luer lock 54 opening of the cannula 14. The cannula 14 is connected with the drill housing 12 at an egress opening 44 and is provided in this state prior to and during utilization. Also present within the housing 12 is a spring-based 42 closure 40 internal thereto that is compressed in form as the Luer lock end 54 of the cannula 14 is present within the drill housing 12.

FIG. 2 shows the compression of the platform 24 moving spring 50 through external pressure to a lever 32 which maneuvers the gearbox 20 and motor 22 with the stylet 16 forward along the track 24 such that the stylet 16 moves through the cannula 14 bore and out the end thereof in order to provide a tapered drill bit. The motor 22 includes a connection 26 that aligns with a power source, 28 as well, in order to allow for motor activation in such a state. The spring 50 connects with a movable latch with two separate components 46, 48 at such an extending state and remains static until user activation changes such a status. The user may then place the stylet tip on a target patient's skin (56 of FIG. 3, for instance) in the area for bone access (58 of FIG. 3) and apply the power to a switch 29 and the handle that leads to the power component 34 through a lead 31 that then leads through a wire 30 to the motor 22 to rotate the stylet 16 for such operation until the stylet 16 and cannula 14 have reached a selected depth therein.

FIG. 3 provides post-drilling status as the cannula 14 resides within the bone 58 and attached to the drill housing 12, but the spring 50 has been delatched (such as through a compressed switch, button, and the like, or twisting and/or turning of the drill a slight amount to achieve the delatching result) and the platform 24, including the gearbox 20, motor 22, and stylet 16, has retracted, leaving the stylet 16 within the confines of the drill housing 12 subsequent to the drilling step.

FIG. 4 thus shows the detachment of the cannula 14 from the drill housing 12 (such as through a twisting or turning motion of the drill itself). The instant such cannula 14 moves sufficiently outward through the egress opening 44, the closure 40 springs 42 over such an opening 44, thereby encasing the stylet 16 in total. The drill body with stylet 16 is thus sealed and may be disposed of while the cannula 14 remains in the subject patient's bond 58 for introduction of medicaments or removal of fluids, etc., therefrom and therethrough.

FIGS. 5-10 show a different embodiment from that above, with a drill device 110 and a housing 112, a stylet 116, a cannula 114, a revolving hinged handle 136 housing a power supply 134 and having a switch 129, a hinge 133, and an electrical connector 160. The drill body includes a first closed door 143, a motor 122, a gearbox 120 a drive shaft 119, a stylet holder 118, a cannula Luer lock component 152, an opening for the cannula and stylet to exit 144, an electrical connector 162 for the handle to contact, and a second sealing door 140. In this embodiment, as well, is a annual controller device 132 to move the cannula 114 and stylet 116 as attached together internally to an external location for skina do bone contact. FIG. 6 shows the handle turning to engage electrical contacts 160, 162 which activates the initial door 143 to allow egress of the cannula 114 and stylet 116 through the opening 144. The manual controller 132 then moves the handle switch 129 then operates the drill to implant the cannula 114 within a patient's bone (58 of FIG. 3). FIG. 9 shows the internal portion of the drill body with a compressed spring 121 that engages to retain the stylet 116 in place for the drill operation. A compressed door spring 142 awaits activation upon retraction of the stylet spring 121 to seal the opening (144 of FIG. 5) as well. The actual Luer lock 154 is shown to allow the needed access for intravenous, etc., utilization after implantation within a subject patient bone, as well. The drive shaft 119 provides the necessary rotation of the stylet 116 and attached cannula 114 during operation with the stylet storage tube 118 awaiting final disposition therein after utilization. FIG. 10 shows the disengagement of the cannula 114 from the drill housing and the sealed door 140 in place. As well, the stylet 116 has been retracted and sealed within the tube 118 for disposal thereof.

FIG. 11 provides a multi-sided taper 117 of the stylet 116, but with even edges thereover, and an even multi-tooth 115 cannula 114 edge below such a taper 117 configuration of the stylet. This overall configuration provides an effective drilling capability, particularly through bone. Of course, any functional design and configuration would be permitted within these structures.

Figure 13:
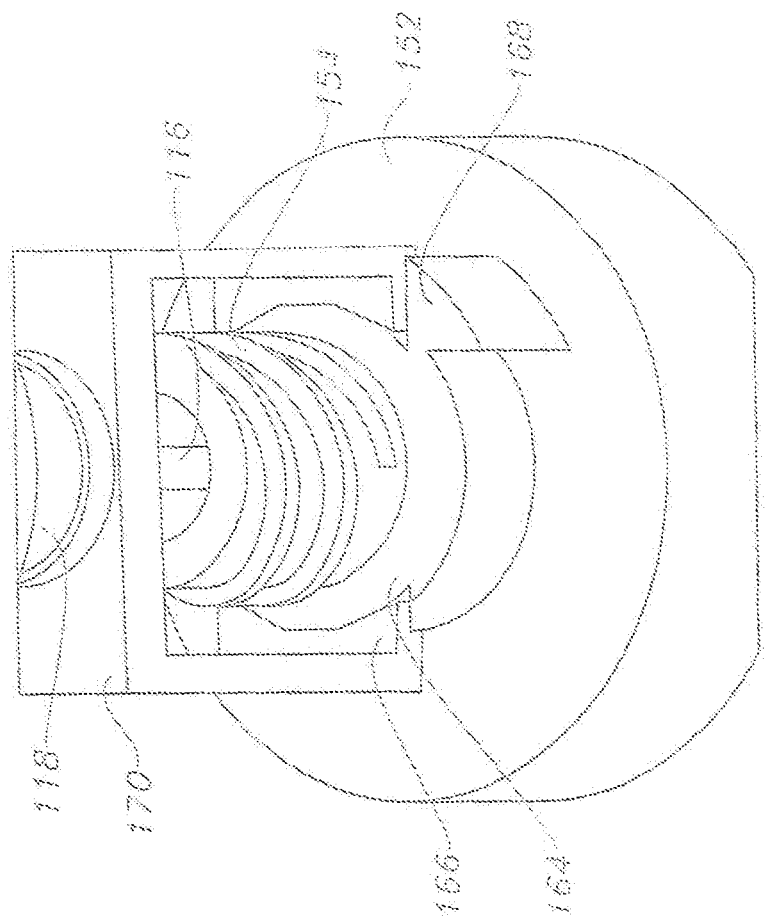

FIGS. 12-14 show a close-up of the interface of cannula base 152 and internal assembly base rotatable component 170. The arms 166 thereof the rotatable base extend perpendicular and then again upward with flanges that are complementary to notches 164 within the cannula base 152. Here two opposing arms 166 are present to accord directional torque when engaged with further flanges 168 preventing the cannula 114 from moving away from the base assembly 152 during use. With a turn (either direction clockwise or counter-clockwise, depending on how the configuration is provided) the base assembly arms 166 are removable from the cannula base 152, allowing for the cannula 114 to remain in a target patient's bone and skin while the drill device, and the internal assembly including the stylet, retract back. The Luer lock 154 is thus present to provide the connections needed for medicament delivery and/or fluid, etc., removal from such a bone.

FIGS. 15-18 show another potentially preferred embodiment with a device that may be operated with a single hand, opened, aimed, drilled, and sealed (and possibly separated from its handle) easily and safely. The drill device 210 includes a drill housing 212, a handle 236, a hinge 233 at the handle/drill housing interface, grips for handling 276, a handle switch for operation 229, a stowed cannula/stylet cover 272, a cannula 214 and stylet 216, a cannula attachment 254, a cannula holder 253, and a drill housing opening 244. The cannula 214 and stylet 216 stows in the cover 272 until the caregiver/user opens the handle 236 through the hinge 233 (a button, release component, etc., may be employed for such a purpose) with the cover 272 protecting from piercing, etc., and keeping the cannula 214 and stylet 216 protected from infection, etc., prior to utilization. Upon opening, the cannula 214 and stylet 216 are thus available for utilization (implantation/insertion within a patient's bone). The switch 229 is activated to start the drilling action. FIGS. 19 and 19A show differing views of the cross-sectional internal components thereof, with a slide track 224 to permit the retraction of the stylet 216. A compressed spring 250 awaiting disengagement for such a purpose. A motor 218 to provide torque and a drive shaft 220 permanently attached to the stylet 216. A spring-loaded component 22 is present to operate the sealing door (240 of FIG. 20B), as well. The drill housing 212 includes a hinge connector 280 to permit disengagement through the hinge nut 233, as well.

FIGS. 20 and 20A show the retracted stylet 216 upon disengagement from the cannula 214 and retraction of the spring 250 to cause such an action (slide along the track 224 of FIG. 19, for instance). The power supply 234 in the handle 236 provides the needed electrical charge to provide the motor 218 to operate and the drive shaft (223 of FIG. 21B), as well. The disengagement of the stylet 216 may be through rotation of the drill housing 212 after introduction of the cannula 214 and stylet 216 within a subject patient's bone. Upon retraction, then, FIG. 20B shows the sealing door 240 over the drill housing opening 244 to keep the used stylet 216 therein safely. The springs 220 activate upon reaction of the stylet 216, as shown in FIGS. 20 and 20A, as well.

FIGS. 21 and 21B show the connection of the cannula 214 and stylet 216 with the permanently attached motor shaft 223, as well. The cannula cover attachment 253 includes therein the needed Luer lock 254 for utilization with IVs, etc., after implantation. FIG. 21A shows the separation of cannula 214 and stylet 216, as well, with the Luer lock 254 accessible.

FIG. 22 thus shows the sealed door 244 over the drill housing opening 240 and the separation of the handle 236 through the hinge nut 233 disengagement from the drill housing connection 280 and the handle connection 281 (from the opening thereof 283). The sealed drill housing may thus be disposed of (such as within a sharps container, or the like) and the handle may be disposed of separately. Such separation allows for the smaller profile devices to be disposed of as needed, particularly if batteries and other power devices are not permitted within sharps containers.

Thus, with this type of device, of which this is merely one possible embodiment, of course, there is provided a totally passive safety procedure for intraosseous activities. In addition, the entirety of the drill may then be disposed of to further reduce, if not remove, any potential for contamination thereafter externally. The drill may further be provided within a hermetically sealed enclosure prior to actual utilization with the cannula in place and the only requirement being the spring movement to introduce the stylet for drilling purposes through the cannula bore. Additionally, there may be provided a battery/motor (or other component) separator to ensure, as best possible, the power supply is not depleted prior to actual removal from such an enclosure. Thus, a tab, for instance, of plastic (which may be the same plastic as for the enclosure itself), may be integrated within the enclosure structure to act as such a separating component. Upon opening the enclosure, then, the separating component automatically disengages between power supply and other component, thus allowing for the connection to then flow electricity as needed.

The cannula may also be provided herein as a MRI-safe metal to permit such a subsequent activity without the need to remove and introduce another one after such an action is undertaken.

Figure 26:
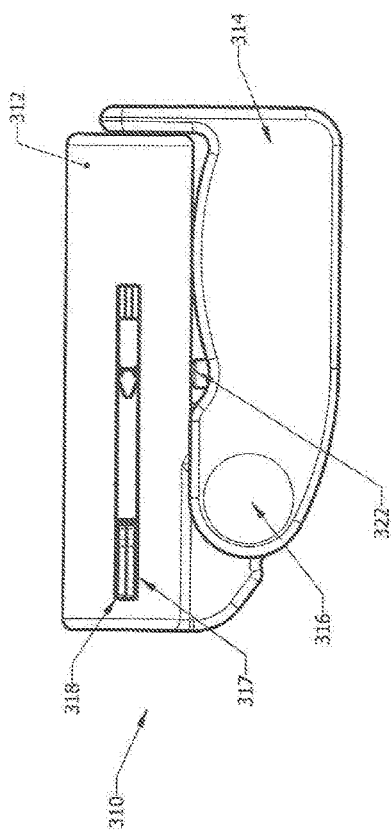
FIG. 26 is a side view of another potential embodiment of the disclosed device in closed, pre-used position.
Figure 28:
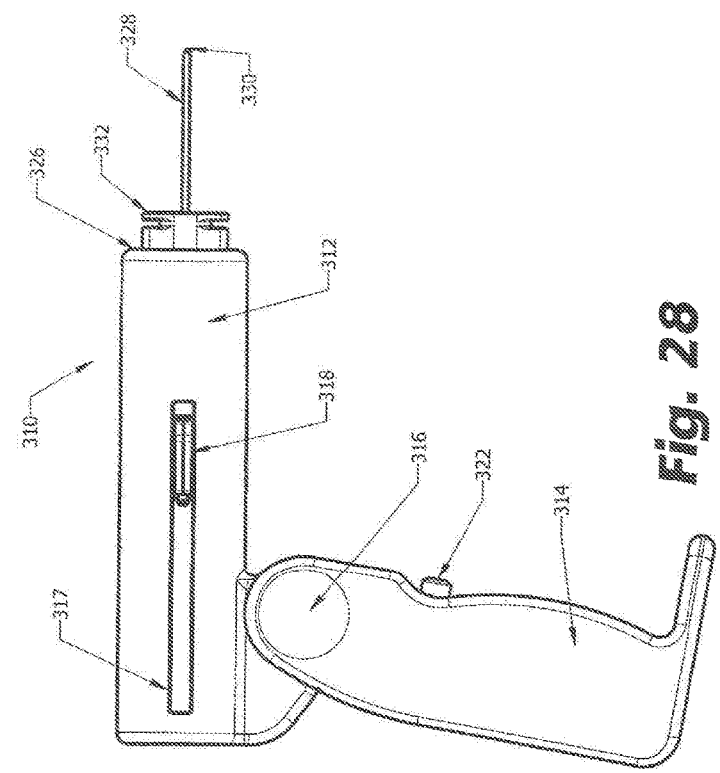
FIG. 28 is a side perspective view of the device of FIG. 26 in primed, extended position ready for intraosseous drilling utilization.
Figure 27:
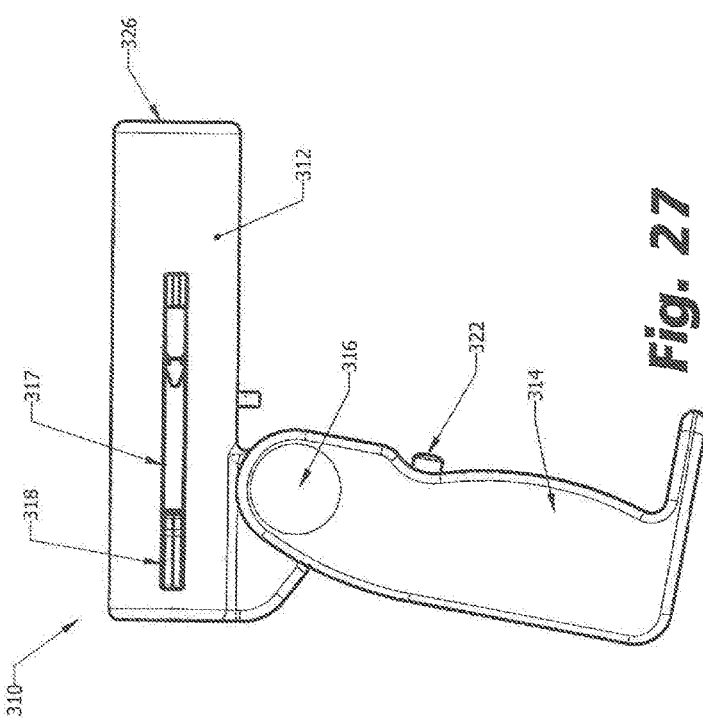
FIG. 27 is a side view of the device of FIG. 26 in unfolded, pre-used position.

FIGS. 23-31 show another potentially preferred embodiment of the disclosed passive safety intraosseous device. The device 310 includes a barrel 312, a handle 314, a connection hub 316, a drill switch 322 on the handle 314, a sled slide opening 317, slide grips 318, and a barrel opening 326. The device in FIGS. 23 and 26 are shown with the handle 314 and barrel 312 in stowed (folded) position with the end of the handle 314 covering most of the barrel opening 326. As the handle 314 and barrel 312 and unfolded, as in FIGS. 24, 25, 27, and 28, the drill switch 322 is made available (in this embodiment it is present on the handle 314) and the connection 324 between handle 314 and barrel 312 is shown as well. FIGS. 25 and 28 thus further show the extension of the stylet 330 and cannula 328, as well as the cannula hub 332, through the barrel opening 326, thus allowing for the device 310 to be in ready-to-drill state. FIGS. 29 and 29A show the device 310 in prior-to-use state with the handle 314 and barrel 312 unfolded, but the stylet 330 (and thus cannula 328, of FIG. 28) still within the barrel housing 312. The slide grip 318 is in its initial state at the rear of the barrel 312, as a result. Further shown are the motor 340 the spring 334 and the cannula 328 and hub 332 through the side opening 336 of the barrel 312. FIGS. 30 and 30A show the extension of the cannula 328 and stylet 330 for ready-to-use status of the device 310 with the slide grip 318 moved to the other end of the barrel housing 312 and the spring 334 compressed as a result. FIGS. 31 and 31A show the device 310 in post-drill state with the cannula 328 and cannula hub 332 free from the stylet 330 as it has been retracted back within the barrel 312 and the integrated motor 340 as well with the spring 334 extended in reaction to the disengagement of the stylet 330 and cannula hub 332. The cannula 328 and cannula hub 332 would thus be maintained within a target patient's bone (such as 58 of FIG. 3) and the device then disposed of with the retracted stylet 330 passively moved and stored to prevent any further contact after removal from a patient's body.

FIGS. 32, 32A, and 32B provide a close up view of one possible embodiment of a recessed cannula hub 332 to provide, at first, the stylet 330 and cannula 328 interface (with the stylet 330 shown in this instance separated from the integrated motor (340 of FIG. 31, for instance) solely to allow for suitable view of the two component parts in this manner. Again, in actuality, the stylet 330 is fully integrated and inseparable from the motor (340 of FIG. 31) when in actual use within the device (310 of FIG. 23) and separation of the two would cause the device to be unworkable. In this instance, then, the stylet 330 is inserted within he cannula 328 and extends therefrom when nested together (FIGS. 32A and 32B, for example). The hub 332 includes, in this possible embodiment, two opposing sides in rounded triangular shape (overall a roughly oval shape) 356 that allow for grasping by the user, at least, during drilling operations and retraction of the stylet 330. As shown in FIG. 32, then, the hub 332 includes a recessed opening 352 for the stylet base 344 to enter and temporarily connect with through rotation (as noted above; retraction is accomplished through rotation in the opposite direction). A bore 354 within the cannula hub leads to the cannula (needle) 328 itself to permit placement of an IV, as one example (as shown in FIGS. 34, 34A, and 34B, for instance) thereon to supply fluids, etc., external the cannula, therethrough, and into a target patient's bone (intermedullary space). The stylet 330 further includes a permanent adapter 340 that connects and secures with an integrated motor (such as, as one example, 876 of FIG. 56) with an end opening for permanent insertion of a motor shaft extension 358 to turn/spin the stylet 330 (and thus the cannula 328 when connected together), as well as a side opening 348 for insertion of a permanent connection (such as a bolt or like connector that is not removable without damaging either the stylet 330 or the motor) from the motor as well. As shown in FIG. 32A, the cannula hub 332 is complementarily configured with the arms 360 of the stylet base 344 to secure as both are spinning in the same drilling direction. Again, as the stylet 330 and motor are then rotated in the opposite direction, the arms 360 free from the cannula hub opening 352 and both retract leaving the cannula 328 within the target patient's bone and the hub 332 at the target patient's skin surface. Importantly, it is noted that the cannula hub 332 shown within this embodiment is, again, one possible alternative. If the user desires the utilization of a Luer lock hub, such is of course permitted in such an instance for both stylet and cannula connection and IV, etc., insertion during fluid, etc., introduction subsequent to bone drilling. FIGS. 34, 34A, and 34B show the utilization of a fluid feed line 372 (such as an IV, as one example) connected with a recessed cannula hub 332. The line 372 includes, in this instance, a curved cover 370 (although it is possible to avoid any curved cover, certainly, and just have the line feed directly, if desired) with a complementary connector 374 with similar structure internally to the retracted stylet (330 of FIG. 31, for instance) to attach over the recessed hub internal adapter extensions 352 over the cannula opening 354. The feed line 372 thus includes buttresses 376 to secure with the cannula hub 332, thus, when aligned with the cannula opening allows from fluid or other materials to enter the cannula bore 378 for transfer to the target patient's bone.

Figure 33:
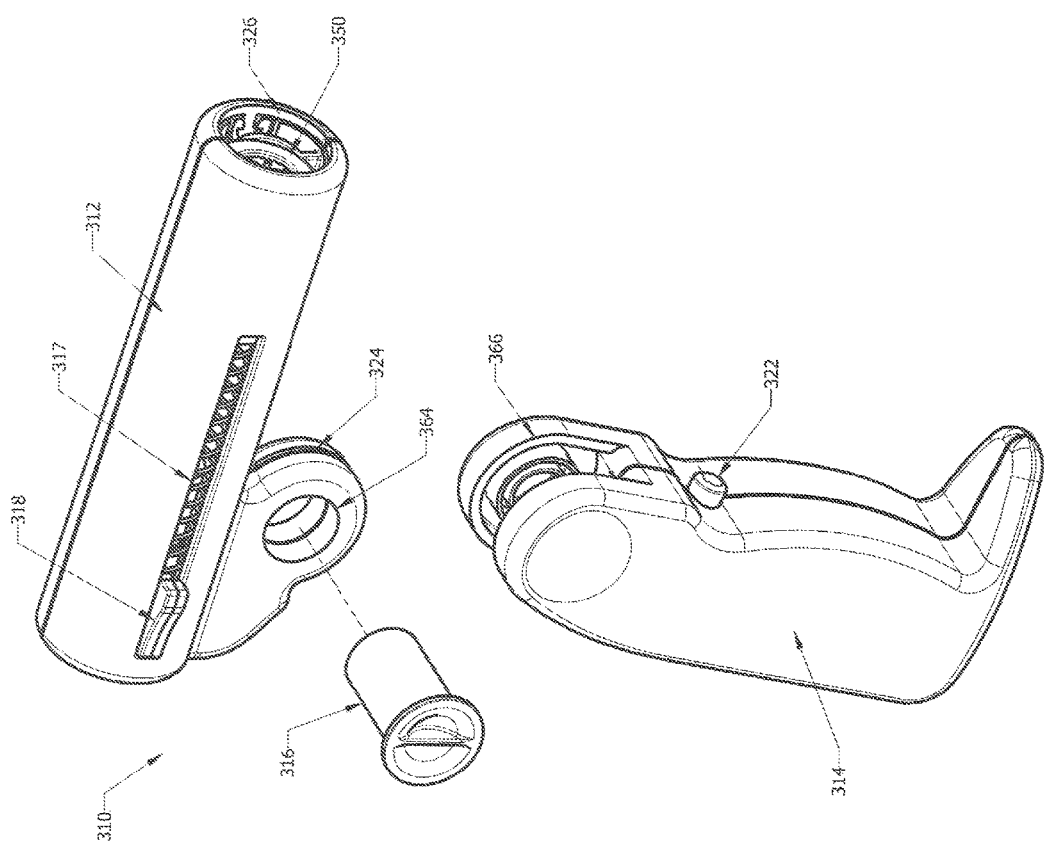
FIG. 33 is an exploded side perspective view of a the device of FIG. 24 in unfolded, pre-used position.

FIG. 33 provides an exploded view of the disposable nature of the overall device 310 with the barrel 312 including the opening 326, opposing circular rotating cavities 324, circular aligned connection with the handle 364, the slide grip 318, the slide grip access and path opening 317 and a closed stylet point protective arm 350. Additionally, there is present the handle 314, with the switch 322, and complementary circular cavity 366 for rotation purposes, and, separately, the connection hub 316, that is removable to allow for such barrel 312 and handle 314 separation. The barrel 312 with the stylet point therein may be disposed of as a "sharp" within an appropriate container and the handle 314 and connection hub 316 may be disposed of in a standard rubbish bin or, if necessary, due to the potential for blood and/or other bodily fluid(s) thereon after utilization, may be disposed of within a suitable biohazard container. In any event, such separability, easily attained through the disconnection and disengagement of the connection hub 316 accords such beneficial results.

FIGS. 35-39 and 45 show another potentially preferred embodiment of the disclosed passive safety intraosseous device. The device 400 includes a barrel 412, a handle 414, a connection hub 416, a drill switch 420 on the barrel 412, a sled slide opening 417, slide grips 418, a barrel opening 426, a bottom handle foot 417, and a battery removal door 415 at the bottom of the handle. The device in FIG. 35 is shown with the handle 414 and barrel 412 in stowed (folded) position with the end of the handle 414 covering and facing most of the barrel opening 426 (and the bottom handle foot 417 facing outwardly. As the handle 314 and barrel 312 and unfolded, as in FIGS. 36 and 37, the drill switch 420 is made available (in this embodiment it is present on the barrel 412) and the connection 424 between handle 414 and barrel 412 is shown as well. FIG. 37 thus further shows the extension of the stylet 430 and cannula 428, as well as the cannula hub 434, through the barrel opening 426, thus allowing for the device 400 to be in ready-to-drill state. The bottom handle foot 417 is flat with, in this embodiment, a rounded triangular shape (of course, if desired, such a shape may be of any geometric type, including rounded, ovular, squared, and the like) to accord, with the flat, planar structure of the battery removal door 415 of the handle 414, the ability for the device to stand hands-free on a flat surface, if desired.

Figures 38, 39:
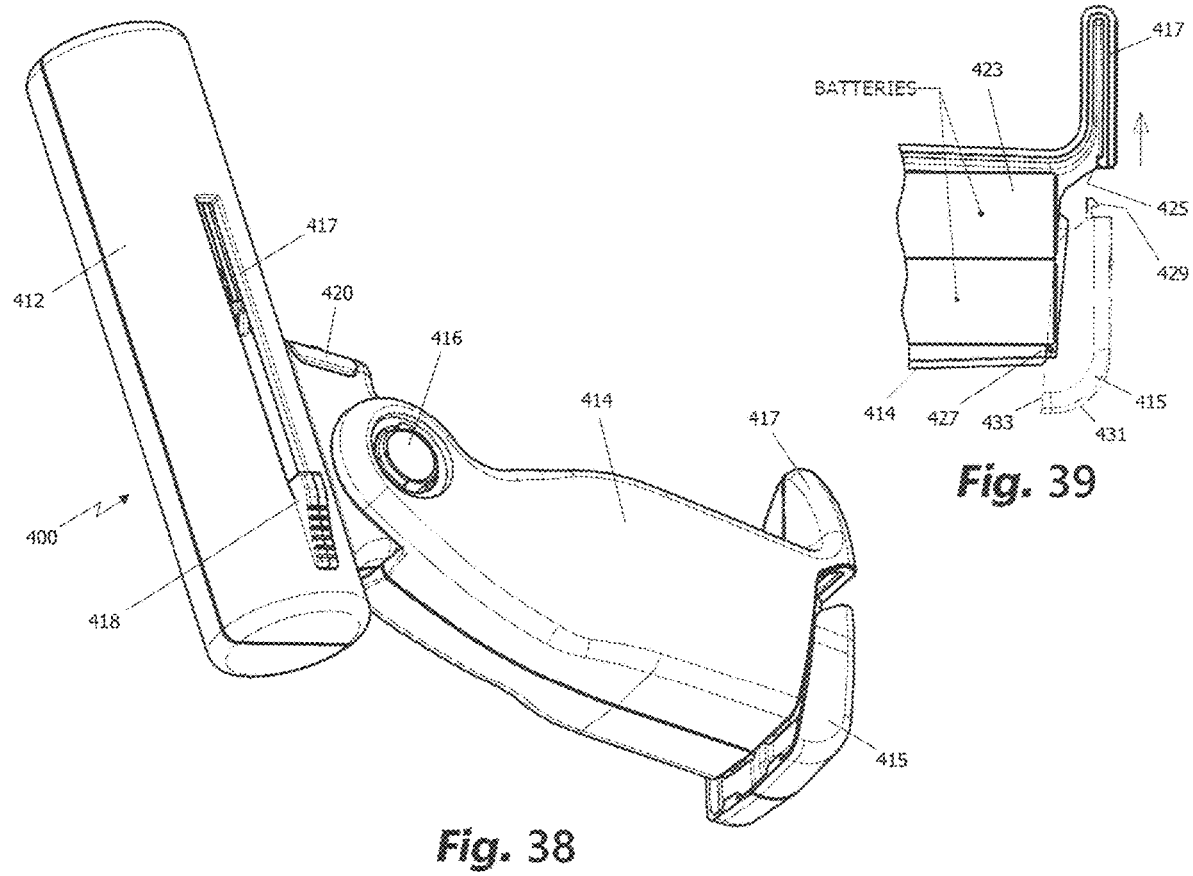
FIG. 38 is a rear perspective view of another possible embodiment of the overall device in unfolded state after use with cannula disengagement and motor and stylet retracted with the battery removal door opened.
FIG. 39 is a side cross-sectional view of a close-up of the battery removal door in opened state as in FIG. 38.
Figure 45:
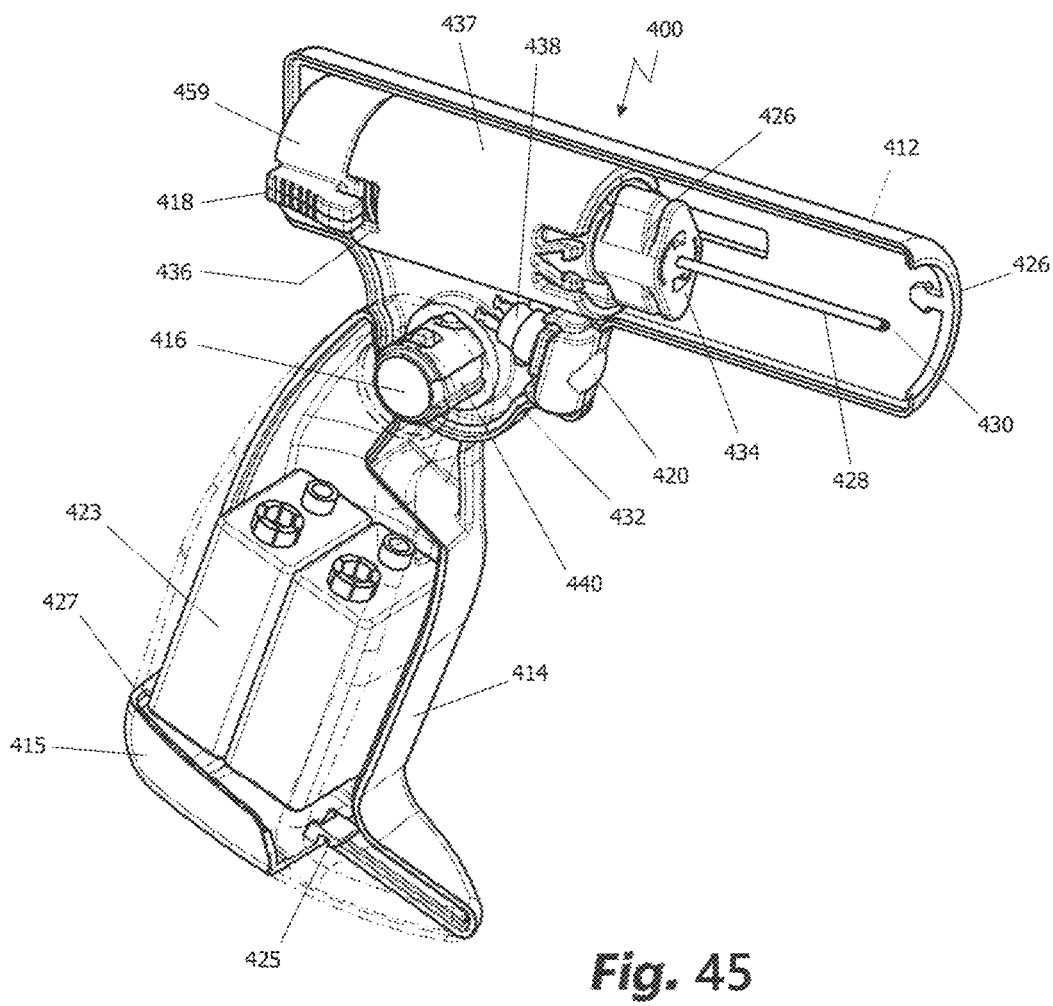
FIG. 45 is a cross-sectional side perspective view of another possible embodiment of the overall intraosseous device in unfolded pre-use state.

FIG. 37, again, shows the extension of the cannula 428 and stylet 430 for ready-to-use status of the device 400 with the slide grip 418 moved to the other end of the barrel housing 412 and the spring (such as 334 of FIG. 30) compressed as a result. FIG. 38 shows the device 400 in post-drill state with the cannula 428 and cannula hub 434 free from the stylet 430 as it has been retracted back within the barrel 412 (with, as before the integrated motor, such as 340 of FIG. 30, as well as the spring, such as 334 of FIG. 31, extended in reaction to the disengagement of the stylet 430 and cannula hub 434). The cannula 428 and cannula hub 434 would thus be maintained within a target patient's bone (such as 58 of FIG. 3) and the device then disposed of with the retracted stylet 430 passively moved and stored to prevent any further contact after removal from a patient's body. FIG. 45 shows the unfolded, prior-to-use status of the device 400 as above, with the batteries 423 shown as stored within the handle 414, with the cannula 428 and cannula hub 434 within the barrel 412 and the stylet 430 extending therefrom but also permanently attached to the motor and covered internally with a heath 437 to add in reducing moisture ingress within the barrel 412 and protection of the motor at least. Also shown is a rear gearbox cover attached to the slide grip 418 and attached to the spring 436, as well. The switch 420 further shows a contact 438 to maneuver upon compression of the switch to further create the needing conduction of electricity as needed for motor activation and operation on demand. itself FIG. 38 shows a rear perspective view of the post-use unfolded state of the device 400 of FIGS. 35-37 with the sled grips 418 returned in rear position on the barrel 412 subsequent to stylet/motor retraction. Prior to disposal thereof, then, the battery removal door 415 is disengaged to permit such battery access. FIG. 39 shows a close-up cross-sectional side view of the lower handle 414 and battery removal door 415 as well as the bottom handle foot 417. The door 415 is provided with a rounded bottom edge 431 to allow for gripping by the user with a tab/snap connector 429 at the front thereof that is complementary in shape to a extension 425 within the internal portion of the bottom handle foot 417. The handle 414 includes a further internal extension 427 to connect with an opening 433 above the rounded edge 431 as they are, as well complementary in shape. The batteries 423 (such as, as noted above, two lithium 9-volt batteries) are thus accessible for simple removal on demand and the door 415 may be replaced thereafter with reconnection of the tabs and extensions 433, 427, 429, 425.

FIG. 40 provides an exploded view of the disposable nature of the overall device 400 of FIGS. 35-39 with the barrel 412 including the opening 426, a circular aligned connection with the handle 430, the slide grip 418, the drill switch 420, and the slide grip access and path opening 417. Additionally, there is present the handle 414 with battery removal door 415 and bottom handle foot 417, as well as a complementary circular cavity 432 for rotation purposes, and, separately, the connection hub 416, that is removable to allow for such barrel 412 and handle 414 separation. The barrel 412 with the stylet point 430 therein may be disposed of as a "sharp" within an appropriate container and the handle 414 and connection hub 416 may be disposed of in a standard rubbish bin or, if necessary, due to the potential for blood and/or other bodily fluid(s) thereon after utilization, may be disposed of within a suitable biohazard container. In any event, such separability, easily attained through the disconnection and disengagement of the connection hub 416 accords such beneficial results. In this embodiment, it is also noticed that the connection hub 416 includes a surface extension 429 to prevent movement of the hub 416 from the aligned circular openings 430, 432 of the barrel 412 and handle 414, respectively, until the user manipulates the connection hub 416 through depression (or compression) of a pressure tab 439 externally. Such may be undertaken through pressing the connection hub 416 inward on either side of the handle 414 or barrel 412 when in an unfolded state and then turning the connection hub 416 to maneuver the tab extension 429 from a detent within the handle opening 432 and/or barrel opening 430. In any event, this allows for both rotation of the barrel 412 and handle 414 on demand, full ex FIG. 43 tension to a "locked in" position (and thus free-standing device on a flat surface, if desired), and eventual facile separation of handle 414 and barrel 412 for disposal purposes.

Figure 41A:
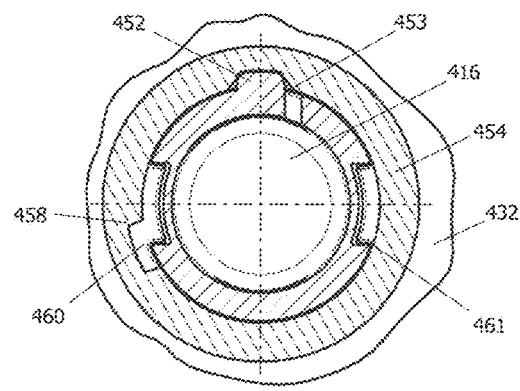
FIG. 41A is a close-up perspective view of the rotating connector hub of FIG. 41.
Figure 41:
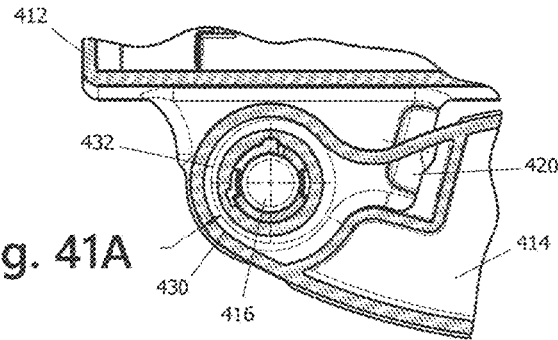
FIG. 41 is a close-up cross-sectional side perspective view of the rotating connector hub between the barrel and handle of another possible embodiment of the overall intraosseous drill device in closed position.
Figure 42A:
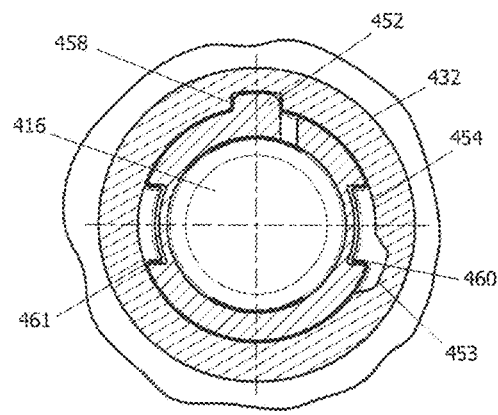
FIG. 42A is a close-up perspective view of the rotating connector hub of FIG. 41.
Figure 42:
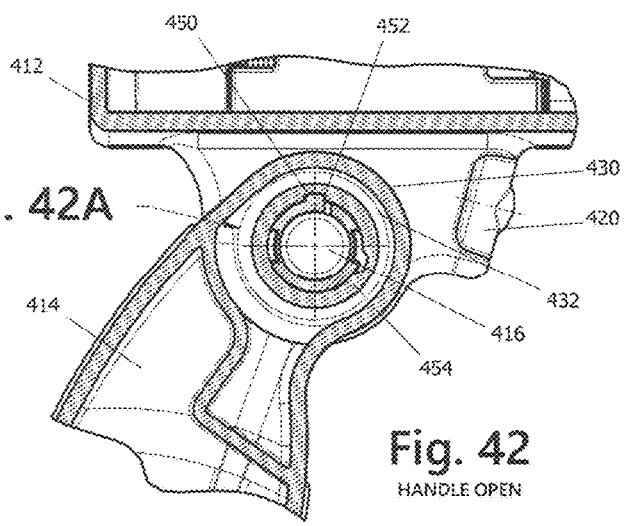
FIG. 42 is a close-up cross-sectional side perspective view of the rotating connector hub between the barrel and handle of another possible embodiment of the overall intraosseous drill device in open position.

FIGS. 41, 41A, 42, and 42A provide a close-up side cross-sectional view of the connection hub 416 and the circular openings 430, 432 of the handle 414, and barrel 412. In stowed, folded, position, as in FIG. 41, the connection hub 416 is present in a certain disposition. Such a hub 416 actually remains in a static state as, in FIG. 42, the handle 414 is rotated to an open, unstowed position with the inner handle circular opening portion 454 rotated as the barrel opening 432 remains static. The hub (or otherwise referred to as pin herein) 416 includes indentations 460, 461 on opposing sides as well as a spring nub (extension) 452 at the top thereof. The inner handle circular opening portion 454 includes two indentations 453, 460, as well, that are complementary in shape to the spring nub 452. As shown in FIGS. 41 and 41A, the handle 414 and barrel 412 are folded up in stowed formation with the inner handle circular opening portion 454 in its own stowed configuration and position with the first indentation 453 aligned and nested with the hub spring nub 452. The spring nub 452 is configured itself to press down and with the inclined side of the first inner handle circular opening indentation 453 as it is provided, is able to slide thereunder to allow the circular opening portion 454 to rotate from its initial folded, stowed position. Thus, in FIGS. 42 and 42A, the inner handle circular opening portion 454 has rotated about, in this embodiment about 110 degree from its stowed position, thereby aligning with the spring nub 452 and engaging the same with the second indentation 460 to lock (at least temporarily) therewith the nub 452. In this manner, only with a sufficient amount of pressure applied to the connection hub 416 and thus the spring nub 452 will the handle 414 disengage from such a "locked" unfolded state and allow the handle 414 and barrel 412 to return, at least to a certain degree, back to folded state on demand. Again, as noted above and further herein, the ability to prevent full re-closing (folding back) of the device is preferable as a proper indicator as to the use status of the device itself. If it cannot refold, it would be considered "spent" and thus ready for dismantling and disposal as needed. The frictional properties of the inner handle circular opening portion 454 as it rotates is sufficient, as well, to retain the unfolded state of the device at any angle measure between full open (such as, again, about 110 degrees from folded state) to at least about 20 degrees thereof from folded state. In this manner, as shown, for instance in FIG. 60, the device may stand alone, hands-free, on its flat bottom handle surface to allow for, at least, and if present within such an embodiment, a flash light article to help the user with visibility, if needed. If also allows for facilitation of location of such a device, whether lit or not, in a darkened space after drilling operation has occurred.

Figure 43:
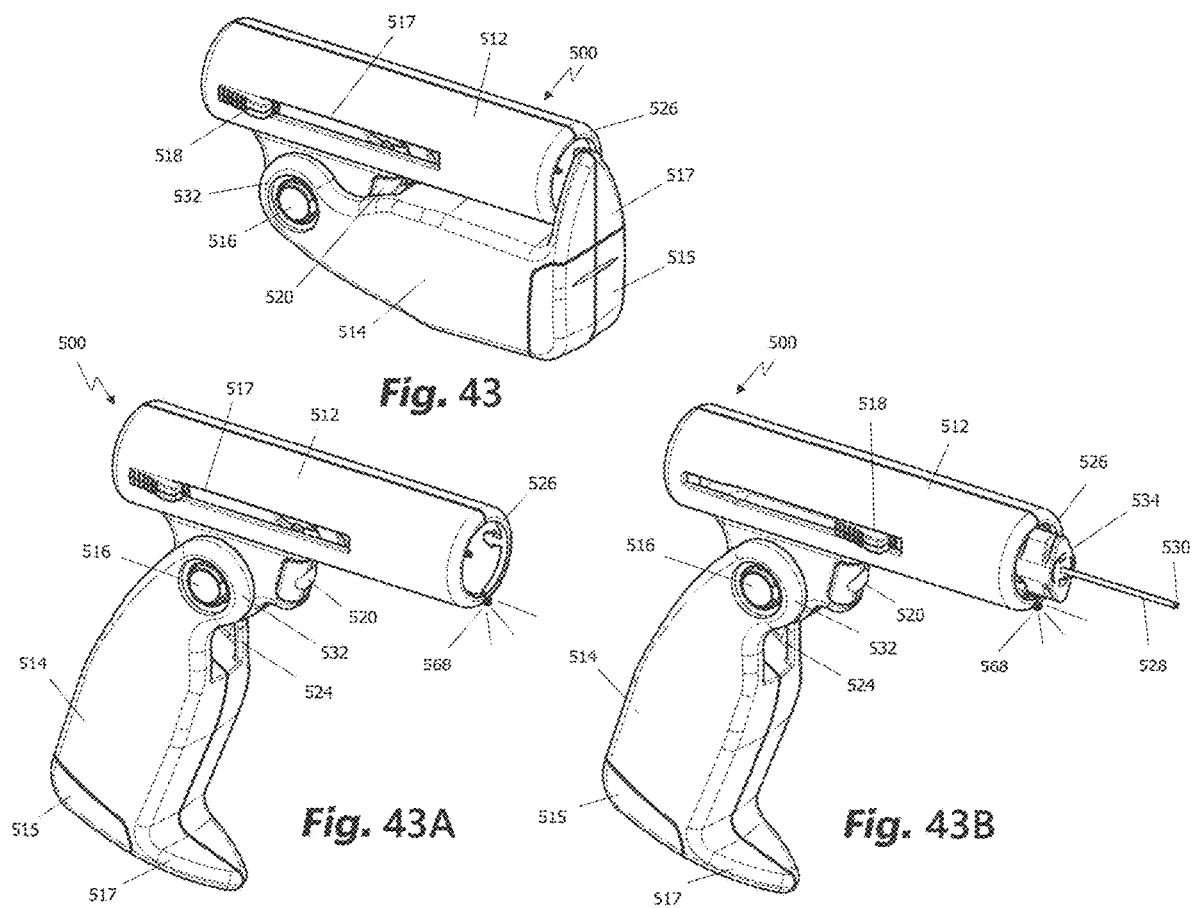
FIG. 43 is a side perspective view of another possible embodiment of the overall device in folded pre-used state including a light and control switch on the barrel.
Figure 44:
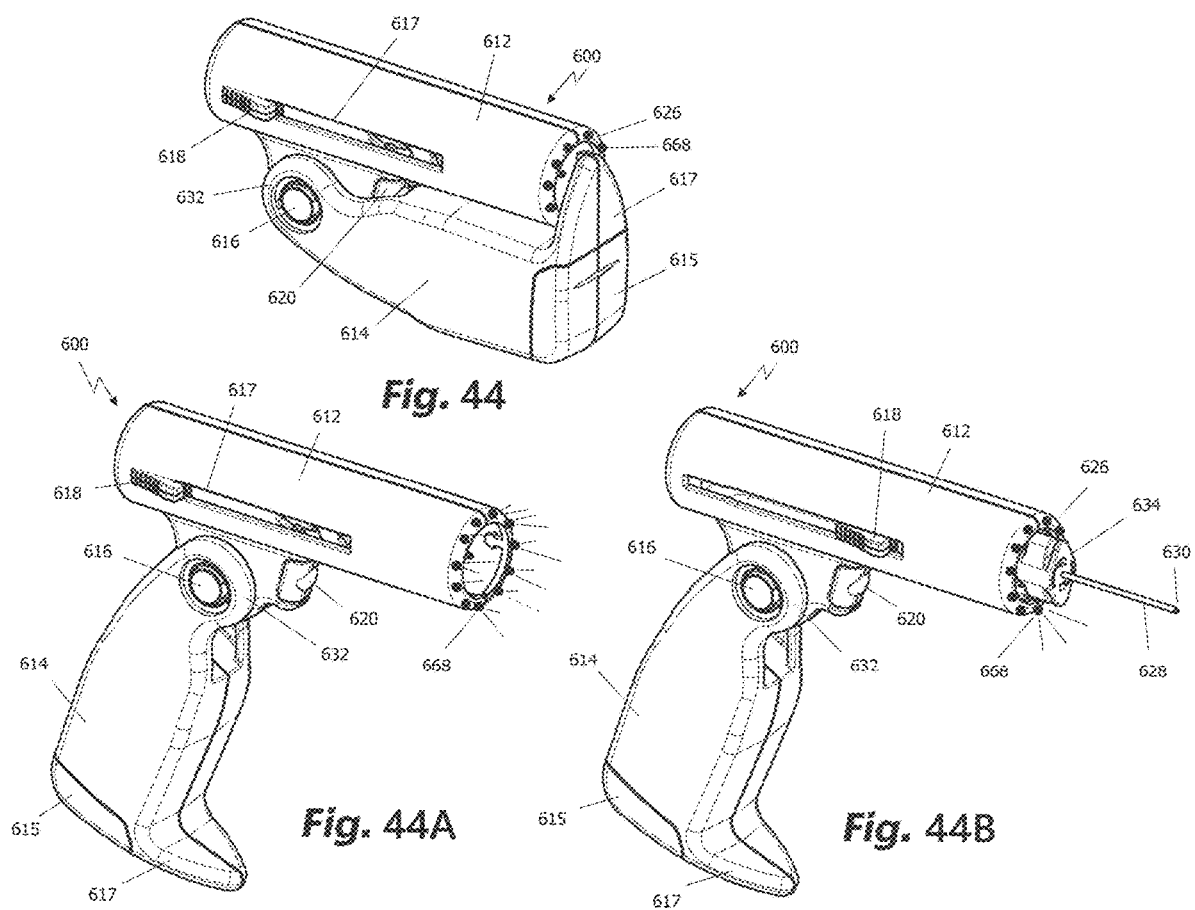
FIG. 44 is a side perspective view of another possible embodiment of the overall device in folded pre-used state including a light array around the barrel opening and a control switch also present on the barrel.

FIGS. 43, 43A, and 43B, as well as FIGS. 44, 44A, and 44B, show different potentially preferred embodiments of a disclosed intraosseous device with different lights included to both aid the user in undertaking a drilling activity, particularly in dark, low visibility conditions, as well as subsequently thereto, and upon retraction of stylet/motor within the device and implantation of cannula/needle within a target patient's bone, as a type of standalone flashlight, if necessary and/or desired. FIGS. 43-43B show a light 568 supplied within the device 500 that further includes a barrel 512, a handle 514, a connection hub 516, a drill switch 520 on the barrel 512, a sled slide opening 517, slide grips 518, a barrel opening 526, a bottom handle foot 517, and a battery removal door 515 at the bottom of the handle. The device in FIG. 43 is shown with the handle 514 and barrel 512 in stowed (folded) position with the end of the handle 514 covering and facing most of the barrel opening 526 (and the bottom handle foot 517 facing outwardly). As the handle 514 and barrel 512 and unfolded, as in FIGS. 43A and 43B, the drill switch 520 is made available (in this embodiment it is present on the barrel 512) and the connection 524 between handle 514 and barrel 512 is shown as well. As the device 500 is thus unfolded, the light 568 automatically activates, thus providing a means for visibility, as well as a way of indicating the power within the device 500 is functioning properly for drilling purposes. FIG. 43B thus further shows the extension of the stylet 530 and cannula 528, as well as the cannula hub 534, through the barrel opening 526, thus allowing for the device 500 to be in ready-to-drill state; with the light 568 shining, the user, again, knows the power is sufficient for drilling and also has, again, a means to light the desired drilling location as needed. The bottom handle foot 517 is flat with, in this embodiment, and as above, a rounded triangular shape to accord, with the flat, planar structure of the battery removal door 515 of the handle 514, the ability for the device to stand hands-free on a flat surface, if desired, particularly subsequent to drilling to permit a user hands-free utilization of the flash light capability of the device 500 thereafter.

FIGS. 44, 44A, and 44B are similar to FIGS. 43-43B except in this embodiment there is in place a full array of lights 668 around the periphery of the barrel opening 626. Certainly, as alluded to above, such an array may be anywhere from 2 to as many as 12 lights, if desired (although with 2, one may be on the bottom and one at the top of the periphery, with 4 in each cardinal location thereof, etc., and provide sufficient and proper lighting and indications of power generation for the user). In this situation, the same basic device 600 is provided with a barrel 612, handle 614, battery removal door 615, bottom handle foot 617, slide opening and spring 617, slide grips 618, connection hub 616, handle connector 632, barrel drill switch 620, and barrel opening 626. When unfolded, as above, the lighting array 668 activates for visibility and power indication for the user; upon extension through movement of the slide grip 618 towards the front of the barrel housing 612, the cannula 628, with hub 634, and stylet 630 extend as well for drilling access. As with the other embodiments noted above, the extension of the cannula 628 and stylet 630 provides a for ready-to-use status for the device 600 with the slide grip 618 moved to the other end of the barrel housing 612 and the spring (such as 334 of FIG. 30) compressed as a result. Similar to that shown in FIG. 38, above, subsequent to drilling, the stylet/motor retracts leaving the cannula within a target patient's bone, and the device ready for disposal thereof, again, as noted above.

Figure 46:
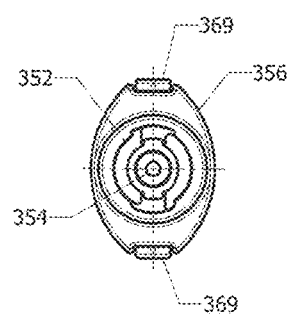
FIG. 46 is an aerial view of a potential embodiment of a recessed cannula hub in oval shape with wing flaps.
Figure 47:
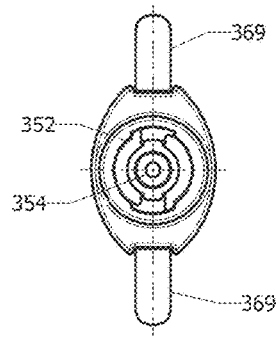
FIG. 47 is an aerial view of the hub of FIG. 46 with the wing flaps open.

FIGS. 46 and 47 provide aerial views of one possible embodiment of a cannula hub in oval-like shape. The hub includes grip sides 356 with stowed wing blades 369. Centrally located are the cannula opening 354 and the stylet and/or IV (or other connection) opening 352. In FIG. 47, the wing blades 369 are unstowed, particularly after introduction within a target patient's skin and bone, in order to allow for tape-down thereof for a more secure introduction of the cannula as needed. Certainly, as noted above, the cannula hub may be of any geometric shape and the wing blades may as well. This embodiment merely shows one potential manner of supplying such appendages to the cannula hub for tape-down, etc., purposes.

Figure 48:
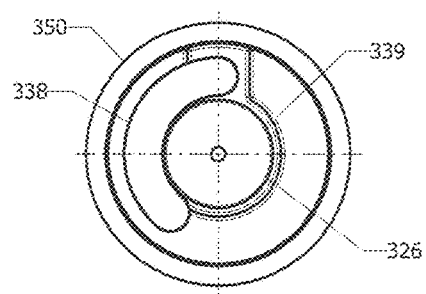
FIG. 48 is a front view of an open barrel embodiment with a stowed stylet protective arm and stowed internal film.
Figure 49:
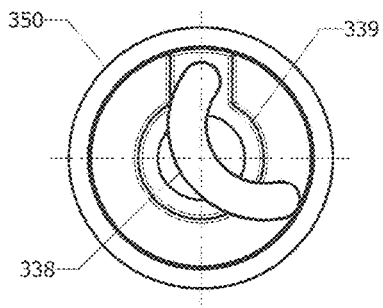
FIG. 49 is a front view of the open barrel embodiment of FIG. 48 with activated/unstowed stylet protective arm and internal film.

FIGS. 48 and 49 show a close-up of a potential embodiment of a barrel opening 326 (as in FIG. 33) including a stowed stylet point protective arm 338 that extends, in FIG. 49 half way within the opening 326 to cover the stylet point (330 of FIG. 31, for instance) after retraction thereof. Also included, as another added benefit, and in order to potentially protect a user from not only the stylet point, but any possible fluids brought within the barrel opening 326 upon retraction, is a spreadable cover film 339 that stows along the sides of the barrel 350 prior to retraction of the motor/stylet. Once retraction occurs, the film moves with the arm 338 to cover the portions of the opening 326 not covered by the arm 338. Other embodiments allow for further covers, doors, and the like, as alternatives to this possible variation as well.

Figure 50:
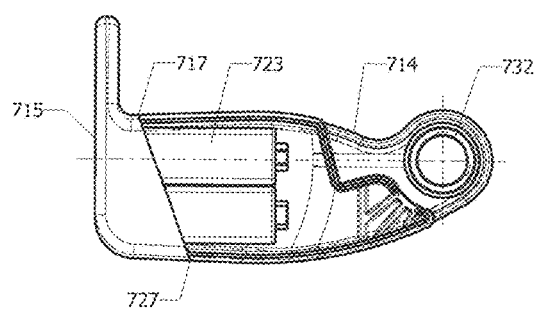
FIG. 50 is a cross-sectional side view of a possible handle embodiment of the overall intraosseous device with a battery removal door having a living hinge on the rear handle portion in closed state.
Figure 51:
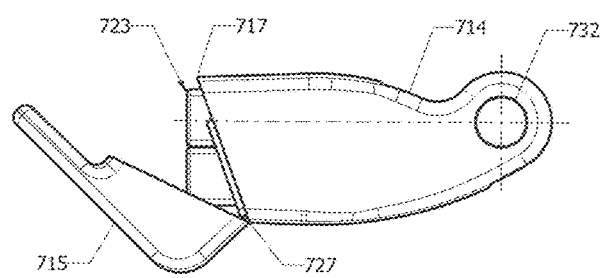
FIG. 51 is a cross-sectional side view of the handle of FIG. 50 having a battery removal door with the living hinge in open state.
Figure 52:
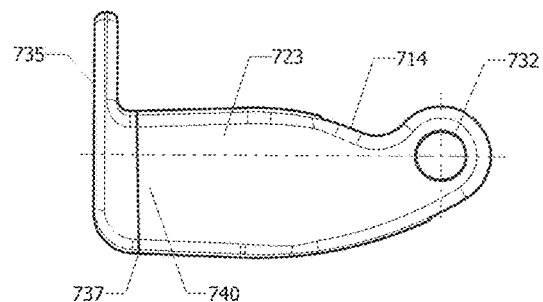
FIG. 52 is a cross-sectional side view of a possible handle embodiment of the overall intraosseous device with a battery removal door having a living hinge on the bottom portion in closed state.
Figure 52A:
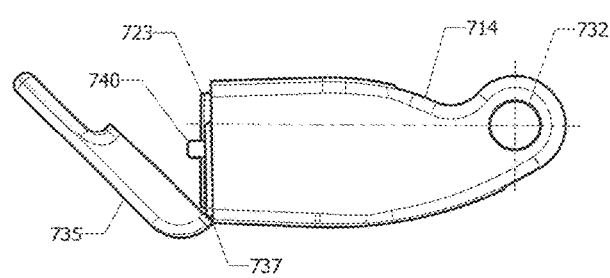
FIG. 52A is a cross-sectional side view of the handle of FIG. 50 having a battery removal door with the living hinge in open state.

FIGS. 50, 51, 52, and 52A show alternatives to the battery removal door shown above, particularly as a means to allow for disposability of fully connected parts that would be unitary n nature as disposed of together. As shown above, a removable battery door (415 of FIG. 45, for instance) may be employed and allows for access to batteries for removal and disposal separately as needed. Such a door, however, in the user's haste, may be thrown away separately, leaving such disposability of more than one part. If such a device is particularly stained or contaminated with body fluids, etc., of a target patient, the ability to ensure limited numbers of such device parts are placed in necessary containers, etc., for safety purposes would be potentially important. As such, and merely as potential embodiments of such single structure items, disposable handles 714 with connection hub openings 732 are shown within such FIGS. 50-52A as including living hinge battery removal openings. In FIGS. 50 and 51, the door 715 has a rear handle placed living hinge 727 that allows for disengagement at the lower front of the handle 717 and lower rotation to allow unfettered access to the batteries 723. In this manner, the height of the opening 715 allows for easy grasp of such batteries 723 (again, preferably here lithium 9-volt types) on demand for removal. In FIGS. 52 and 52A, the door 735 is at the bottom of the handle 714 and the living hinge 737 is present at the lower rear portion of the handle 714, thus allowing for opening of the full bottom of the handle 714 at a lower rear point. This allows for battery 723 access, certainly, with the further possibility of utilizing a drape fabric 740 (or plastic, as desired) to provide further capability of pulling down on the batteries 723 for removal, if needed. Certainly, as noted above and herein, such batteries may be stowed within the handle with the ability for wires attached through snap-on contacts that can themselves extend upon opening of such doors (since the batteries 723 rest on the doors themselves) and the batteries 723 may thus simply be removed from such contacts and removed. In either situation herein, the doors 715, 735, may be closed after battery removal, or left open. Being connected of the handle 714, such doors 715, 735 are thus part of a unitary structure for proper disposal purposes after battery removal.

Figure 53:
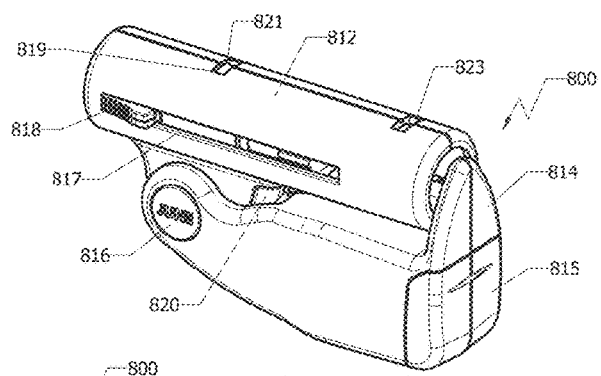
FIG. 53 is a side perspective of another possible embodiment of the intraosseous device with a top barrel side status indicators and a light in a folded pre-use state.
Figure 54:
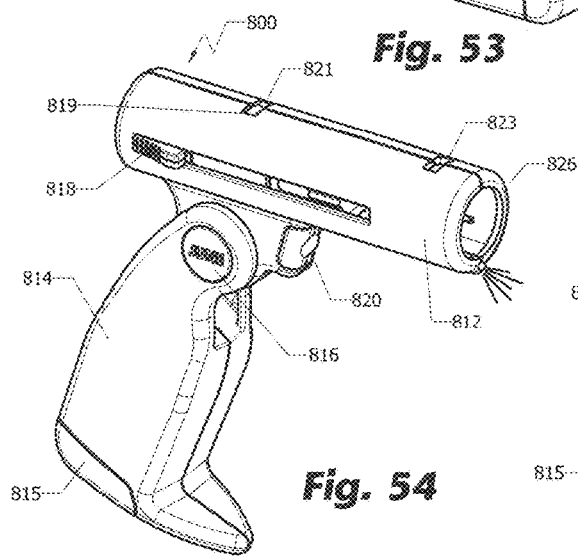
FIG. 54 is a side perspective view of the device of FIG. 53 in an unfolded pre-use state with the light automatically activated.
Figure 55:
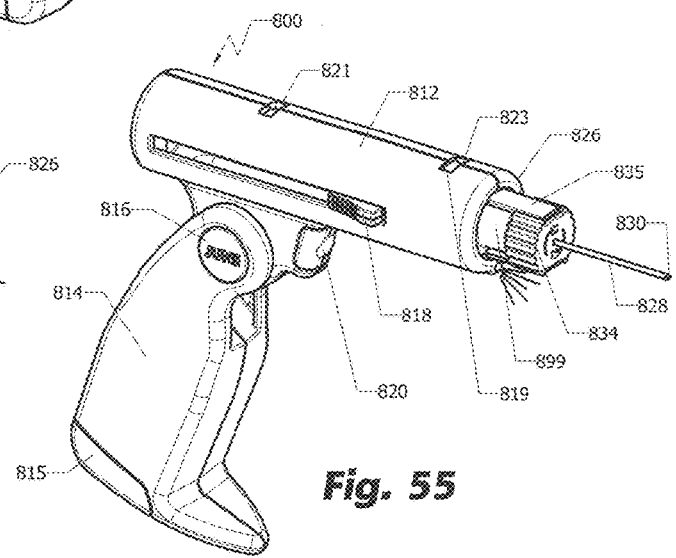
FIG. 55 is a side perspective view of the device of FIG. 54 in unfolded, ready-to-use state.
Figures 62, 63:
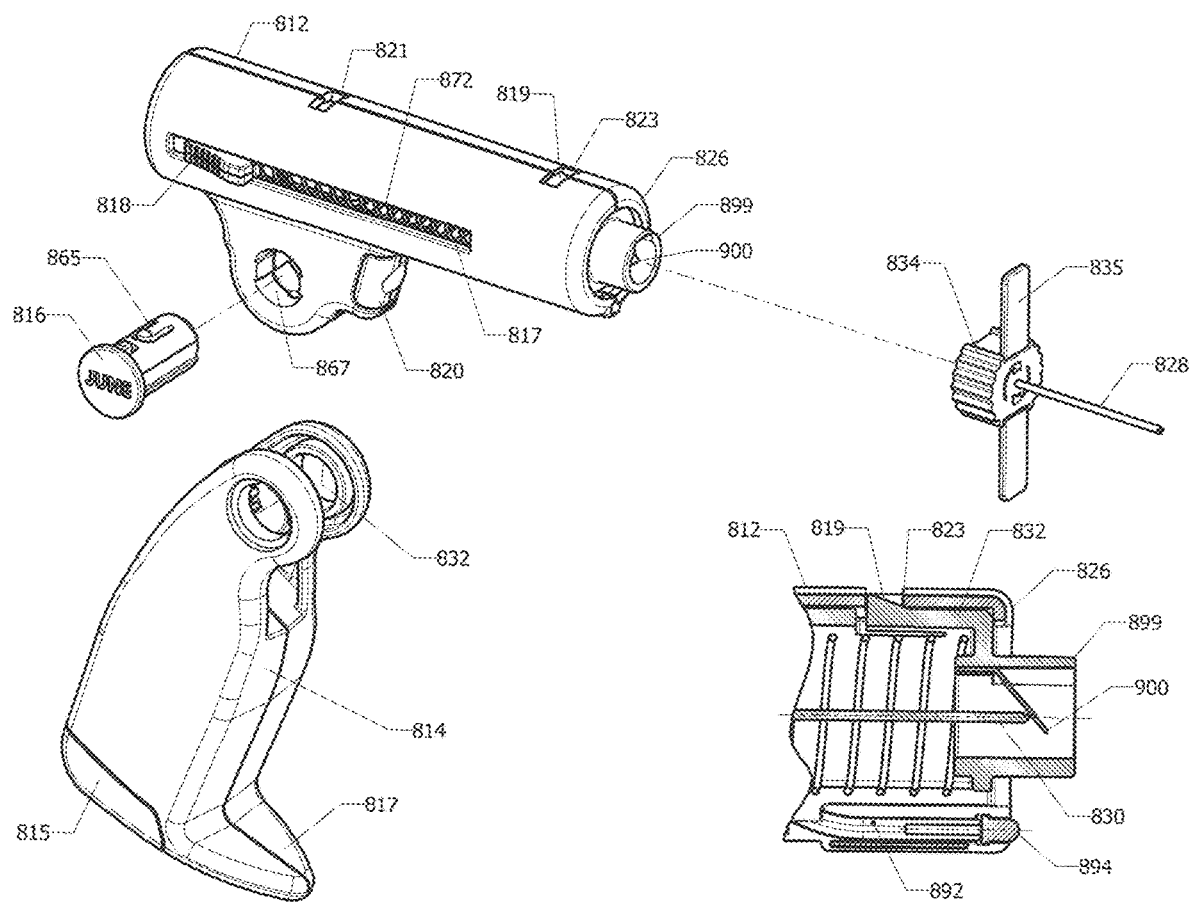
FIG. 62 is an exploded front side perspective view of the device of FIG. 55 after use with the cannula and hub separated for placement within a patient bone and the handle and connector hub detached from the sharps-containing barrel.
FIG. 63 is a side cross-sectional view of the barrel end of the device of FIG. 62 with the protective extender cap including a door cover over the retracted stylet point.

FIGS. 53, 54, and 55 provide a device 800 with a number of different structural components for another potentially preferred embodiment. In this alternative, an intraosseous device 800 is provided with a barrel 812, handle 814, battery removal door 815, bottom handle foot 817, slide opening and spring 817, slide grips 818, connection hub 816, barrel drill switch 820, and barrel opening 826. Additionally, as shown in FIG. 55, there is an extended motor/stylet housing 899 for at least space to grasp the cannula hub 834 during use. The cannula hub 834, further includes wing blades 835 and the device includes a light 894 in the barrel opening 826. Additionally, the extended motor/stylet housing 899 includes a top-disposed tab 819 that resides within a rear-disposed barrel top opening 821 when stowed prior to extension of the motor/stylet/cannula and slides with the motor/stylet/cannula upon grip slide 818 movement towards the from the barrel housing 812. The top-disposed tab 819 then moves to a front-disposed barrel top opening 823. The tab 819 is structured with a flat side disposed at the rear portion thereof and an incline leading downward to the front portion thereof. This structure allows for the rear tab portion to lock in place within the front-disposed barrel top opening 823 and slide forward from the rear-disposed barrel top opening 821 upon movement of the slide grip 818 and slide compression 817. In this manner, the extended motor/stylet housing remains in place as it is extended even after retraction of the motor/stylet subsequent to drilling operation. As shown in FIGS. 60, 61, and 62, for instance, the extended housing 899 remains outside the barrel opening 826 when and after retraction occurs. As in FIG. 61, then, the extended housing 899 prevents re-closing of the handle 814 and barrel 812 together, indicating the device has been "spent" and disposal is needed at that time. The housing tab 819 further provides indication of a "spent" device as the user may view the presence of the tab within he front-disposed barrel top opening 823 as such a communication that the device has been utilized (particularly if no cannula and/or hub are present external the barrel simultaneously as being checked). As noted above, the openings 821, 823 may be provided with color coding, or working, etc., as desired, as an explanation as to the status of the device, with the presence of the tab 819 within the rear opening 821 indicating ready-to-use, and, again, in the front opening 823, denoting a "spent" device and need for disposal thereof properly. In any event, as above, for FIGS. 44-44B, for example, the lighting array 868 activates for visibility and power indication for the user when the handle and barrel are unfolded (even to just a minimal rotational distance, such as, for example, about 20 degrees from stowed state, to full extension). When fully extended, and thus ready to activate the drill component, the slide grip 818 may be maneuvered along the spring opening and guide 817 towards the front of the barrel housing 812, thus moving the motor/stylet/cannula component 828.830, with wing-bladed hub 834, outwardly for drilling access. As with the other embodiments noted above, the extension of the cannula 828 and stylet 830 provides a for ready-to-use status for the device 800 with the slide grip 818 moved to the other end of the barrel housing 812 and the spring (such as 334 of FIG. 30) compressed as a result. Similar to that shown in FIG. 38, above, subsequent to drilling, the stylet/motor retracts leaving the cannula within a target patient's bone, and the device ready for disposal thereof, again, as noted above. Certainly, it should be well understood that such an embodiment may also include a light or light array as described herein, if desired, thus allowing for the full utilization of such an internal housing extender with a cannula hub, etc., for improved grasping and visibility, as desired.

Figures 56, 57:
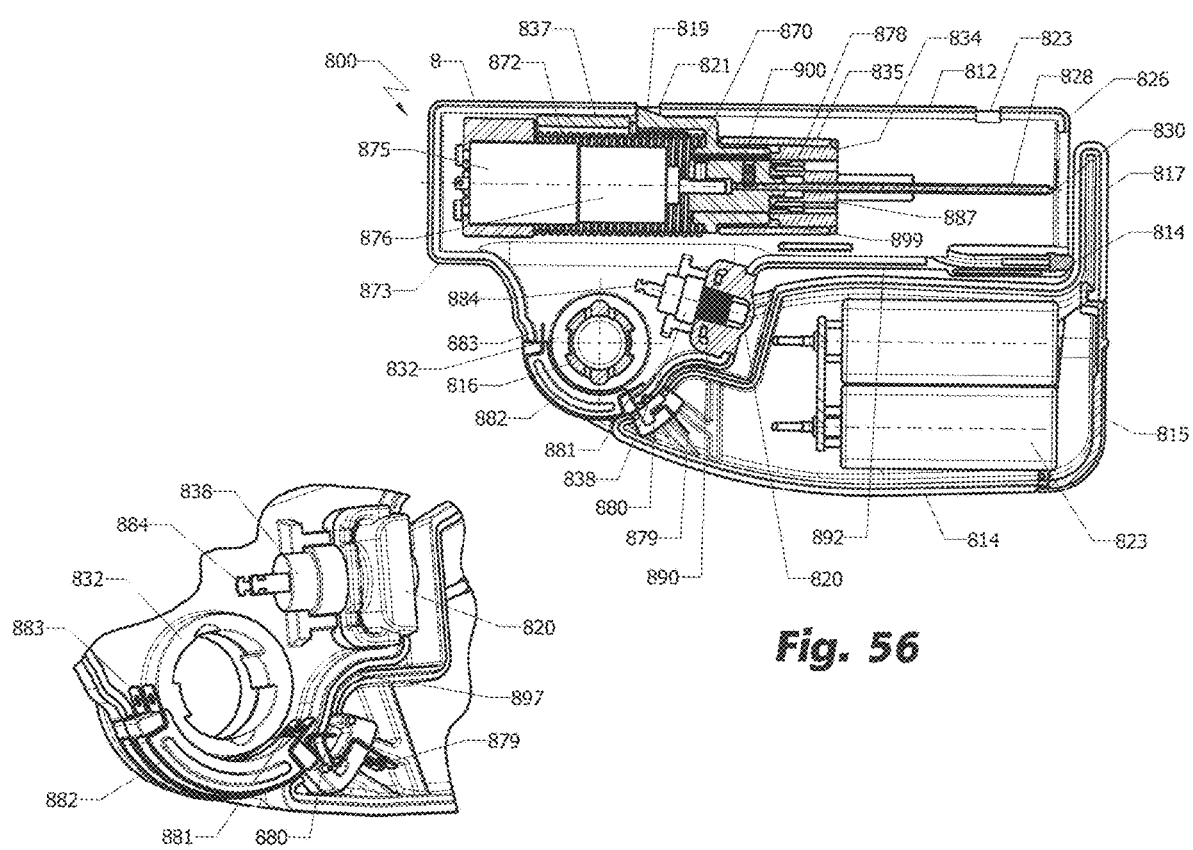
FIG. 56 is a side cross-sectional view of the device of FIG. 53 in folded pre-use state.
FIG. 57 is a front side perspective cross-sectional view of the connector hub electrical components of FIG. 56 in folded pre-use state.
Figures 58, 59:
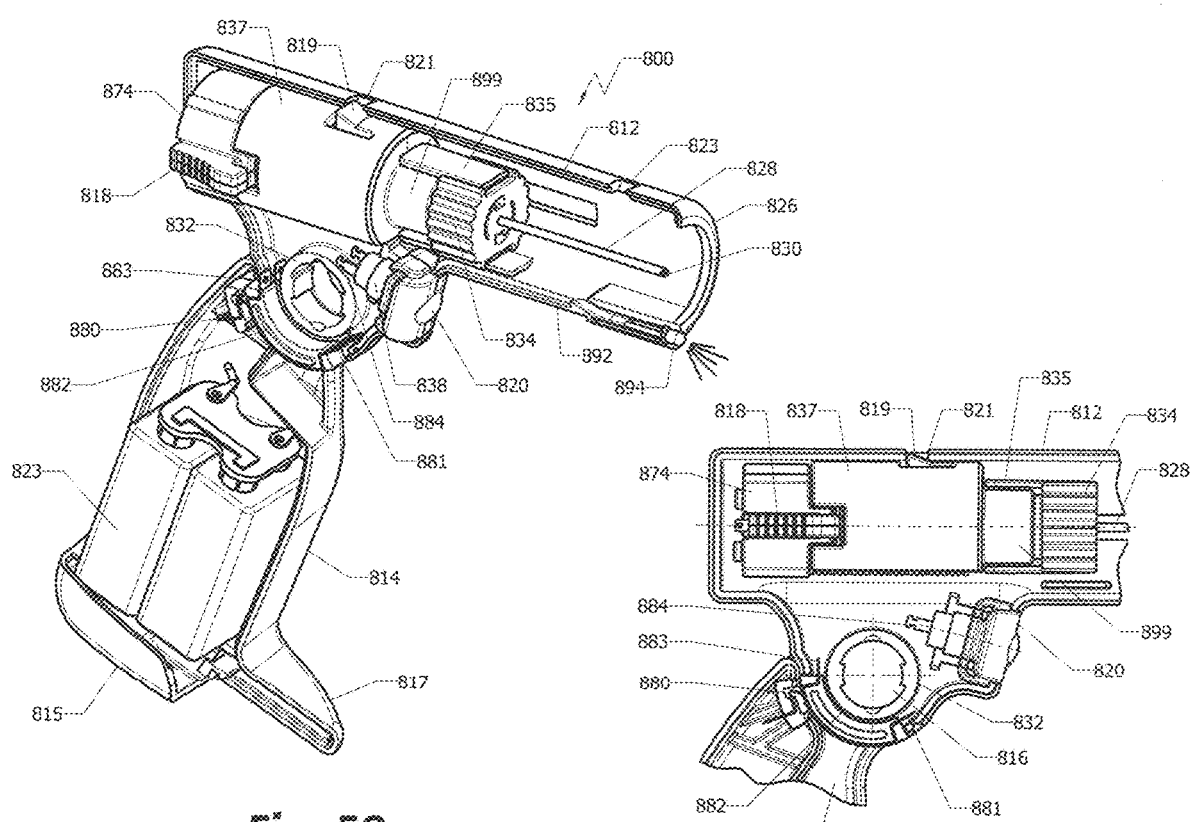
FIG. 58 is a side perspective cross-sectional view of the device of FIG. 54.
FIG. 59 is a side perspective cross-sectional close-up view of the rear portion of the barrel and connector hub of the device of FIG. 53 in folded, pre-use state.

FIG. 56 shows a full cross-sectional side view of a potentially preferred embodiment of the disclosed intraosseous device with a closer view of the electrical configurations therein. The device 800 includes a light 894 with a wire 892 leading to a barrel contact 881. The handle 814 includes batteries 823 (preferably, as previously noted, 9-bolt lithium batteries) that supply power to an internal handle contact 879 that is attached to a electrical contact plate 880 for rotational contacting with the barrel contact 881. The electrical conductance from the handle 814 (and thus batteries 823) through the handle contact 879 and plate 880, occurs upon such rotational movement (unfolding) of the handle 814 from the barrel 812. In FIG. 58, the full unfolded state of the device 800 is shown, with the light 894 automatically activated upon electrical conductance initiation. FIG. 60 thus indicates that such conductance may be achieved at 20 degrees from folded state of the device 800 and FIG. 58 indicates full unfolding (up to about, for instance 110 degrees from folded state) with the light 894 activated and the device 800 in ready-to-use state prior to extension of the motor/stylet/cannula for drilling operations. In FIG. 56, the device 800 includes the drill switch 820 with connector component 838 and contact prongs 884 for wire engagements. As noted above, the light wire 892 connects at the barrel contact 881 and leads through the switch 820 but is not activated by the switch 820 at all, only upon electrical conductance from the handle contact 879 and plate 880 to the barrel contact 881 and thus the light wire 892. Additionally, a curved contact 881 is situated within the barrel 812 to lead between barrel contacts 881, 883 for continuous electrical conductance when properly aligned with the handle contact 879 and plate 880. The handle 814 includes a battery removal door 815 for disposal of the batteries 823 when needed as well as the bottom handle foot 817 at the front thereof to aid in stabilized stand-alone status of the device (as in FIG. 60, for instance. The device 800 includes a connection hub 816, as above, for such a rotational benefit (to allow for folded and unfolded statuses of the device 800) as well as to separate the barrel 812 from the handle 814 for disposability, again, when needed. The switch 820 activates electrical conductance from the barrel contacts 881, 883 to the motor wire 873 that leads to the motor 876 with the stylet base 870 permanently attached thereto and leading to the stylet 830 extending from the cannula 828. The cannula hub 834 is contacted, temporarily, with the stylet 830 through arms 878 aligned with openings 887 in the hub 834. The motor 875 is connected with a rear gear box 875 and all of the gear box 875, motor 876, and stylet 830 are not only integrated together as a single unit, but are covered by an internal housing 837 that has a peripheral edge 899 that contacts the bottom edge of the cannula hub 834 (in this embodiment) and further includes an automatically pivoting cover/door 900 (that covers the stylet 830 after retraction as shown in FIG. 61, as one example). Additionally, the internal housing 837 includes a top positioned tab 819 that is inclined with a rear-facing flat surface and aligns with the barrel top openings 821, 823, as noted previously. In FIGS. 56, 58, and 59, the tab 819 is aligned in the rear tab barrel top opening 821, awaiting movement with the extension of the motor/stylet/cannula through the slide grip 818 manipulation outwardly from the barrel opening 826. The internal housing extender 837 prevents further movement of the motor/stylet thereunder as the extender 899 stops at the barrel opening 826 and the cannula hub 834 and cannula 828 (as well as the stylet 830 pre-retraction) are then accessible external of the device 800 for drilling purposes. The spring 872 thus allows for such retraction on disengagement of the cannula hub 834 and stylet base arms 878, as described in greater detail above. The cannula hub 834 further includes wing blades 835 folded thereon until unfolded (as in FIG. 62, for example). A spring 872 encircles the motor/stylet/gearbox 876, 830, 875 to retract the same assembly after drilling operation is complete (and the cannula 828 and hub 834 are introduced within a target patient's bone and the wing blades 835 are deployed on the patient's skin). FIG. 57 provides a rear perspective close-up cross-sectional view of the electrical components at the barrel 812 and handle 814 interface as described above. The switch 820 leads to a connector component 838 to wire connecting prongs 884. The handle includes a handle contact 879 and a contact plate 880 for connection with the barrel contact 881 that leads to the curved contact 882 and the further barrel contact 883 that is ultimately associated with the motor wire and (873 of FIG. 56, for instance) the controlling switch 820 for such drilling operation.

FIGS. 58 and 59 provide cross-sectional side views of the device of FIG. 56 in unfolded prior-to-use state. Thus, the same a potentially preferred embodiment of the disclosed intraosseous device 800 is shown with the light 894 activated due to the connection of handle contact 879 and plate 880 with the barrel contacts 881, 883 and curved contact 882 in response to the rotation of the handle 814 around the connection hub (pin) 816 in relation to the barrel 812. with a closer view of the electrical connections therein. The internal housing extender 839

FIG. 60 shows the functionality of a potentially preferred lighted intraosseous device subsequent to drilling operation as a free-standing flash light article. The spring 872 has expanded to deliver the motor/stylet automatically upon disengagement with the cannula hub and thus retraction has occurred (the slide grip 818 returns to its original position, as well along the slide opening 817). The internal housing extender 899 remains external the barrel opening 826, the internal housing tab 819 is present and engaged with the barrel top front opening 823 to ensure the housing (837 of FIG. 56, for instance) remains in place with the front extender 899 outside the barrel opening 826. The barrel 812 thus can rotate around the connection pin 816 with the user simply disengaging the spring nub (452 of FIG. 41A, for example) and moving the barrel 812 around such a pin in relation to the handle 814 which may be placed on a flat surface with the flat battery removal door 815 and the bottom handle foot 817 providing a reliable base for such a purpose. The rotation of the barrel 812 may be from full extension (unfolded state, again, roughly 110 degrees from folded state) to nearly closure (as shown in FIG. 61, the internal housing extender 899 prevents full closure thereof), as desired. With the electrical connections (handle contact 879 and plate 880 and barrel contacts 881, 882, 883) in place, the light 894 remains activated permitting utilization thereof as a flash light device itself; the flat surface placement allows for hands-free placement thereon and the rotation of the barrel 812 allows for directional provision of the light 894 as needed and/or desired for the user. Such rotation of the barrel 812 may be as low as, in this potential embodiment 20 degrees from folded state and still remain connected for electrical conductance from the batteries 823 to the light 894 for operation thereof. As noted above, FIG. 61 shows the fully retracted state of the motor 876, gearbox 875, and stylet 830 back within the barrel 812 with the internal housing cover 837 remaining at the front end thereof the barrel 812 with the internal housing top tab 819 secured within the barrel top front opening 823 to prevent movement of the internal housing 837 back as retraction occurs. Thus, the housing extender 899 outside the barrel opening 826 to prevent full closure of handle 814 bottom foot 817, for instance, back over the barrel opening 826 as originally provided prior to unfolding and drill operation. The spring 872 has thus extended back to its desired position to retract the internal components as noted and the housing extender cover 900 has closed over the stylet 830 automatically once the retraction step occurs to prevent any external contact with the stylet point 830 by the user or anyone else. FIG. 63 provides a closer view of the barrel opening 826 after retraction of the stylet 830 (and integrated motor, of course) with the automatic internal housing extender cover 900 deployed over the stylet 830, the internal housing top tab 819 locked within the barrel housing front top opening 823, the spring 872 extended for such retraction results, and, with the folding of the device in FIG. 61 undertaken past the threshold point for electrical conductivity to occur, the light 894 is no longer activated. Thus, both FIGS. 61 and 63 show a device ready to be disposed of properly subsequent to dismantling of the barrel 812 and handle 814 and connection pin (hub) 816. FIG. 62 provides such separation with the cannula 828 and cannula hub 834 with deployed wing blades 835 (for skin application while the cannula/needle is within the target patient's bone) and thus the retracted motor/stylet within the barrel 812 with the internal housing extender 899 in place at the barrel opening 826. Again, the internal housing top tab 819 provides both a manner of preventing retraction of the internal housing extender 899 back into the barrel 812 as well as an indicator that the device 800 has been "spent" in terms of drilling operations. The connection hub (pin) 816 is thus disengaged from both the barrel 812 and the handle 814 through pressing in thereof when properly aligned within the circular openings 832, 867 of the handle 814 and barrel 812, respectively and operating spring nub 865 as needed to maneuver the connection hub (pin) 816 from such aligned components 832, 867. Thus, upon such hub/pin 816 removal, the barrel 812 and handle 814 are separated and proper disposal may be undertaken of both (as well as the batteries within he handle battery removal door 815, of course).

With the disclosures set forth herein and above, an entire intraosseous device having full passive safety capabilities from initial transport, opening for use, unfolding, extension of stylet/cannula, drilling operation, retraction of stylet (with integrated motor) and thus placement of cannula within a target patient's bone, and separation and disposal of all device parts as needed is provided. A light display may be present for visibility and power generation indication purposes, and the device may be provided as a stand-alone light providing device for the user subsequent to drilling and with a light to aid in sight before and during such an activity, as well. Indications as to status of usability are provided, as well, and as needed, to ensure a user knows at all times whether a device is ready for use or not, too. In other words, a full consideration and provision of a passive safety inatraosseous device with numerous beneficial added implements, and all with a single-use fully disposable drill accords the emergency medical industry a long sought-after advancement that meets a plethora of needs and desires.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the description herein cover any and all such applications, modifications, and embodiments within the scope of the present invention.

What is claimed is:

1. A device for establishing access to an intramedullary space of a bone, said device comprising:
a housing having a first end defining a housing opening, a second end, and a wall defining a housing internal chamber and an elongate slide opening in communication with the housing internal chamber;
a handle;
a hinge connecting the housing and the handle and having a hinge axis, the handle movable about the hinge axis between a first handle position and a second handle position;
a power source;
a motor disposed within the housing internal chamber, the motor including a rotatable shaft and operably connected to the power source when the handle is in the second handle position;
a stylet attached to the shaft;
a slide grip connected to the motor and extending through the slide opening;
a switch adapted to activate the motor to rotate the shaft and the stylet; and
a cannula releasable disposed on the stylet;
wherein the motor, shaft, and stylet are movable within the housing internal chamber from a first position in which the stylet is disposed within the housing internal chamber to a second position in which the stylet extends through the housing opening; and
wherein the slide grip moves along the slide opening in a first direction as the motor, shaft, and stylet move from the first position to the second position and along the slide opening in a second, opposite direction as the motor, shaft, and stylet move from the second position to the first position.

2. The device of claim 1, wherein the handle extends alongside the housing when the handle is in the first handle position.

3. The device of claim 2, wherein the handle extends away from the housing when the handle is in the second handle position.

4. The device of claim 1, wherein the handle has a handle lengthwise axis and the housing has a housing lengthwise axis; and
wherein the handle lengthwise axis and the housing lengthwise axis are parallel when the handle is in the first handle position; and
wherein the handle lengthwise axis and the housing lengthwise axis arc not parallel when the handle is in the second handle position.

5. The device of claim 1, further comprising a housing extension releasably connected to the motor;
wherein the housing extension extends through the housing opening when the motor, shaft, and stylet are in the second position.

6. The device of claim 5, wherein the handle defines a foot; and
wherein the housing extension contacts the foot to prevent the handle from achieving the first handle position as the handle moves from the second handle position toward the first handle position while the motor, shaft, and stylet are in the second position.

7. The device of claim 1, wherein the power source comprises a battery.

8. The device of claim 7, wherein the battery is selected from the group consisting of alkaline batteries, nickel-cadmium batteries, and lithium ion batteries.

9. The device of claim 7, wherein the battery comprises an alkaline battery.

10. The device of claim 7, wherein the battery comprises a rechargeable battery.

11. The device of claim 1, further comprising a light disposed on the housing, the light operably connected to the power source when the handle in in the second position.

12. The device of claim 11, wherein the light is disposed adjacent the housing opening.

13. A device for establishing access to an intramedullary space of a bone, said device comprising:
a housing having a first end defining a housing opening, a second end, and a wall defining a housing internal chamber and an elongate slide opening in communication with the housing internal chamber;
a handle defining a handle internal chamber;
a hinge connecting the housing and the handle and having a hinge axis, the handle movable about the hinge axis between a first handle position and a second handle position;
a power source disposed within the handle internal chamber;
a motor disposed within the housing internal chamber, the motor including a rotatable shaft and operably connected to the power source when the handle is in the second handle position;
a stylet attached to the shaft;
a slide grip connected to the motor and extending through the slide opening;
a spring disposed within the housing internal chamber and connected to the motor, the spring biased to move the motor toward the second, end of the housing;
a switch adapted to activate the motor to rotate the shaft and the stylet; and
a cannula releasably disposed on the stylet;
wherein the motor, shaft, and stylet are movable within the housing internal chamber from a first position in which the stylet is disposed within the housing internal chamber to a second position in which the stylet extends through the housing opening; and
wherein the slide grip moves along the slide opening in a first direction as the motor, shaft, and stylet move from the first position to the second position and along the slide opening in a second, opposite direction as the motor, shaft, and stylet move from the second position to the first position.

14. The device of claim 13, wherein the handle extends alongside the housing when the handle is in the first handle position.

15. The device of claim 14, wherein the handle extends away from the housing when the handle is in the second handle position.

16. The device of claim 13, wherein the handle has a handle lengthwise axis and the housing has a housing lengthwise axis; and
wherein the handle lengthwise axis and the housing lengthwise axis are parallel when the handle is in the first handle position; and
wherein the handle lengthwise axis and the housing lengthwise axis arc not parallel when the handle is in the second handle position.

17. The device of claim 13, further comprising a housing extension releasably connected to the motor;
wherein the housing extension extends through the housing opening when the motor, shaft, and stylet are in the second position.

18. The device of claim 13, wherein the power source comprises a battery.

19. The device of claim 18, wherein the battery comprises a rechargeable battery.

20. A device for establishing access to an intramedullary space of a bone, said device comprising:
a housing having a first end defining a housing opening, a second end, and a wall defining a housing internal chamber and an elongate slide opening in communication with the housing internal chamber;
a handle;
a hinge connecting the housing and the handle and having a hinge axis, the handle movable about the hinge axis between a first handle position and a second handle position;
a power source;
a motor disposed within the housing internal chamber, the motor including a rotatable shaft and operably connected to the power source when the handle is in the second handle position;
a stylet attached to the shaft;
a slide grip connected to the motor and extending through the slide opening; and
a cannula releasably disposed on the stylet;
wherein the motor, shaft, and stylet are movable within the housing internal chamber from a first position in which the stylet is disposed within the housing internal chamber to a second position in which the stylet extends through the housing opening; and
wherein the slide, grip moves along the slide opening in a first direction as the motor, shaft, and stylet move from the first position to the second position and along the slide opening in a second, opposite direction as the motor, shaft, and stylet move from the second position to the first position.

* * * * *